(12) United States Patent
Miyamoto et al.

(10) Patent No.: US 7,879,817 B2
(45) Date of Patent: Feb. 1, 2011

(54) HYALURONIC ACID DERIVATIVE AND DRUG CONTAINING THE SAME

(75) Inventors: Kenji Miyamoto, Higashiyamato (JP); Yousuke Yasuda, Higashiyamato (JP); Keiji Yoshioka, Higashiyamato (JP)

(73) Assignee: Seikagaku Corporation, Tokyo (JP)

( * ) Notice: Subject to any disclaimer, the term of this patent is extended or adjusted under 35 U.S.C. 154(b) by 560 days.

(21) Appl. No.: 10/585,417

(22) PCT Filed: Jan. 7, 2005

(86) PCT No.: PCT/JP2005/000125

§ 371 (c)(1),
(2), (4) Date: Apr. 10, 2007

(87) PCT Pub. No.: WO2005/066214

PCT Pub. Date: Jul. 21, 2005

(65) Prior Publication Data

US 2008/0221062 A1   Sep. 11, 2008

(30) Foreign Application Priority Data

Jan. 7, 2004   (JP)   .............................. 2004-002478

(51) Int. Cl.
*A01N 43/04* (2006.01)
*A61K 31/715* (2006.01)
*A61K 31/70* (2006.01)
*A61P 29/00* (2006.01)

(52) U.S. Cl. .......................................... 514/54; 514/25

(58) Field of Classification Search ........................ None
See application file for complete search history.

(56) References Cited

FOREIGN PATENT DOCUMENTS

| | | | |
|---|---|---|---|
| EP | 1082963 A1 | * | 3/2001 |
| JP | 63-105003 A | | 5/1988 |
| JP | 06-72893 A | | 3/1994 |
| JP | 9-188705 | * | 7/1997 |
| JP | 09-188705 A | | 7/1997 |
| WO | WO 89/02445 A | | 3/1989 |
| WO | WO 92/06714 A1 | | 4/1992 |
| WO | WO09618388 | * | 6/1996 |
| WO | WO 99/59603 A1 | | 11/1999 |

OTHER PUBLICATIONS

Oude-Elferink, S.J.W.H., Krooneman, J., Gottschal, J.C., Spoelstra, S.F., Faber, F., Driehuis, F. (2001) Anaerobic conversion of Lactic Acid to Acetic Acid and 1,2-Propanediol by *Lactobacillus buchneri*. Applied and Environmental Microbiology, vol. 67, No. 1, p. 125-132.*
Definition of "derivative" from the Merriam Webster Online Dictionary [online], [Retrieved on Jan. 7, 2009]. Retrieved from the internet <http://www.merriam-webster.com/dictionary/derivative>.*
Perioli, L., Ambrogi, V., Bernardini, C., Grandolini, G., Ricci, M., Giovagnoli, S., Rossi, C. (2004) Potential prodrugs of non-steroidal anti-inflammatory agents for targeted drug delivery to the CNS. European Journal of Medicinal Chemistry, vol. 39, p. 715-727.*
International Search Report for PCT/JP05/000125.
New Zealand Examination Report dated Nov. 9, 2009 in Application No. 549010.
Philippine Office Action (Paper No. 9) dated Mar. 1, 2010 in Application No. 1-2006-501524.
New Zealand Examination Report dated Feb. 9, 2009.
Daniel A. Gamache et al., "Nepafenac, a Unique Nonsteroidal Prodrug with Potential Utility in the Treatment of Trauma-Induced Ocular Inflammation: I. Assessment of Anti-Inflammatory Efficacy", Inflammation, 2000, pp. 357-370, vol. 24, No. 4, Plenum Publishing Corp.

* cited by examiner

*Primary Examiner*—Shaojia Anna Jiang
*Assistant Examiner*—Scarlett Goon
(74) *Attorney, Agent, or Firm*—Sughrue Mion, PLLC

(57) ABSTRACT

A hyaluronic acid derivative in which an anti-inflammatory drug is bound to hyaluronic acid through a covalent bond via a spacer having a biodegradable region, and a production process thereof.

22 Claims, 10 Drawing Sheets

HYALURONIC ACID DERIVATIVE AND DRUG CONTAINING THE SAME

TECHNICAL FIELD

The present invention relates to hyaluronic acid derivatives to which a non-steroidal anti-inflammatory drug or a disease-modifying anti-rheumatic drug is introduced via a spacer which is biodegradable, and production methods thereof.

BACKGROUND ART

A sodium hyaluronate solution is used as a therapeutic agent for arthritis such as osteoarthritis of knee (OA) or rheumatoid arthritis of knee (RA). The sodium hyaluronate solution is generally used as injections by the direct administration to the affected knee joints, and shoulder joints, and frequently used for the purpose of improving functional disorders and suppressing pain caused by the arthritis.

Non-steroidal anti-inflammatory drugs (hereinafter also referred to as "NSAIDs" or "NSAID") and disease-modifying anti-rheumatic drugs (hereinafter also referred to as "DMARD"), which improve morbid states such as articular rheumatism, are also used as agents for suppressing or alleviating pains caused by such arthritis. In general, these NSAIDs are orally administered in many cases, and there are also frequent cases in which concomitant use of the injection of the above-described sodium hyaluronate solution and oral administration of NSAIDs. In the case of the oral administration of these NSAIDs, there is a problem in that the greater part of the NSAIDs are metabolized while circulating in the blood stream before they reach the affected site. To circumvent this problem, high dosage of NSAIDs are necessary to maintain effective concentration in the blood in order to deriver NSAIDs to the affected part. However, such high dosage of NSAIDs by the oral administration causes serious gastrointestinal adverse effects.

In addition, immunotherapy agents (immunomodulators and immunosuppressants) are used as DMARD for controlling immune abnormality or the like which is considered to be a cause of inflammation.

On the other hand, Hyaluronic acid is a polysaccharide constituted by a repeating structure with a disaccharide unit of N-acetyl-D-glucosamine and D-glucuronic acid as the basic core structure, and it is known to be highly hydrophilic due to the carboxyl group and a number of hydroxyl group in the disaccharide unit. As an example that hyaluronic acid has hydrophilic property, namely high hydration with water molecule, hyaluronic acid can hold water about 1,000-fold larger than its own weight. However, when highly hydrophobic agents such as NSAIDs are introduced into hyaluronic acid having such a high hydrophilic property, it is conventionally known that hydrophobic property of hyaluronic acid molecule itself increases so that water-semi-insoluble gel or insoluble matter are formed. Consequently, those water-semi-insoluble gel or insoluble matter are not suitable for the injectable use. Furthermore, with the increase of the degree of substitution of medicament for the purpose of longer sustained release, the insolubility is also increased so that it takes a form inappropriate as injections.

As an example in which not only NSAIDs but also other medicaments were introduced into hyaluronic acid, there is a report on a conjugate in which a matrix metalloproteinase inhibitor (MMP inhibitor) as an arthritis treating agent and hyaluronic acid were bound to each other via a spacer or not via the spacer (Patent Reference 1). However, as a suitable binding mode of the MMP inhibitor with hyaluronic acid, stronger covalent bond is exemplified in the report, and it suggests that a synergistic medicament effect of the action of the MMP inhibitor and the effect of hyaluronic acid can be expected on the assumption that the conjugate are not dissociated and degraded into the MMP inhibitor and hyaluronic acid in the administered region. In addition, it exemplifies carboxyl group as the binding region with hyaluronic acid, however, the degree of substitution of the medicament to the carboxyl group is considerably low, or a treatment for keeping suitable embodiment (solution) as injections is not carried out.

As other examples, there is a case in which hyaluronic acid is activated with water-soluble carbodiimide, and nucleophilic reagents were allowed to react therewith (Patent Reference 2), but these medicaments were not NSAIDs, and the final dosage form was an insoluble film. In addition, there is a case in which various medicaments were introduced into hyaluronic acid using a halogenated di-lower alkylphosphinothioyl (Rpt-X) as the condensing agent (Patent Reference 3), but dosage forms of the prepared derivatives are not described, and a treatment for enabling them as solution in the preparation is not included in the process.

Patent Reference 1: WO 99/59603

Patent Reference 2: JP-T-3-502704

Patent Reference 3: JP-A-9-188705

DISCLOSURE OF THE INVENTION

Problems to be Solved by the Invention

A method in which the problematic point as gastrointestinal adverse effects caused by the oral administration of NSAIDs is avoided by direct injection NSAIDs into the affected site can be considered. Although theoretically, but for example, when NSAIDs are directly injected into the knee joint cavity, the period of time for continuing the effect of NSAIDs is short due to quick absorption, so that such a method is not adopted. In addition, since NSAIDs themselves aim at alleviating or suppressing pain, such a method does not become a basic remedy for arthritis.

Accordingly, the present invention aims at providing a pharmaceutical agent which can greatly contribute to the alleviation or suppression of pain accompanied by arthritis and basic remedy for arthritis, by preparing a novel derivative in which one of NSAIDs or DMARD is chemically introduced into an arthritis treating agent, sodium hyaluronate, and injecting this into the affected site, and providing a pharmaceutical agent which shows its prolonged effect through the controlled release of NSAIDs or DMARD.

Means for Solving the Problems

Taking the above-described problems into consideration, the present inventors have conducted intensive studies with the aim of developing NSAIDs-introduced hyaluronic acid derivatives and DMARD-introduced hyaluronic acid derivatives, which can be used as injections into the affected site of arthritis patients, and also have high effects in not only radically treating arthritis but also alleviating or suppressing pain and inflammation.

As a result, it was found that derivatives in which NSAIDs and DMARD are introduced into hyaluronic acid via a spacer having a biodegradable region are suitable for the above-described objects, and further preferably that soluble NSAIDs-introduced hyaluronic acid derivatives and soluble DMARD-introduced hyaluronic acid derivatives, which can be used as injectable solutions in the form of infusions (injections), can be obtained through the improvement of solubility by adding an alkali treatment to the production process, thereby accomplishing the present invention.

That is, the present invention relates to the followings:

(1) A hyaluronic acid derivatives in which anti-inflammatory drugs are bound to hyaluronic acid through a covalent bond via a spacer having a biodegradable region.

(2) The hyaluronic acid derivatives according to the above-described (1), wherein the anti-inflammatory drugs are selected from non-steroidal anti-inflammatory drugs and disease-modifying anti-rheumatic drugs.

(3) The hyaluronic acid derivatives according to the above-described (1) or (2), wherein the anti-inflammatory drugs have a carboxyl group.

(4) The hyaluronic acid derivatives according to the above-described (3), wherein the anti-inflammatory drug is a residue of a compound selected from the group consisting of salicylic acid, aspirin, mefenamic acid, tolfenamic acid, flufenamic acid, diclofenac, sulindac, fenbufen, indometacin, acemetacin, amfenac, etodolac, felbinac, ibuprofen, flurbiprofen, ketoprofen, naproxen, pranoprofen, fenoprofen, tiaprofenic acid, oxaprozin, loxoprofen, alminoprofen, zaltoprofen, piroxicam, tenoxicam, lornoxicam, meloxicam, tiaramide, tolmetin, diflunisal, acetaminophen, floctafenine, tinoridine and actarit.

(5) The hyaluronic acid derivatives according to any one of the above-described (1) to (4), wherein the spacer is a compound having at least one functional group which binds to the hyaluronic acid and one functional group which binds to the anti-inflammatory drug.

(6) The hyaluronic acid derivatives according to any one of the above-described (1) to (5), wherein the spacer is selected from a diaminoalkane having from 2 to 18 carbon atoms, an aminoalkyl alcohol having from 2 to 12 carbon atoms which may have a substituent(s), and an amino acid.

(7) The hyaluronic acid derivatives according to any one of the above-described (1) to (6), wherein the hyaluronic acid has a weight average molecular weight of from 500,000 to 3,000,000.

(8) The hyaluronic acid derivatives according to any one of the above-described (1) to (7), wherein the anti-inflammatory drug is introduced at a ratio of from 5 to 50 mol % per repeating disaccharide unit of hyaluronic acid.

(9) A hyaluronic acid derivatives in which a non-steroidal anti-inflammatory drug is bound to hyaluronic acid through a covalent bond, which has a partial structure of hyaluronic acid disaccharide unit into which the anti-inflammatory drug is introduced is represented by the following formula (1):

wherein Y—CO— represents one residue of the hyaluronic acid disaccharide unit;

$R^2$ represents a non-steroidal anti-inflammatory drug residue represented by Z—CO— or hydrogen atom, with the proviso that all $R^2$'s are not hydrogen atoms;

—HN—$R^1$—(O—)$_n$ represents a spacer residue in a spacer compound represented by $H_2N$—$R^1$—$(OH)_n$ having n numbers of a hydroxyl group;

$R^1$ represents a linear or branched hydrocarbon group having from 2 to 12 carbon atoms which may have a substituent;

—CO—NH— represents an amide bond of a carboxyl group in glucuronic acid as a constituting saccharide of the hyaluronic acid with an amino group in the spacer compound;

—O—CO— represents an ester bond of a hydroxyl group in the spacer compound with a carboxyl group in the non-steroidal anti-inflammatory drug residue; and n is an integer of from 1 to 3, wherein the hyaluronic acid derivative has a degree of substitution of the non-steroidal anti-inflammatory drug of from 5 to 50 mol % per repeating disaccharide unit of hyaluronic acid, and the carbonyl group in a hyaluronic acid residue constituting the hyaluronic acid derivative is present as an amide bond participating in the binding with the spacer-binding anti-inflammatory drug residue or as a free carboxyl group not participating therein, according to the degree of substitution of the non-steroidal anti-inflammatory drug residue.

(10) The hyaluronic acid derivatives according to the above-described (9), wherein the non-steroidal anti-inflammatory drug is a compound represented by the following formula (2):

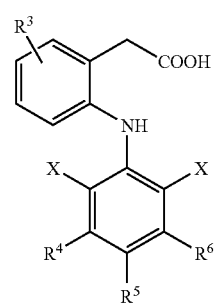

wherein $R^3$ represents a substituent selected from a lower alkyl group and a lower alkoxyl group, or a hydrogen atom;

$R^4$, $R^5$ and $R^6$ each independently represents a substituent selected from a group consisting of lower alkyl group, a lower alkoxyl group and a hydroxyl group, a halogen atom, or a hydrogen atom; and X's are the same or different and each represents a substituent selected from a lower alkyl group and a trifluoromethyl group, or a halogen atom, and at least one of X's is a halogen atom.

(11) The hyaluronic acid derivatives according to the above-described (10), wherein the non-steroidal anti-inflammatory drug is diclofenac or a derivative thereof

(12) The hyaluronic acid derivatives according to any one of the above-described (9) to (11), wherein $R^1$ in formula (1) is an ethylene group, a trimethylene group or a propylene group, which may have a substituent(s).

(13) The hyaluronic acid derivatives according to any one of the above-described (1) to (12), which is obtainable by a method comprising reacting hyaluronic acid with a spacer-bound anti-inflammatory drug, or reacting a spacer-bound hyaluronic acid with an anti-inflammatory drug, and adjusting the reaction solution to alkaline conditions.

(14) The hyaluronic acid derivatives according to any one of the above-described (1) to (13), wherein a solution obtained by dissolving the hyaluronic acid derivative in an aqueous medium to a concentration of 1.0% by weight is capable of passing through a porous filter having a pore size of 0.45 μm and a diameter of 25 mm, at a ratio of 2 mL per minute or more at a temperature of 24° C. under pressure of 5.0 kg/cm².

(15) The hyaluronic acid derivatives according to any one of the above-described (1) to (13), wherein a solution obtained by dissolving the hyaluronic acid derivative in an aqueous medium to a concentration of 1.0% by weight is capable of passing through a porous filter having a pore size of 0.22 μm and a diameter of 25 mm, at a ratio of 2 mL per minute or more at a temperature of 24° C. under pressure of 5.0 kg/cm².

(16) A hyaluronic acid derivative solution which is capable of being pushed out from an injector and which comprises the hyaluronic acid derivative according to any one of the above-described (1) to (15) dissolved in an aqueous medium.

(17) The hyaluronic acid derivative solution according to the above-described (16), wherein the aqueous medium is an aqueous medium selected from phosphate buffered saline, saline and water for injection.

(18) The hyaluronic acid derivative solution according to the above-described (17), which is sterilized through a filter.

(19) A pharmaceutical agent which comprises the hyaluronic acid derivative according to any one of the above-described (1) to (15) as an active ingredient.

(20) The pharmaceutical agent according to the above-described (19), which is an arthritis treating agent, an anti-inflammatory medicament or an analgesic.

(21) The pharmaceutical agent according to the above-described (19) or (20), which is useful for parenteral administration.

(22) The pharmaceutical agent according to the above-described (21), which is an injection useful for topical administration.

(23) The pharmaceutical agent according to the above-described (21) or (22), which is an injection useful for intra-articular administration.

(24) A pharmaceutical agent which is capable of being pushed out from an injector and which comprises a solution in which the hyaluronic acid derivative according to any one of the above-described (1) to (15), as an active ingredient, is dissolved in an aqueous medium.

(25) A kit for injection of a hyaluronic acid derivative, which comprises the hyaluronic acid derivative solution according to any one of the above-described (16) to (18) which is filled in an injector capable of pushing out the solution.

(26) The kit according to the above-described (25), wherein the filled solution is the pharmaceutical agent according to any one of the above-described (19) to (24).

(27) A medical injection kit which is sealed with a plunger for medicament extrusion in such a manner that it can be slid and which comprises a syringe filled with a solution in which the hyaluronic acid derivative according to any one of the above-described (1) to (15) is dissolved in pharmaceutically acceptable phosphate buffered saline, saline or water for injection.

(28) A derivative in which a spacer having a biodegradable region is bound with an anti-inflammatory drug via a covalent bond.

(29) The derivative according to the above-described (28), wherein the spacer having a biodegradable region is a residue of a diaminoalkane, an aminoalkyl alcohol or an amino acid.

(30) The derivative according to the above-described (28) or (29), wherein the spacer having a biodegradable region is a residue of a compound capable of binding two or more anti-inflammatory drugs to one mole of the spacer.

(31) The derivative according to any one of the above-described (28) to (30), wherein the anti-inflammatory drug is a residue of a compound selected from the group consisting of salicylic acid, aspirin, mefenamic acid, tolfenamic acid, flufenamic acid, diclofenac, sulindac, fenbufen, indometacin, acemetacin, amfenac, etodolac, felbinac, ibuprofen, flurbiprofen, ketoprofen, naproxen, pranoprofen, fenoprofen, tiaprofenic acid, oxaprozin, loxoprofen, alminoprofen, zaltoprofen, piroxicam, tenoxicam, lornoxicam, meloxicam, tiaramide, tolmetin, diflunisal, acetaminophen, floctafenine, tinoridine and actarit.

(32) The derivative according to any one of the above-described (28) to (31), wherein the covalent bond is an ester bond or an amide bond.

(33) The derivative according to the above-described (32), which is represented by the following formula (3):

$$H_2N-R^1-(O-R^2)_n \quad (3)$$

wherein $R^2$ represents a hydrogen atom or a non-steroidal anti-inflammatory drug residue represented by Z—CO—, with the proviso that all $R^2$'s are not hydrogen atoms;

$H_2N-R^1-(O-)_n$ represents a spacer residue in a spacer compound represented by $H_2N-R^1-(OH)_n$ having n numbers of hydroxyl group;

$R^1$ represents a linear or branched hydrocarbon group having from 2 to 12 carbon atoms which may have substituents;

—O—CO— represents an ester bond consisting of a hydroxyl group in the spacer compound and a carboxyl group in the non-steroidal anti-inflammatory drug residue; and n is an integer of from 1 to 3.

(34) A process for producing a hyaluronic acid derivative which comprises hyaluronic acid bound to an anti-inflammatory drug through a covalent bond via a spacer having a biodegradable region, said process comprising:

reacting hyaluronic acid with a spacer-bound anti-inflammatory drug, or reacting a spacer-bound hyaluronic acid with an anti-inflammatory drug.

(35) The process for producing a hyaluronic acid derivative according to the above-described (34), which comprises treating a solution of a reaction product of hyaluronic acid with a spacer-bound anti-inflammatory drug or a solution of a reaction product of a spacer-bound hyaluronic acid with an anti-inflammatory drug under alkaline conditions.

Advantage of the Invention

According to the present invention, hyaluronic acid derivatives in which an anti-inflammatory drug is bound to hyaluronic acid through a covalent bond via a spacer having a biodegradable region, particularly a non-steroidal anti-inflammatory drug-introduced hyaluronic acid derivative in which a non-steroidal anti-inflammatory drug is bound through a covalent bond (hereinafter referred to as "substance 1 of the present invention"), also a disease-modifying anti-rheumatic drug-introduced hyaluronic acid derivative in which a disease-modifying anti-rheumatic drug is bound through a covalent bond (hereinafter referred to as "substance 2 of the present invention", in this connection, the substance 1 of the present invention and the substance 2 of the present invention are also called "substance of the present invention" as a whole), and a pharmaceutical agent which comprises one of these derivatives as the active agent (hereinafter referred to as "pharmaceutical agent of the present invention") are provided. Since the substance of the present invention is sufficiently dissolved in a buffer, saline, water for injection or the like which is used as the solvent of injections or the like, it can be used as an injection that can be directly administered to the affected site. In addition, the pharmaceutical agent of the present invention can be used in the treatment of arthritis, suppression of inflammation and suppression of pain, and its parenteral administration or topical administration as injections (e.g., intraarticular administration) is also possible.

BRIEF DESCRIPTION OF THE DRAWINGS

FIG. 10 (b) is a graph showing effect of the administration of diclofenac-introduced hyaluronic acid derivative on adjuvant-non-injected paw on the adjuvant-induced arthritis (AIA) model in rat.

BEST MODE FOR CARRYING OUT THE INVENTION

Figure 1:
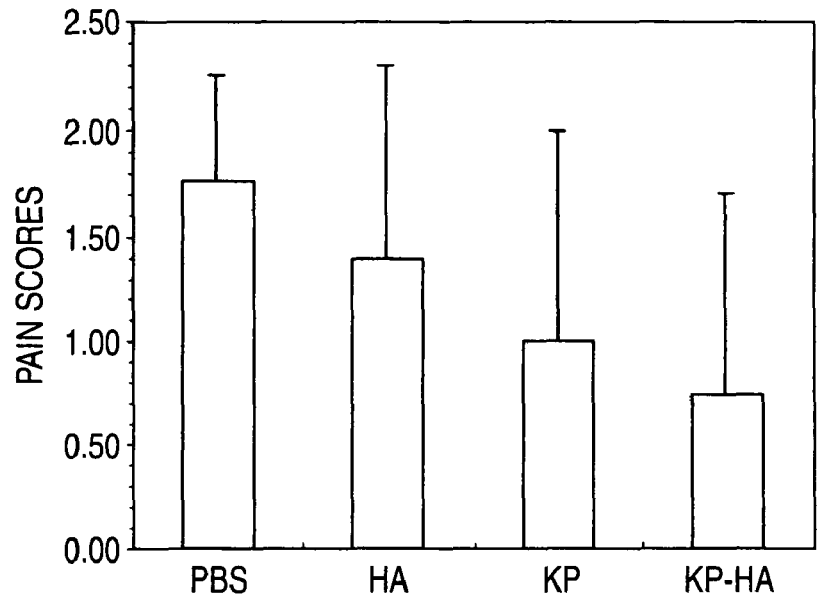
FIG. 1 is a graph showing pain scores on the bradykinin-induced pain model in rat.

The present invention is described below based on embodiments of the present invention.

The substance of the present invention is a hyaluronic acid derivative in which an anti-inflammatory drug is bound to hyaluronic acid through a covalent bond via a spacer having a biodegradable region. According to the present invention, the anti-inflammatory drug is selected from non-steroidal anti-inflammatory drugs (NSAID or NSAIDs) and disease-modifying anti-rheumatic drugs (DMARD).

In this connection, the terminology "NSAIDs" generally means more than one non-steroidal anti-inflammatory drugs, in which two or more drug are classified, and "NSAID" means each non-steroidal anti-inflammatory drug in some cases, but they are not strictly differentiated in this description.

The substance 1 of the present invention is a hyaluronic acid derivatives in which a non-steroidal anti-inflammatory drug is bound via a covalent bond, and its structure is conceptually represented by the following formula (4):

$$\text{HA-SP-NSAID} \quad (4)$$

wherein HA represents a hyaluronic acid chain; SP represents a spacer residue; NSAID represents a non-steroidal anti-inflammatory drug residue, and — represents a covalent bond.

In addition, the substance 2 of the present invention is a hyaluronic acid derivative in which a disease-modifying anti-rheumatic drug is bound via a covalent bond, and its structure is conceptually represented by the following formula (5):

$$\text{HA-SP-DMARD} \quad (5)$$

wherein HA represents a hyaluronic acid chain; SP represents a spacer residue; DMARD represents a disease-modifying anti-rheumatic drug residue; and — represents a covalent bond.

The substance of the present invention can be dissolved in an aqueous solvent, and it is a viscous solution.

The term "aqueous solvent" as used herein means water, a buffer solution containing water, and an aqueous solution or a buffer solution containing a pharmaceutically acceptable metal salt, a pH adjusting agent or the like. The specific examples include water for injection, phosphate buffered saline, saline and the like.

The hyaluronic acid to be used in the substance of the present invention is not particularly limited, so long as it is a glycosaminoglycan which consists of a disaccharide unit consisting of N-acetyl-D-glucosamine and D-glucuronic acid bound through a β1,3 bond as the basic core structure and is constructed by repeating β1,4 bond of the disaccharide unit, namely a generally used hyaluronic acid. In addition, it is possible to use those which are derived from animals or microorganisms or chemical synthesis.

The weight average molecular weight of hyaluronic acid is not particularly limited, but from 10,000 to 5,000,000 can be exemplified. Preferably from 500,000 to 3,000,000, and more preferably from 600,000 to 1,500,000 and from 1,500,000 to 3,000,000 as standards used in an arthritis treating agent and can be exemplified.

In this connection, the hyaluronic acid to be used in the present invention may be either in a free form of not forming a salt or a pharmaceutically acceptable salt. The pharmaceutically acceptable salt of hyaluronic acid includes salts with alkali metal ions such as a sodium salt, a potassium salt, and salts with alkaline earth metal ions such as a magnesium salt, and a calcium salt. When a hyaluronic acid derivative is used in a pharmaceutical preparations or the like for use in the living body, the hyaluronic acid salt to be used is preferably a salt with an alkali metal ion, particularly a salt with a sodium ion, because of its high affinity for the living body.

The NSAIDs as one of the anti-inflammatory drugs concerned in the present invention generally mean the whole compounds which are usually called non-steroidal anti-inflammatory agents and are not particularly limited, but those which are applied to arthritis are particularly preferable. As a conventional classification method of NSAIDs, there is a classification based on the difference of its core structure in chemical structure. When the NSAIDs to be applied to the present invention are exemplified based on this classification, salicylic acid type NSAIDs include salicylic acid, aspirin and the like; fenamic acid type NSAIDs include mefenamic acid, tolfenamic acid, flufenamic acid and the like; aryl acetate type NSAIDs include diclofenac, sulindac, fenbufen, indometacin, acemetacin, amfenac, etodolac, felbinac and the like; propionic acid type NSAIDs include ibuprofen, flurbiprofen, ketoprofen, naproxen, pranoprofen, fenoprofen, tiaprofenic acid, oxaprozin, loxoprofen, alminoprofen, zaltoprofen and the like; oxicam type NSAIDs include piroxicam, tenoxicam, lornoxicam, meloxicam and the like; and other NSAIDs include tiaramide, tolmetin, diflunisal, acetaminophen, floctafenine, tinoridine and the like.

As the NSAIDs to be applied to the present invention, those which have a functional group such as a carboxyl group, a hydroxyl group or an amino group in the chemical structure are preferable. Since it is possible to select functional group of the spacer according to the functional groups of these NSAIDs, the substance 1 of the present invention is not particularly limited, but the NSAIDs which at least have a carboxyl group are most preferably used.

Among these, compounds which have the core structure represented by the following formula (6) are more preferably used:

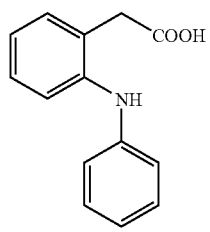

(6)

Furthermore, the compounds represented by the following formula (2) are particularly preferably used:

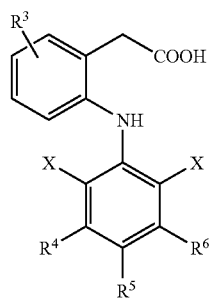

(2)

$R^3$ represents a substituent selected from lower alkyl groups and lower alkoxyl groups, or a hydrogen atom; $R^4$, $R^5$ and $R^6$ each independently represents a substituent selected from a lower alkyl group, a lower alkoxyl group and a hydroxyl group, a halogen atom, or a hydrogen atom; and X's are the same or different each other, and each independently represents a substituent selected from a lower alkyl group and a trifluoromethyl group, or a halogen atom, wherein at least one of X's is a halogen atom. In addition, the above-described lower alkyl group and lower alkoxyl group are preferably a lower alkyl group and a lower alkoxyl group having from 1 to 12 carbon atoms which are allowed to be branched, and more preferably a lower alkyl group and a lower alkoxyl group having from 1 to 6 carbon atoms which are allowed to be branched.

Also, when a carboxymethyl group and an amino residue are positioned at the 1-position and 2-position, respectively, of the benzene ring to which $R^3$ is bound, $R^3$ is preferably bound to the 5-position.

As the compounds represented by the above-described formula (2), for example, the compounds described in WO 99/11605 can be cited, and the contents described therein are incorporated herein by reference. Carboxyl group in the NSAIDs is not limited to free form but also to salt form.

The DMARD as the other one of the anti-inflammatory drugs concerned in the present invention generally mean whole pharmaceutical preparations usually used as anti-rheumatic agents and are not particularly limited, but those which have a functional group, such as a carboxyl group, a hydroxyl group, an amino group or a mercapto group in the chemical structure are preferable. The DMARD includes actarit, methotrexate, salazosulfapyridine, bucillamine and the like.

In this connection, the above-described NSAID and DMARD can be cited as the anti-inflammatory drugs concerned in the present invention, but the compounds which have carboxyl group are particularly preferable.

In this connection, it is possible to introduce those functional groups to hyaluronic acid via a desired binding mode by selecting functional group of the spacer moiety depending on the functional groups owned by the above-described NSAIDs and DMARD. In addition, it is not always necessary that one species of NSAID or DMARD is introduced into the substance of the present invention, and hyaluronic acid derivatives to which two or more species of NSAID and DMARD are introduced are also included therein.

The above-described spacer represented by SP is a spacer which has a region that can be biodegraded and is the residue of a compound having at least one functional group which binds to hyaluronic acid and one functional group which binds to NSAIDs or DMARD (hereinafter also referred to as "spacer compound"). The region of the spacer which can be biodegraded is not particularly limited, so long as the NSAIDs or DMARD released from the hyaluronic acid derivatives have the effect, but it is preferable that the region is cleaved at the binding region of NSAIDs or DMARD with the spacer.

Respective functional groups of the spacer compound can be optionally selected depending on the binding modes with hyaluronic acid and NSAIDs or DMARD. For example, when spacer molecule is introduced at the carboxyl group of the hyaluronic acid through amide bond, a spacer compound with amino group can be selected, and in the case of ester bond at the carboxyl group of the hyaluronic acid, spacer with hydroxyl group can be selected. If the spacer is introduced at the hydroxyl group of the hyaluronic acid through ester bond, spacer with carboxyl group can be selected. In this case, from the viewpoint of the conciseness for the introduction of spacer molecule into hyaluronic acid and the stability in the living body, a spacer compound having amino group which can be introduced into the carboxyl group of hyaluronic acid through amido bond can be cited as one of the preferable embodiments.

In the same manner, the functional group of a spacer compound which binds to NSAIDs or DMARD can also be selected based on the functional group owned by NSAIDs or DMARD. For example, in the case of NSAIDs or DMARD having hydroxyl group, it can be bound through an ester bond when a spacer compound having carboxyl group is selected, in the case of NSAIDs or DMARD having carboxyl group, it can be bound through an ester bond when a spacer compound having hydroxyl group is selected, or can be bound through an amide bond when a spacer compound having amino group is selected, and in the case of NSAIDs or DMARD having mercapto group, it can be bound through thioester bond when a spacer compound having carboxyl group is selected.

In this case, when the aptness to be biodegraded is taken into consideration, a spacer compound having a functional group which can bind through an ester bond to the carboxyl group of NSAIDs or DMARD is preferable, and it is particularly preferable that the carboxyl group of NSAIDs or DMARD and the hydroxyl group of the spacer compound are bound through an ester bond.

As described above, it is possible to select spacer compound optionally in accordance with the characteristics of hyaluronic acid and NSAIDs or DMARD, but, for example, a diaminoalkane having from 2 to 18 carbon atoms, an aminoalkyl alcohol having from 2 to 12 carbon atoms which may have a substituent(s), an amino acid and the like can be exemplified. The amino acid may be a naturally occurring or non-naturally occurring amino acid and is not particularly limited, but preferably, glycine, β-alanine and γ-aminobutyric acid can be exemplified.

As described above, when the binding mode of hyaluronic acid with NSAIDs is taken into consideration, an aminoalkyl alcohol having from 2 to 12 carbon atoms which may have a substituent can be cited as a preferable example of the spacer compound.

In addition, it may be a spacer compound which has two or more of these functional groups capable of binding to NSAIDs or DMARD, in one molecule (hereinafter also referred to as "multivalent spacer compound").

When a multivalent spacer compound is selected, two or more of NSAIDs or DMARD can be bound simultaneously to one spacer. Accordingly, two or more of NSAIDs or DMARD can be introduced simultaneously into the functional group, for example, one carboxyl group, of hyaluronic acid to which the NSAIDs or DMARD are to be introduced. Examples of these multivalent spacer compounds include serinol and a derivative thereof, a serine derivative, a threonine derivative, 2-amino-1,5-pentanediol and a derivative thereof, 3-amino-1,2-propanediol and a derivative thereof, tris(hydroxymethyl)aminomethane and a derivatives thereof, bishomotris and a derivatives and the like.

The merit of using this multivalent spacer compound is that more larger amount of NSAIDs or DMARD can be introduced without allowing a large number of carboxyl groups and hydroxyl groups contributing to the hydrophilic property of hyaluronic acid to the substitution reaction, so that hydrophilic property, namely solubility in the aqueous medium can be kept in despite the large amount of NSAIDs or DMARD are introduced in the molecule.

The method for synthesizing the substance of the present invention is not particularly limited, so long as it is a method by which the soluble substance of the present invention as described above can be obtained.

In this connection, in the case of a hyaluronic acid derivative in which a compound is introduced into hyaluronic acid, the carboxyl group and hydroxyl group owned by hyaluronic acid generally take part in the binding to the compound, so that hydrophilic property of the hyaluronic acid derivative decreases as the degree of substitution of the substance increases.

An example of the method for synthesizing the substance 1 of the present invention include a method which comprises carrying out an alkali treatment after an introduction of NSAIDs into hyaluronic acid via a spacer having a region capable of being biodegraded.

The above-described method of alkali treatment after the introduction reaction in order to make the reaction solution alkaline is not particularly limited, so long as it is a treatment by which the solution becomes alkaline. Specifically, a method in which either an organic base or an inorganic base is added to the solution can be exemplified, but an inorganic base is preferable when the treatment thereafter and the like are taken into consideration. In addition, even among inorganic bases, weaker base such as sodium hydrogen carbonate or sodium carbonate is preferable rather than a stronger base such as sodium hydroxide, due to the lower influence on hyaluronic acid and NSAIDs. As the pH conditions of alkali treatment in this case, from 7.2 to 11, preferably from 7.5 to 10, can be exemplified.

The treating time of the alkali treatment is not particularly limited, so long as it does not exert influence on molecular weight reduction of hyaluronic acid, but from 2 to 12 hours, preferably from 2 to 6 hours, can be cited, and a soluble hyaluronic acid derivative can be obtained without exerting influence on hyaluronic acid when the treatment is carried out for the time period.

As a specific example, the intended soluble hyaluronic acid derivative can be obtained by allowing a spacer-introduced NSAIDs derivative to react with hyaluronic acid, adding a weak alkali such as sodium hydrogen carbonate to the reaction solution, followed by stirring for several hours, and then carrying out post-treatments such as neutralization, ethanol precipitation and drying.

The method described above can also be applied to the synthesis of the substance 2 of the present invention, so that a soluble substance 2 of the present invention can be obtained.

In this connection, the method for introducing a spacer and NSAIDs or DMARD into hyaluronic acid may be either a method in which the spacer is introduced into hyaluronic acid, and then NSAIDs or DMARD is introduced into the spacer-linked hyaluronic acid or a method in which a spacer is introduced into NSAIDs or DMARD in advance, and then the spacer-linked NSAIDs or the spacer-linked DMARD is introduced into hyaluronic acid, but the latter method is preferable.

The method for respectively binding NSAIDs or DMARD, hyaluronic acid and spacer is not particularly limited, but it is possible to use a generally used conventional method as a means for carrying out the binding reaction with the proviso that it is a method that can attain ester bond formation, amide bond formation, thioester bond formation and the like. And The reaction conditions can be optionally judged and selected by one skilled in the art.

In this connection, the condensation of hyaluronic acid with the spacer-linked NSAIDs or spacer-linked DMARD or with the spacer compound can be attained by using either the carboxyl group or hydroxyl group of hyaluronic acid. But the carboxyl group can more easily attain the condensation due to the higher reactivity owned by the functional group. The method for attaining such a condensation, for example, includes a method in which a water-soluble condensing agent such as a water-soluble carbodiimide (e.g., 1-ethyl-3-(3-dimethylaminopropyl)-carbodiimide hydrochloride (EDCI HCl), 1-ethyl-3-(3-dimethylaminopropyl)carbodiimide methiodide, etc.) is used, a method in which a condensation additive agent such as N-hydroxysuccinimide (HOSu) or N-hydroxybenzotriazole (HOBt) and the above-described condensing agent are used, an active ester method, an acid anhydride method and the like. Among these, the method in which a water-soluble condensing agent is used, or the method in which a condensation additive agent and a water-soluble condensing agent is used, as the reaction in the presence of an aqueous solvent, is preferable, and the method in which a condensation additive agent and a water-soluble condensing agent is used is particularly preferable from the viewpoint of inhibiting side reaction. It is preferable that the carboxyl group of hyaluronic acid is bound to the spacer-linked NSAIDs or spacer-linked DMARD or the spacer compound through an ester bond or an amide bond, more preferably through an amide bond.

It is possible to adjust the degree of substitution of NSAIDs or DMARD to hyaluronic acid regarding the substance of the present invention by changing the amount of the condensing agent, condensation additive agent, spacer-linked NSAIDs or spacer-linked DMARD during the process for synthesizing the substance of the present invention. In this connection, the degree of substitution can be measured by measuring absorbance or by a method which uses HPLC, NMR or the like.

According to the present invention, the degree of substitution of NSAIDs or DMARD is not particularly limited, so long as solubility of the derivative in the aqueous solvent is maintained, but from 0.1 to 80% by mol is preferable and from 5 to 50% by mol is more preferable, based on the repeating disaccharide unit of hyaluronic acid. In addition, when the substance of the present invention is used as an active ingredient of a pharmaceutical preparation, the optimum degree of substitution is determined by taking effective concentration or sustained release efficiency of NSAIDs or DMARD in the affected site into consideration.

As described above, a spacer-linked NSAIDs or spacer-linked DMARD is introduced into the carboxyl group of hyaluronic acid, the carboxyl group forms an amide bond or an ester bond to reduce or lose its hydrophilic property.

As one of the means for solving this problem, introduction of a number of NSAIDs or DMARD becomes possible while keeping the hydrophilic property, by using a multivalent spacer compound. For example, when an aminotriol derivative having 3 hydroxyl groups and 1 amino group is used as a spacer compound, introduction of NSAIDs into all of the 3 hydroxyl group results in the introduction of 3 molecules of NSAIDs into 1 spacer molecule. When this aminotriol-linked NSAIDs is introduced into the carboxyl group of hyaluronic acid, for example, at a degree of substitution (degree of substitution based on hyaluronic disaccharide unit) of 20%, it means that the degree of substitution of NSAIDs is 60% equivalent to 3 fold higher of the aminotriol-linked NSAIDs's degree of substitution.

In addition, as described above, solubility of the hyaluronic acid derivative in the aqueous medium is maintained when the method in which an alkali treatment is carried out after the introduction reaction for synthesizing an anti-inflammatory drug-introduced hyaluronic acid derivative, which was cited as an example of the method for synthesizing the substance of the present invention, is employed. This solubility keeping effect is markedly useful, because it is not so necessary to consider kind of the spacer compound, nor the degree of substitution of a medicament and the like, and the treatment is convenient.

In summarizing the above-described explanations, as a specifically preferable embodiment of the substance 1 of the present invention, a hyaluronic acid derivative having a disaccharide unit constituting hyaluronic acid represented by the following formula (1) can be for example cited. In this connection, the following formula (1) shows a partial structure per disaccharide unit constituting hyaluronic acid wherein an anti-inflammatory drug-introduced N-acetyl-D-glucosamine and D-glucuronic acid are bound via a β-1,3 bond.

wherein Y—CO— represents one residue of the disaccharide unit constituting hyaluronic acid; $R^2$ represents an NSAID residue represented by Z—CO— or a hydrogen atom, in which all $R^2$s are not hydrogen atoms; —HN—$R^1$—(O—)$_n$ represents a spacer residue in a spacer compound represented by $H_2N$—$R^1$—(OH)$_n$ having n numbers of hydroxyl group; $R^1$ represents a linear or branched hydrocarbon group having from 2 to 12 carbon atoms which may have a substituent(s); —CO—NH— represents an amide bond of a carboxyl group in glucuronic acid as a constituting saccharide of hyaluronic acid with an amino group in the spacer compound; —O—CO— represents an ester bond of a hydroxyl group in the spacer compound with the carboxyl group owned by NSAID; and n is an integer of from 1 to 3. In this connection, the carbonyl group in a hyaluronic acid residue constituting the hyaluronic acid derivative is present as an amide bond involved in the binding with the spacer-binding anti-inflammatory drug residue or as a free carboxyl group not involved thereto, according to the degree of substitution of the NSAID residue.

The substituent in $R^1$ includes an alkyl group, an alkenyl group, an aryl group, an alkoxy group, an acyl group, a carboxyl group, a halogen and the like, wherein the number of carbon atoms in the alkyl group, alkenyl group, alkoxy group and acyl group is preferably from 1 to 11, more preferably from 1 to 4, and the phenyl group is preferable as the aryl group. For example, serine can be exemplified as the spacer compound having a carboxyl group as the substituent, and threonine as the spacer compound having a carboxyl group and a methyl group.

In this connection, according to the above-described formula (1), Y—COOH represents one disaccharide unit constituting hyaluronic acid before the reaction; $H_2N$—$R^1$—(OH)$_n$ represents a spacer compound before the reaction; and HOOC—Z represents NSAID before the reaction.

As a most suitable method for synthesizing the hyaluronic acid-constituting disaccharide unit represented by the above-described formula (1), a method in which a spacer compound and NSAID are bound and then allowed to react with hyaluronic acid can be exemplified. Conceptual expression of this reaction is as follows.

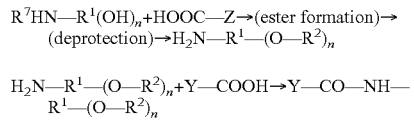

$R^7$ represents a protecting group of an amino group, wherein the protecting group is not particularly limited, because protecting groups generally used as the protecting group of an amino group can be used, and examples include a urethane type protecting group such as a tert-butoxycarbonyl group, a benzyloxycarbonyl group and a 9-fluorenylmethyloxycarbonyl group, and an acyl type protecting group such as a formyl group and a phthaloyl group, and a urethane type protecting group is preferable. In this connection, $R^1$, $R^2$ and Z are as defined above.

However, the above description is a conceptual explanation of the reaction pathway, and a design and the like for efficiently carrying out the reaction, which can be deduced by those skilled in the art, are omitted herein.

In the above-described formula (1), $R^1$ is more preferably a linear or branched chain hydrocarbon group having from 2 to 5 carbon atoms which may have a substituent(s), particularly preferably a hydrocarbon group having 2 or 3 carbon atoms, and examples include an ethylene group, a trimethylene group and a propylene group.

Also, as the NSAID to be used in the above-described formula (1), it is possible to select it from the above-described NSAID. In addition, compounds represented by the following formula (7) can be preferably exemplified.

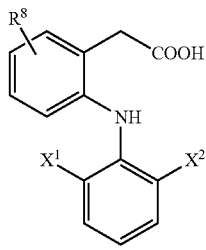

(7)

$R^8$ represents a substituent selected from a lower alkyl groups and a lower alkoxyl groups, or a hydrogen atom, and is more preferably a lower alkyl group having from 1 to 12 carbon atoms which may have a branch, or a hydrogen atom, and particularly preferably a lower alkyl group having from 1 to 4 carbon atoms or a hydrogen atom.

$X^1$ and $X^2$ each independently represents a substituent selected from lower alkyl groups and a trifluoromethyl group or a halogen atom, wherein at least one of them is a halogen atom. $X^1$ and $X^2$ are preferably halogen atoms which are the same or different, and more preferably selected from a fluorine atom and a chlorine atom.

In addition, it is preferable that $R^8$ is bound to the 5-position of the benzene ring to which $R^8$ is bound, when the carboxymethyl group and the amino group are positioned at the 1-position and the 2-position in the benzene ring, respectively.

Specific examples of the compounds represented by the above-described formula (7) include compounds represented by the following formulae (8) and (9):

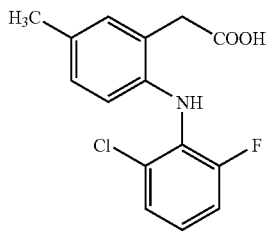

(8)

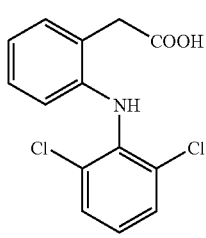

(9)

For example, when a diclofenac-introduced hyaluronic acid derivative is synthesized using the diclofenac represented by the formula (9), the —CO—Z in the above-described formula (1) is represented by the following formula (10):

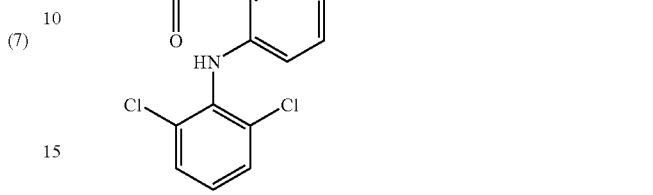

(10)

In this connection, the diclofenac-introduced hyaluronic acid derivatives have very strong analgesic action and anti-inflammatory action.

As the hyaluronic acid which can be used in the substance of the present invention having the disaccharide unit constituting hyaluronic acid represented by the above-described formula (1), preferably a hyaluronic acid having a weight average molecular weight of from 50,000 to 3,000,000, more preferably a hyaluronic acid having a weight average molecular weight of from 50,000 to 2,000,000, is selected.

The degree of substitution of NSAIDs (DS) in the substance of the present invention having the disaccharide unit constituting hyaluronic acid represented by the above-described formula (1) is preferably from 5 to 50% by mol, more preferably from 10 to 50% by mol, based on the repeating disaccharide unit of hyaluronic acid.

As a significant characteristic of the substance of the present invention, a point that the substance of the present invention can be dissolved in an aqueous solvent, namely easily water-soluble, can be cited, so that when an aqueous solvent is added to the substance of the present invention, it dissolves without carrying out heating, solubilization treatment and the like. In this connection, even when the degree of substitution is high, namely 5% or more, or further 10% or more, it can be dissolved. Thus, a solution prepared by dissolving the substance of the present invention in an aqueous medium is an injectable liquid and has an ability to pass through a filtration filter. By the way, as described above, it is known that when a medicament having higher hydrophobic property, such as NSAIDs or DMARD, is introduced into hyaluronic acid having higher hydrophilic property, the product becomes water-semi-insoluble gel having high viscoelasticity or insoluble matter because of the increase of hydrophobic property of the hyaluronic acid molecule itself, so that such a product is not suitable for injections which are extruded by an injector.

However, since solubility of the hyaluronic acid derivative is maintained for example by carrying out an alkali treatment during its production process as described above, the substance of the present invention can be a transparent solution having the ability to pass through a filtration filter.

Thus, the solution of the substance of the present invention can be subjected to a filtration so that dust removal, removal of microorganisms and sterilization of microorganisms by filtration can be possible. That is, removal of dust and microorganisms can be effective by passing through a 5 μm or 0.45 μm filter, and more preferably, sterilization also becomes possible by passing through a 0.22 μm filter.

More specifically, it is preferable that a solution prepared by dissolving the substance of the present invention in an aqueous medium to be a concentration of 1.0% by weight is capable of passing through a porous filter (pore size 0.45 μm, diameter 25 mm) at a ratio of 2 mL per minute or more at a temperature of 24° C. under pressure of 5.0 kg/cm².

Also, it is more preferable that a solution prepared by dissolving the substance of the present invention in an aqueous medium to be a concentration of 1.0% by weight is capable of passing through a porous filter (pore size 0.22 μm, diameter 25 mm) at a ratio of 2 mL per minute or more under the same conditions described above.

As described below, when the substance of the present invention is used as a medicament to be applied to a living body (a mammal, particularly preferably human), dust removal, and removal of microorganisms, and sterilization of microorganisms become essential items so that such a characteristic of the substance of the present invention is markedly useful. In addition, in the case of the sterilization by heating, ultraviolet ray irradiation or the like, there is a possibility of causing degradation, reduction of molecular weight and the like of the hyaluronic acid derivative, but such a problem can be avoided in the case of filtration sterilization.

The pharmaceutical agent of the present invention is a pharmaceutical preparation comprising a hyaluronic acid derivative as the substance of the present invention as an active ingredient. By taking advantage of the above-mentioned characteristics of the substance of the present invention, the pharmaceutical agent of the present invention can take an embodiment in which the substance can be extruded from an injector and the like, and is also used as a solution of the substance of the present invention dissolved in an aqueous medium. For example, a solution in which saline, phosphate buffered saline or water for injection capable of being administered to the living body is used as the solvent and which contains the substance of the present invention at a concentration of from 0.1% by weight to 10% by weight can be cited. It is preferable that this solution is not turbid but transparent.

As described above, the pharmaceutical agent of the present invention is applicable to the dust removal, removal of microorganisms, and sterilization of microorganisms by filter filtration. Removal of dust and microorganisms becomes possible by passing through a 5 μm or 0.45 μm filter, and sterilization also becomes possible by passing through a 0.22 μm filter. In addition, it is possible also to use the pharmaceutical agent of the present invention together with the substance of the present invention and a pharmaceutically acceptable carrier, within such a range that the advantage owned by the pharmaceutical agent of the present invention, namely the property to be sterilized by filtration, is not spoiled.

It is preferable that the pharmaceutical agent of the present invention prepared in this manner can be subjected to filtration sterilization and also in such a state that it has a certain degree of viscoelasticity.

It is possible to use the pharmaceutical agent of the present invention as a medicament for parenteral administration use or a medicament for topical administration use. As the embodiment of using it in the parenteral administration and topical administration, a solution prepared by dissolving the above-described substance of the present invention in an aqueous solvent is preferable, and administration methods such as injection and infusion can be preferably exemplified (according to this description, the "infusion" sometimes includes "injection"). By carrying out topical administration by infusion, side effects in the digestive organ system can be avoided. In addition, since the metabolism by the digestive organ system can also be avoided, it is possible to reduce the dose in comparison with the case of oral administration, and what is more, the problem of systemic toxicity caused by a large dose of oral administration can also be avoided.

Regarding the extrusion device to be used in injection, infusion and the like, it is possible to use implements generally used for the purpose of administering a filled medicament by extrusion, such as an injector and an infusion device.

In this connection, it is possible also to provide a kit in which a solution of the pharmaceutical agent of the present invention or the substance of the present invention is filled in an extrudable infusion device equipped with a plunger for medicament extrusion or the like. In addition, it is possible to make the kit into a medical injection kit in which a solution, prepared by dissolving the substance of the present invention in a pharmaceutically acceptable phosphate buffered saline, saline or water for injection, is filled in a syringe and sealed with a slidable plunger for medicament extrusion in such a manner. In this connection, it is possible to use a generally used device as the plunger for medicament extrusion, which is formed from an elastic body such as a rubber or a synthetic rubber and inserted into a syringe under a closely contacted state in such a manner that it can be slid. In addition, a plunger rod for extruding a medicament by carrying out pushing operation of the plunger may also be included in the kit.

Although the disease to be treated and route of administration of the pharmaceutical agent of the present invention are not particularly limited, it is possible to use it as a therapeutic agent for the purpose of treating arthritis, suppression of inflammation, suppression of pain and the like (hereinafter also referred to as "therapeutic agent of the present invention"), which is preferable. In this connection, according to this description, the "therapeutic agent" includes not only a "treating agent" but also a medicament which is used for the purpose of preventing disease or alleviation of symptoms.

Not only the therapeutic agent of the present invention has the sustained release action of anti-inflammatory drugs such as NSAIDs and the medicament delivery system action as described below, but also the effect of hyaluronic acid pharmaceutical preparations currently used in the clinical field on arthritis can also be expected at the same time, in addition to the therapeutic effect by anti-inflammatory drugs in treating arthritis.

In addition, the dose of the therapeutic agent of the present invention is not particularly limited, because it is an item which should be individually decided according to the route of administration, administration form, using purpose, and specific symptoms, age, body weight and the lie of the animal to be treated, in such a manner that its therapeutic effect is exerted most appropriately. For example, in the case of injections for human use, approximately from 1 mg to 1,000 mg, preferably approximately from 5 mg to 500 mg, more preferably approximately from 10 mg to 100 mg, per adult per once, based on a hyaluronic acid derivative can be cited. However, it is considered that strength of the medicament effect owned by the NSAIDs or DMARD used in the substance of the present invention as an active ingredient has great an influence on the therapeutic agent of the present invention, so that the range described above is not always suitable, and it is necessary to set it by taking the dose converted into the NSAIDs or DMARD single preparation into consideration. In addition, as is shown in Examples described below, different from the case in which NSAIDs single preparation is administered, the pharmaceutical agent of the present invention is present in the administered site stably and continuously, so that it is necessary to set it by also taking this point into consideration.

The site to which the therapeutic agent of the present invention is to be applied is not particularly limited, so long as it is an application site by parenteral administration, and joints are preferable among the parts, and a knee joint, a shoulder joint, a hip joint, a jaw joint and the like are particularly preferable. Especially, application to osteoarthritis of knee (OA) and rheumatoid arthritis of knee (RA) is preferable.

In this connection, when the pharmaceutical agent of the present invention is used as a therapeutic agent for arthritis, a proper concentration as joint infusions (injections) can be optionally selected as described above, and the concentration of solution is preferably from 0.3 to 3.0% by weight, more preferably from 0.5 to 1.5% by weight.

As one of the most preferable embodiments of the pharmaceutical agent of the present invention, the following construction can be cited.

NSAID:
  Compound represented by the above-described formula (2)

Spacer and Binding Mode:
  Aminoalkyl alcohol is bound with NSAID via an ester bond, bound with hyaluronic acid via an amide bond Molecular Weight of Hyaluronic Acid:
  Weight average molecular weight: 500,000 to 3,000,000

Degree of Substitution of NSAID:
  5 to 50% by mol per hyaluronic acid disaccharide unit Concentration and Solvent:
  Phosphate buffered saline having a concentration of from 0.3 to 3.0% by weight Providing Condition:
  Filled in a syringe under sterilized state.

In addition, as the NSAID, the compound represented by the above-described formula (7) is more preferable, and the compounds represented by the above-described formula (8) and the above-described formula (9) are further preferable, and diclofenac or a derivative thereof is particularly preferable. As the spacer, it is more preferably when selected from aminopropyl alcohol or aminoethyl alcohol.

As the degree of substitution, from 10 to 50% by mol per hyaluronic acid disaccharide unit is more preferable.

Also, it is most preferable when filtration through a 5 μm or 0.45 μm filter is possible, and further when filtration through a 0.22 μm filter is possible.

As shown in the examples which are described below, it is particularly suitable to use the pharmaceutical agent of the present invention as a therapeutic agent for arthritis, particularly as joint infusions for arthritis treatment. For example, when low molecular weight compounds such as NSAIDs are directly infused into joint cavity, these compounds are immediately removed into blood stream through synovium, so that a greater effect cannot be expected.

On the other hand, when a solution of an NSAIDs-introduced hyaluronic acid derivative to which NSAIDs as the substance of the present invention are introduced through a covalent bond is administered into joint cavity, NSAIDs are continuously present in the synovium tissue as is shown later in the examples, while the low molecular weight compound alone is quickly metabolized in the synovium. As is generally known, hyaluronic acid has affinity for synovium. For the reason it is considered that the pharmaceutical agent of the present invention is retained to a certain degree in the synovium under a state in which hyaluronic acid and NSAIDs are bound, and after gradually incorporated into tissues or cells, NSAIDs are released from hyaluronic acid and take the action. That is, in the case of the administration of the pharmaceutical agent of the present invention, NSAIDs are not immediately removed into blood stream, but NSAIDs are persistently present in the joint fluid and synovium, so that it shows persistent effect.

Based on this, it is preferable that the binding of hyaluronic acid with a spacer compound in the pharmaceutical agent of the present invention shows resistance to its biodegradation in comparison with the binding of NSAIDs with the spacer compound. In addition, preferred is an embodiment in which the binding site of NSAIDs with the spacer compound is not degraded in the joint cavity, but degraded in the synovium tissue after incorporated into the synovium. By changing binding modes of NSAIDs with the spacer compound and hyaluronic acid with the spacer compound, resistance to the biodegradation can be changed thereby rendering possible control of the aptness to release and the releasing ratio. For example, when hydrolysis occurring in the living body is considered, an ester bond is more susceptible against degradation than amide bond. Thus, in selecting a spacer which binds to hyaluronic acid via an aminde bond and NSAIDs via an ester bond, the ester bonds are susceptible to hydrolysis and NSAIDs are released from the substance of the present invention which has been hydrolyzed to be active. A pharmaceutical preparation for sustained release use is also possible by the pharmaceutical agent of the present invention.

In this connection, in the examples which are described below, when 2 kinds of the substance of the present invention in which hyaluronic acid was bound to a spacer compound via an amide bond and NSAIDs was bound to the spacer compound via amide bond or ester bond were respectively administered, the substance of the present invention in which NSAIDs and the spacer compound were bound via an ester bond showed more significant pain suppressing effect.

It is known that inhibition of prostaglandin production by the cyclooxigenase (COX) inhibitory activity in the target cell plays a role as the mechanism of NSAIDs which suppress inflammation and pain accompanied by arthritis. Evaluation of the substance of the present invention was carried out by using Chemiluminescent COX Inhibitor Screening Assay Kit (manufactured by Cayman) which is a method generally used for the evaluation of COX-2 inhibitory activity. As a result, the COX-2 inhibitory activity was not found in the substance 1 of the present invention, by the dose by which NSAIDs as single preparation clearly showed the COX-2 inhibitory activity and also by the dose of the substance 1 of the present invention containing an amount of NSAIDs which corresponds to the dose of the single preparation converted from NSAIDs.

This in vitro results can not be extended to the living body which is concerted by various conditions and states, however, it is easily speculated that the release of NSAIDs in the acting area by the pharmaceutical agent of the present invention is preferable.

In addition, the substance of the present invention is also useful as a base material of the drug delivery system (DDS) of NSAIDs or DMARD which, being low molecular weight compounds, are known to be difficult in effective delivery to the target site (cells) by single drug administration because of the quick metabolism in the living body. In order to obtain efficient results by reducing influence of the metabolism, it is markedly important to deliver NSAIDs or DMARD to the target cells in the form of the NSAIDs- or DMARD-introduced hyaluronic acid derivative of the present invention and to further incorporate into the cells in the same form to effect persistent presence in the target site.

The amount of a medicament effective for the treatment at the administered region can be efficiently kept by the use of the substance of the present invention, in comparison with single administration of the medicament, so that much stronger therapeutic effect can be expected with much smaller dose by oral administration. In addition, since sustained release ability and persistency of the effect can be improved, reduction of the number of times of administration and the like in the clinical use can also be expected.

EXAMPLES

The present invention is described below more specifically based on Examples. However, there is no intention to limit the technical scope of the present invention by this.

In this connection, all of the hyaluronic acid and sodium hyaluronate used in the following Examples were purchased from Seikagaku Corporation.

Hereinafter, as the phosphate buffered saline (PBS), 5 mM PBS was used in the following Examples, unless otherwise indicated.

Test Example

Filter Pass Through Test

PBS in which each substance to be tested was dissolved to a concentration of 1.0% by weight was prepared. At a temperature of 24° C. under pressure of 5.0 kg/cm$^2$, each solution of the substances to be tested prepared in the following examples was passed through a 0.45 μm porous filter (25 mm in diameter), and the passed amount (ml) per 1 minute was measured A case in which 2 ml or more was passed is shown by "A", and a case in which less than 2 ml was passed by "B", and a case in which none passed by "C".

Production Examples

Reference Example 1

Synthesis of t-butoxycarbonyl-aminopropanol (Boc-NH(CH$_2$)$_3$OH) (Boc-aminopropanol)

In 10 ml of dichloromethane, 1.542 g (20.5 mmol) of aminopropanol was dissolved, and 10 ml of a 4.484 g (20.5 mmol) di-t-butyl dicarbonate (Boc$_2$O)/dichloromethane solution was slowly added dropwise thereto under ice-cooling. Thereafter, the reaction solution was returned to room temperature and stirred for 2 hours and 40 minutes, disappearance of the starting materials was confirmed by thin layer chromatography (TLC), and then dichloromethane was evaporated under reduced pressure. The reaction quantitatively progressed, and an oily substance was obtained at a yield of 3.92 g. The structure was identified by $^1$H-NMR (CDCl$_3$).

$^1$H-NMR (500 MHz, CDCl$_3$) δ (ppm)=1.46 (9H, s, Boc), 1.66 (2H, quant, —NHCH$_2$C$\underline{H}_2$CH$_2$O—), 3.27 (3H, m, —NHC$\underline{H}_2$CH$_2$CH$_2$O—), 3.66 (2H, m, —NHCH$_2$CH$_2$C$\underline{H}_2$O—), 4.91 (1H, br, CH$_2$O$\underline{H}$)

Example 1

Synthesis of Aminopropanol-ketoprofen Hydrochloride

1) Synthesis of Boc-aminopropanol-ketoprofen

In 14 ml of dichloromethane, 2.371 g (13.5 mmol) of Boc-aminopropanol and 3.441 g (13.5 mmol) of ketoprofen (manufactured by Tokyo Kasei Kogyo) were dissolved, and 323 mg (2.6 mmol) of 4-dimethylaminopyridine (DMAP) and 2.833 g (14.8 mmol) of water-soluble carbodiimide hydrochloride (WSCI.HCl)/14 ml dichloromethane were added thereto in this order under ice-cooling. After returning to room temperature and stirring overnight, dichloromethane was evaporated under reduced pressure, and ethyl acetate was added thereto, followed by separation by washing with 5% citric acid twice, water, 5% sodium hydrogen carbonate twice, water and saturated brine consecutively. After dehydration drying with sodium sulfate, ethyl acetate was evaporated under reduced pressure to give 5.430 g of the titled compound (yield 98%). The structure was identified by $^1$H-NMR (CDCl$_3$).

$^1$H-NMR (500 MHz, CDCl$_3$) δ (ppm)=1.43 (9H, s, Boc), 1.54 (3H, d, —OCOCH(C$\underline{H}_3$)—), 1.77 (2H, quant, —NHCH$_2$C$\underline{H}_2$CH$_2$O—), 3.09 (2H, m, —NH C$\underline{H}_2$CH$_2$CH$_2$O—), 3.82 (1H, q, —OCOC$\underline{H}$(CH$_3$)—), 4.15 (2H, m, —NHCH$_2$CH$_2$C$\underline{H}_2$O—), 4.69 (1H, br, —N$\underline{H}$CH$_2$—), 7.42-7.83 (9H, m, Aromatic H)

2) Synthesis of Aminopropanol-ketoprofen Hydrochloride

Under ice-cooling, 20 ml of 4 M hydrochloric acid/ethyl acetate was added to 5.330 g (12.95 mmol) of the Boc-aminopropanol-ketoprofen obtained above, followed by stirring under ice-cooling for 15 minutes and at room temperature for 2 hours. After confirming disappearance of Boc-aminopropanol-ketoprofen by TLC, the solvent was evaporated under reduced pressure, and the residue was subjected twice to decantation with diethyl ether. Thereafter, the residue was dried under reduced pressure to quantitatively give the titled substance at a yield of 4.569 g. The structure was identified by $^1$H-NMR (CDCl$_3$).

$^1$H-NMR (500 MHz, CDCl$_3$) δ (ppm)=1.50 (5H, d, —OCOCH(C$\underline{H}_3$)—), 2.08 (2H, m, —NHCH$_2$C$\underline{H}_2$CH$_2$O—), 3.04 (2H, br, —NHC$\underline{H}_2$CH$_2$CH$_2$O—), 3.82 (1H, q, —OCO C$\underline{H}$(CH$_3$)—), 4.16 (2H, m, —NHCH$_2$CH$_2$C$\underline{H}_2$O—), 7.36-7.80 (9H, m, Aromatic H), 8.20 (br, $\underline{H}_3$N$^+$CH$_2$—)

Example 2

Synthesis of Aminopropanol-ketoprofen-Introduced Sodium Hyaluronate

In 22.5 ml water/22.5 ml dioxane, 200 mg (0.5 mmol/disaccharide unit) of sodium hyaluronate having a weight average molecular weight of 900,000 was dissolved, and then 0.25 ml of 2 M aqueous hydroxysuccinimide (HOSu) solution, 0.25 ml of 1 mol/l aqueous WSCI.HCl solution and 0.5 ml of the 0.5 M aqueous solution of aminopropanol-ketoprofen hydrochloride obtained in Example 1 were added thereto in this order, followed by stirring overnight. To the reaction solution, 3 ml of 5% aqueous sodium hydrogen carbonate solution was added, followed by stirring for 3 hours and 20 minutes. After neutralizing the reaction solution by adding 86 μl of 50% acetic acid, 800 mg of sodium chloride was added thereto, followed by stirring. The mixture was precipitated by adding 200 ml of ethanol, and the precipitate was washed twice with 80% ethanol, twice with ethanol and twice with diethyl ether and dried at room temperature overnight under reduced pressure to give 198 mg portion of a white solid. The degree of substitution of ketoprofen was 15.5% by HPLC analysis. The thus obtained substance was dissolved in PBS to a concentration of 1.0% by weight to prepare a solution. The solution was a colorless and transparent liquid, and the result of its filter pass through test was "A".

Example 3

Synthesis of Aminopropanol-ketoprofen-Introduced Sodium Hyaluronate

In 45 ml water/45 ml dioxane, 400 mg (1.0 mmol/disaccharide unit) of hyaluronic acid having a weight average molecular weight of 900,000 was dissolved, and then 1.66 mmol/1 ml water of HOSu, 0.83 mmol/1 ml water of WSCI·HCl and 0.83 mmol/4 ml water of aminopropanol-ketoprofen hydrochloride obtained in Example 1 were added thereto in this order, followed by stirring overnight. To the reaction solution, 300 mg/1 ml water of sodium hydrogen carbonate was added, followed by stirring for 3 hours and 10 minutes. After neutralizing the reaction solution by adding 86 µl of acetic acid, 400 mg of sodium chloride was added thereto, followed by stirring. The mixture was precipitated by adding 300 ml of ethanol, and the precipitate was washed twice with 80% ethanol, twice with ethanol and twice with diethyl ether and dried at room temperature overnight under reduced pressure to give 246 mg of a white solid. The degree of substitution of ketoprofen was 26.3% by HPLC analysis. The thus obtained substance was dissolved in PBS to a concentration of 1.0% by weight to prepare a solution. The solution was a colorless and transparent liquid, and the result of its filter pass through test was "A".

Example 4

Synthesis of Aminopropanol-naproxen Hydrochloride

1) Synthesis of Boc-aminopropanol-naproxen

In 2 ml of dichloromethane, 350 mg (2 mmol) of Boc-aminopropanol and 462 g (2 mmol) of naproxen (manufactured by Wako Pure Chemical Industries) were dissolved, and 48 mg (0.4 mmol) of DMAP and 422 g of WSCI·HCl (2.2 mmol)/2 ml dichloromethane were added thereto in this order under ice-cooling. After returning to room temperature and stirring for 4 hours and 50 minutes, dichloromethane was evaporated under reduced pressure, and ethyl acetate was added thereto, followed by separation by washing with 5% citric acid twice, water, 5% sodium hydrogen carbonate twice, water and saturated brine consecutively. After dehydration drying with sodium sulfate, ethyl acetate was evaporated under reduced pressure to give 720 mg of white crystal of the titled compound (yield 93%). The structure was identified by $^1$H-NMR (CDCl$_3$).

$^1$H-NMR (500 MHz, CDCl$_3$) δ (ppm)=1.42 (9H, s, Boc), 1.58 (3H, d, —OCOCH(C$\underline{H}_3$)—), 1.75 (2H, quant, —NHCH$_2$C$\underline{H}_2$CH$_2$O—), 3.07 (2H, m, —NHC$\underline{H}_2$CH$_2$CH$_2$O—), 3.85 (1H, q, —OCOC$\underline{H}$(CH$_3$)—), 3.91 (3H, s, —OCH$_3$), 4.13 (2H, m, —NHCH$_2$CH$_2$C$\underline{H}_2$O—), 4.63 (1H, br, —N$\underline{H}$CH$_2$—), 7.09-7.75 (6H, m, Aromatic H)

2) Synthesis of Aminopropanol-naproxen Hydrochloride

In 1 ml of dichloromethane, 684 mg (1.76 mmol) of the Boc-aminopropanol-naproxen obtained above was dissolved, and 2 ml of 4 M hydrochloric acid/ethyl acetate was added thereto under ice-cooling, followed by stirring under ice-cooling for 20 minutes and at room temperature for 1 hour. After confirming disappearance of Boc-aminopropanol-naproxen by TLC, and diethyl ether was added thereto, followed by decantation three times. Thereafter, the residue was dried under reduced pressure to quantitatively give the titled substance at a yield of 564 mg. The structure was identified by $^1$H-NMR (CDCl$_3$).

$^1$H-NMR (500 MHz, CDCl$_3$+CD$_3$OD) δ (ppm)=1.57 (3H, d, —OCOCH(C$\underline{H}_3$)—), 2.02 (2H, quant, —NHCH$_2$C$\underline{H}_2$CH$_2$O—), 2.88 (2H, m, —NHC$\underline{H}_2$CH$_2$CH$_2$O—), 3.87 (1H, q, —OCOC$\underline{H}$(CH$_3$)—), 3.90 (3H, s, —OCH$_3$), 4.17 (2H, m, —NHCH$_2$CH$_2$C$\underline{H}_2$O—), 7.08-7.73 (6$\underline{H}$, m, Aromatic H), 8.10 (br, $\underline{H}_3$N$^+$CH$_2$—)

Example 5

Synthesis of Aminopropanol-naproxen-Introduced Sodium Hyaluronate

In 11.5 ml water/11.5 ml dioxane, 100 mg (0.25 mmol/disaccharide unit) of sodium hyaluronate having a weight average molecular weight of 900,000 was dissolved, and then HOSu (0.2 mmol)/0.1 ml water, WSCI·HCl (0.1 mmol)/0.1 ml water and aminopropanol-naproxen hydrochloride obtained in Example 4 (0.1 mmol)/0.3 ml water were added thereto in this order, followed by stirring overnight. To the reaction solution, 1.5 ml of 5% aqueous sodium hydrogen carbonate solution was added, followed by stirring for 3 hours and 35 minutes. After neutralizing the reaction solution by adding 43 µl of 50% acetic acid, 500 mg of sodium chloride was added thereto, followed by stirring. The mixture was precipitated by adding 50 ml of ethanol, and the precipitate was washed twice with 80% ethanol, twice with ethanol and with diethyl ether and dried at room temperature overnight under reduced pressure to give 95 mg of a white solid. The degree of substitution of naproxen was 13.1% by HPLC analysis. The thus obtained substance was dissolved in PBS to a concentration of 1.0% by weight to prepare a solution. The solution was a colorless and transparent liquid, and the result of its filter pass through test was "A".

Example 6

Synthesis of Aminopropanol-ibuprofen Hydrochloride

1) Synthesis of Boc-aminopropanol-ibuprofen

In 2 ml of dichloromethane, 352 mg (2 mmol) of Boc-aminopropanol and 412 g (2 mmol) of ibuprofen (manufactured by Wako Pure Chemical Industries) were dissolved, and 48 mg (0.4 mmol) of DMAP and 423 g (2.2 mmol) of WSCI·HCl/2 ml dichloromethane were added thereto in this order under ice-cooling. After returning to room temperature and stirring overnight, and ethyl acetate was added thereto, followed by separation by washing with 5% citric acid twice, water, 5% sodium hydrogen carbonate twice, water and saturated brine consecutively. After dehydration drying with sodium sulfate, ethyl acetate was evaporated under reduced pressure to give 665 mg of the titled compound (yield 91%). The structure was identified by $^1$H-NMR (CDCl$_3$).

$^1$H-NMR (500 MHz, CDCl$_3$) δ (ppm)=0.88 (6H, d, —CH(C$\underline{H}_3$)$_2$), 1.44 (9H, s, Boc), 1.49 (3H, d, —OCOCH(C$\underline{H}_3$)—), 1.75 (2H, m, —NHCH$_2$C$\underline{H}_2$CH$_2$O—), 1.85 (1H, m, —CH$_2$C$\underline{H}$(CH$_3$)$_2$), 2.45 (2H, d, —C$\underline{H}_2$CH(CH$_3$)$_2$), 3.05 (2H, m, —NHC$\underline{H}_2$CH$_2$CH$_2$O—), 3.69 (1H, q, —OCOC$\underline{H}$(CH$_3$)—), 4.13 (2H, t, —NHCH$_2$CH$_2$C$\underline{H}_2$O—), 4.63 (1H, br, —N$\underline{H}$CH$_2$—), 7.07-7.21 (4H, m, Aromatic H)

2) Synthesis of Aminopropanol-ibuprofen Hydrochloride

In 1 ml of dichloromethane, 636 mg (1.75 mmol) of the Boc-aminopropanol-ibuprofen obtained above was dissolved, and 4 ml of 4 M hydrochloric acid/ethyl acetate was added thereto under ice-cooling, followed by stirring under ice-cooling for 10 minutes and at room temperature for 3 hours. After confirming disappearance of Boc-aminopropanol-ibuprofen by TLC, diethyl ether was added thereto, followed by decantation three times. Thereafter, the residue was dried under reduced pressure to give the titled substance at a yield of 406 mg (77%). The structure was identified by $^1$H-NMR (CDCl$_3$).

$^1$H-NMR (500 MHz, CDCl$_3$) δ (ppm)=0.89 (6H, d, —CH(CH$_3$)$_2$), 1.47 (3H, d, —OCOCH(CH$_3$)—), 1.83 (1H, m, —CH$_2$CH(CH$_3$)$_2$), 2.08 (2H, quant, —NHCH$_2$CH$_2$CH$_2$O—), 2.44 (2H, d, —CH$_2$CH(CH$_3$)$_2$), 3.01 (2H, t, —NHCH$_2$CH$_2$CH$_2$O—), 3.71 (1H, q, —OCOCH(CH$_3$)—), 4.11-4.27 (2H, m, —NHCH$_2$CH$_2$CH$_2$O—), 7.06-7.20 (4H, m, Aromatic H), 8.25 (br, H$_3$N$^+$CH$_2$—)

Example 7

Synthesis of Aminopropanol-ibuprofen-Introduced Sodium Hyaluronate

In 11.5 ml water/11.5 ml dioxane, 100 mg (0.25 mmol/disaccharide unit) of sodium hyaluronate having a weight average molecular weight of 900,000 was dissolved, and then HOSu (0.2 mmol)/0.1 ml water, WSCI.HCl (0.1 mmol)/0.1 ml water and the aminopropanol-ibuprofen hydrochloride obtained in Example 6 (0.1 mmol)/0.3 ml water were added thereto in this order, followed by stirring overnight. To the reaction solution, 1.5 ml of 5% aqueous sodium hydrogen carbonate solution was added, followed by stirring for 3 hours and 35 minutes. After neutralizing the reaction solution by adding 43 μl of 50% acetic acid, 500 mg of sodium chloride was added thereto, followed by stirring. The mixture was precipitated by adding 50 ml of ethanol, and the precipitate was washed twice with 80% ethanol, twice with ethanol and with diethyl ether and dried at room temperature overnight under reduced pressure to give 93 mg of a white solid. The degree of substitution of ibuprofen was 16.4% by HPLC analysis. The thus obtained substance was dissolved in PBS to a concentration of 1.0% by weight to prepare a solution. The solution was a colorless and transparent liquid, and the result of its filter pass through test was "A".

Example 8

Synthesis of Aminopropanol-flurbiprofen Hydrochloride

1) Synthesis of Boc-aminopropanol-flurbiprofen

In 2 ml of dichloromethane, 352 mg (2 mmol) of Boc-aminopropanol and 489 g (2 mmol) of flurbiprofen (manufactured by Wako Pure Chemical Industries) were dissolved, and 48 mg (0.4 mmol) of DMAP and 423 g (2.2 mmol) of WSCI.HCl/2 ml dichloromethane were added thereto in this order under ice-cooling. After returning to room temperature and stirring overnight, ethyl acetate was added thereto, followed by separation by washing with 5% citric acid twice, water, 5% sodium hydrogen carbonate twice, water and saturated brine consecutively. After dehydration drying with sodium sulfate, ethyl acetate was evaporated under reduced pressure to give 753 mg of the titled compound (yield 94%). The structure was identified by $^1$H-NMR (CDCl$_3$).

$^1$H-NMR (500 MHz, CDCl$_3$) δ (ppm)=1.26 (9H, s, Boc), 1.54 (3H, d, —OCOCH(CH$_3$)—), 1.80 (2H, quant, —NHCH$_2$CH$_2$CH$_2$O—), 3.13 (2H, m, —NHCH$_2$CH$_2$CH$_2$O—), 3.76 (1H, q, —OCOCH(CH$_3$)—), 4.15 (2H, m, —NHCH$_2$CH$_2$CH$_2$O—), 4.66 (1H, br, —NHCH$_2$—), 7.10-7.55 (9H, m, Aromatic H)

2) Synthesis of Aminopropanol-flurbiprofen Hydrochloride

In 1 ml of dichloromethane, 720 mg (1.79 mmol) of the Boc-aminopropanol-flurbiprofen obtained above was dissolved, and 4 ml of 4 M hydrochloric acid/ethyl acetate was added thereto under ice-cooling, followed by stirring under ice-cooling for 3 minutes and at room temperature for 3 hours and 10 minutes. After confirming disappearance of Boc-aminopropanol-flurbiprofen by TLC, diethyl ether was added thereto, followed by decantation twice. Thereafter, the residue was dried under reduced pressure to give the titled substance at a yield of 352 mg (94%). The structure was identified by $^1$H-NMR (CDCl$_3$).

$^1$H-NMR (500 MHz, CDCl$_3$) δ (ppm)=1.51 (3H, d, —OCOCH(CH$_3$)—), 2.10 (2H, quant, —NHCH$_2$CH$_2$CH$_2$O—), 3.05 (2H, t, —NHCH$_2$CH$_2$CH$_2$O—), 3.76 (1H, q, —OCOCH(CH$_3$)—), 4.13-4.29 (2H, m, —NHCH$_2$CH$_2$CH$_2$O—), 7.07-7.53 (9H, m, Aromatic H), 8.27 (br, H$_3$N$^+$CH$_2$—)

Example 9

Synthesis of Aminopropanol-flurbiprofen-Introduced Sodium Hyaluronate

In 11.5 ml water/11.5 ml dioxane, 100 mg (0.25 mmol/disaccharide unit) of sodium hyaluronate having a weight average molecular weight of 900,000 was dissolved, and then HOSu (0.2 mmol)/0.1 ml water, WSCI.HCl (0.1 mmol)/0.1 ml water and the aminopropanol-flurbiprofen hydrochloride obtained in Example 8 (0.1 mmol)/0.3 ml water were added thereto in this order, followed by stirring overnight. To the reaction solution, 1.5 ml of 5% aqueous sodium hydrogen carbonate solution was added, followed by stirring for 3 hours and 35 minutes. After neutralizing the reaction solution by adding 43 μl of 50% acetic acid, 500 mg of sodium chloride was added thereto, followed by stirring. The mixture was precipitated by adding 50 ml of ethanol, and the precipitate was washed twice with 80% ethanol, twice with ethanol and with diethyl ether and dried at room temperature overnight under reduced pressure to give 94 mg of a white solid. The degree of substitution of flurbiprofen was 21.1% by HPLC analysis. The thus obtained substance was dissolved in PBS to a concentration of 1.0% by weight to prepare a solution. The solution was a colorless and transparent liquid, and the result of its filter pass through test was "A".

Example 10

Synthesis of Aminopropanol-acetylsalicylic Acid Hydrochloride

1) Synthesis of Boc-aminopropanol-acetylsalicylic Acid

Boc-aminopropanol (2.11 mmol), acetylsalicylic acid (2.11 mmol) (manufactured by Wako Pure Chemical Industries) and DMAP (0.42 mmol) were dissolved in dichloromethane-dioxane (2:1, 6 ml), and WSCI.HCl (2.35 mmol) was added thereto under ice-cooling. After returning to room temperature and stirring overnight, ethyl acetate was added thereto, followed by separation by washing with 5% citric acid, 5% sodium hydrogen carbonate and saturated brine consecutively. After dehydration drying with sodium sulfate, ethyl acetate was evaporated under reduced pressure. The thus obtained residue was purified by silica gel column chromatography (hexane:ethyl acetate=3:1, 0.5% triethylamine) to give the titled compound (298.0 mg, yield 48%). The structure was identified by $^1$H-NMR (CDCl$_3$).

$^1$H-NMR (500 MHz, CDCl$_3$) δ (ppm)=1.44 (9H, s, Boc), 1.90-1.96 (2H, m, BocHNCH$_2$CH$_2$CH$_2$O—), 2.35 (3H, s, —COCH$_3$), 3.24-3.28 (2H, m, BocHNCH$_2$CH$_2$CH$_2$O—), 4.35 (2H, t, BocHNCH$_2$CH$_2$CH$_2$O—), 4.78 (1H, s, NH), 7.11 (1H, dd, Aromatic), 7.32 (1H, td, Aromatic), 7.55-7.59 (1H, m, Aromatic), 8.01 (1H, dd, Aromatic)

2) Synthesis of Aminopropanol-acetylsalicylic Acid Hydrochloride

The Boc-aminopropanol-acetylsalicylic acid obtained above (0.814 mmol) was dissolved in dichloromethane (1 ml), and 4 N hydrochloric acid/ethyl acetate (3 ml) was added thereto under ice-cooling, followed by stirring for 2 hours. After confirming disappearance of Boc-aminopropanol-acetylsalicylic acid by TLC, diethyl ether was added thereto. The thus formed precipitate was centrifuged, and the supernatant was subjected to decantation. The thus obtained precipitate was dried under reduced pressure to give 213.9 mg (yield 96%) of the titled compound. The structure was identified by $^1$H-NMR (CDCl$_3$).

$^1$H-NMR (500 MHz, CDCl$_3$) δ (ppm)=2.22 (2H, t, H$_2$NCH$_2$CH$_2$CH$_2$O—), 2.35 (3H, s, —COCH$_3$), 3.13 (2H, t, H$_2$NCH$_2$CH$_2$CH$_2$O—), 4.41 (2H, t, H$_2$NCH$_2$CH$_2$CH$_2$O—), 7.09 (1H, dd, Aromatic), 7.31 (1H, dt, Aromatic), 7.56 (1H, dt, Aromatic), 7.99 (1H, dd, Aromatic)

Example 11

Synthesis of Aminopropanol-acetylsalicylic Acid-Introduced Sodium Hyaluronate

Hyaluronic acid (100 mg), 0.25 mmol/disaccharide unit having a weight average molecular weight of 900,000 was dissolved in water-dioxane (1:1), and 2 mol/L HOSu (0.1 ml), 1 mol/L WSCI.HCl (0.1 ml) and a water-dioxane (1:1) solution (2 ml) of the aminopropanol-acetylsalicylic acid hydrochloride obtained above in Example 10 were added thereto in this order, followed by stirring overnight. To the reaction solution, 5% aqueous sodium hydrogen carbonate solution (1.5 ml) was added, followed by stirring for 3 hours. After neutralizing the reaction solution by adding 50% aqueous acetic acid solution (43 μl), sodium chloride (0.4 g) was added thereto, followed by stirring. The mixture was precipitated by adding ethanol (100 ml), and the precipitate was washed with 80% aqueous ethanol solution, ethanol and diethyl ether, twice for each, consecutively. Thereafter, the precipitate was dried under reduced pressure to give the titled compound (97.7 mg). The degree of substitution of acetylsalicylic acid was 13.5% when measured by an absorptiometric method. The thus obtained substance was dissolved in PBS to a concentration of 1.0% by weight to prepare a solution. The solution was a colorless and transparent liquid, and the result of its filter pass through test was "A".

Example 12

Synthesis of Aminopropanol-felbinac Hydrochloride

1) Synthesis of Boc-aminopropanol-felbinac

Boc-aminopropanol (2.04 mmol), felbinac (2.04 mmol) (manufactured by Aldrich Chem. Co.) and DMAP (0.41 mmol) were dissolved in dioxane (7 ml) and then a dioxane-dichloromethane (3:4) solution (7 ml) of WSCI.HCl (2.35 mmol) was added thereto under ice-cooling. The reaction solution was clarified by adding dimethylformamide (DMF) (3 ml) and then returned to room temperature, followed by stirring overnight. Ethyl acetate was added thereto, followed by separation by washing with 5% aqueous citric acid solution, 5% aqueous sodium hydrogen carbonate solution and saturated brine consecutively. After dehydration drying with sodium sulfate, the solvent was evaporated under reduced pressure. The thus obtained residue was purified by silica gel column chromatography (hexane:ethyl acetate=3:1, 0.5% triethylamine) to give the titled compound (623.0 mg, yield 83%). The structure was identified by $^1$H-NMR (CDCl$_3$).

$^1$H-NMR (500 MHz, CDCl$_3$) δ (ppm)=1.44 (9H, s, Boc), 1.80-1.85 (2H, m, BocHNCH$_2$CH$_2$CH$_2$O—), 3.15-3.19 (2H, m, BocHNCH$_2$CH$_2$CH$_2$O—), 3.67 (2H, s, PhCH$_2$—), 4.18 (2H, t, BocHNCH$_2$CH$_2$CH$_2$O—), 4.67 (1H, s, NH), 7.34-7.59 (9H, m, Aromatic)

2) Synthesis of Aminopropanol-felbinac Hydrochloride

The Boc-aminopropanol-felbinac obtained above (1.69 mmol) was dissolved in dichloromethane (1 ml), and 4 N hydrochloric acid/ethyl acetate (3 ml) was added thereto under ice-cooling. The mixture was returned to room temperature, followed by stirring for 2 hours. After confirming disappearance of Boc-aminopropanol-felbinac by TLC, diethyl ether was added thereto and the thus formed precipitate was centrifuged. The thus obtained precipitate was subjected to three times of decantation with diethyl ether and then dried under reduced pressure to give the titled compound (511.7 mg, yield 99%). The structure was identified by $^1$H-NMR (CDCl$_3$:CD$_3$OD=1:1).

$^1$H-NMR (500 MHz, CDCl$_3$:CD$_3$OD=1:1) δ (ppm)=1.98-2.04 (2H, m, H$_2$NCH$_2$CH$_2$CH$_2$O—), 2.95 (2H, t, H$_2$NCH$_2$CH$_2$CH$_2$O—), 3.73 (2H, s, -PhCH$_2$—), 4.23 (2H, t, H$_2$NCH$_2$CH$_2$CH$_2$O—), 7.33-7.59 (9H, m, Aromatic)

Example 13

Synthesis of Aminopropanol-felbinac-Introduced Hyaluronic Acid

Hyaluronic acid (200 mg) 0.5 mmol/disaccharide unit having a weight average molecular weight of 900,000 was dissolved in water-dioxane (1:1, 45 ml), and 2 mol/L of HOSu (0.25 ml), 1 mol/L of WSCI.HCl (0.25 ml) and the 0.5 M aqueous solution of felbinac propanolamine hydrochloride obtained in Example 12 (0.5 ml) were added thereto in this order, followed by stirring overnight. To the reaction solution, 5% aqueous sodium hydrogen carbonate solution (3 ml) was added, followed by stirring for 3 hours. After neutralizing the reaction solution by adding 50% aqueous acetic acid solution (86 μl), sodium chloride (0.8 g) was added thereto, followed by stirring. Ethanol (200 ml) was added thereto, followed by stirring. The thus formed precipitate was centrifuged, and the resulting precipitate was washed with 80% aqueous ethanol solution, ethanol and diethyl ether consecutively, twice for each. The precipitate was dried at room temperature overnight under reduced pressure to give the titled compound (205.1 mg). The degree of substitution of felbinac was 27.8% by HPLC analysis. The thus obtained substance was dissolved in PBS to a concentration of 1.0% by weight to prepare a solution. The solution was a colorless and transparent liquid, and the result of its filter pass through test was "A".

Example 14

Synthesis of Aminopropanol-fenbufen Hydrochloride

1) Synthesis of Boc-aminopropanol-fenbufen

Boc-aminopropanol (2.18 mmol), fenbufen (2.18 mmol) (manufactured by ICN Biochemicals Inc.) and DMAP (0.44 mmol) were dissolved in DMF-dichloromethane (5:3, 8 ml), and dichloromethane solution (5 ml) of WSCI.HCl (2.48 mmol) was added thereto under ice-cooling. After gradually returning the reaction temperature to room temperature, the mixture was stirred overnight. Ethyl acetate was added thereto, followed by separation by washing with 5% aqueous citric acid solution, 5% aqueous sodium hydrogen carbonate solution and saturated brine consecutively. After dehydration drying with sodium sulfate, the solvent was evaporated under reduced pressure. The thus obtained residue was purified by silica gel column chromatography (chloroform:ethyl acetate=40:1, 0.5% triethylamine) to give the titled compound (747.8 mg, yield 83%). The structure was identified by $^1$H-NMR (CDCl$_3$).

$^1$H-NMR (500 MHz, CDCl$_3$) δ (ppm)=1.44 (9H, s, Boc), 1.82-1.87 (2H, m, BocHNCH$_2$CH$_2$CH$_2$O—), 2.79 (2H, t, —COC$_2$H$_4$CO—), 3.20-3.24 (2H, m, BocHNCH$_2$CH$_2$CH$_2$O—), 3.36 (2H, t, —COC$_2$H$_4$CO—) 4.19 (2H, t, BocHNCH$_2$CH$_2$CH$_2$O—), 4.76 (1H, s, NH), 7.39-7.64 (5H, m, Aromatic), 7.70 (2H, td, Aromatic), 8.06 (2H, td, Aromatic)

2) Synthesis of Aminopropanol-fenbufen Hydrochloride

The Boc-aminopropanol-fenbufen obtained above (1.82 mmol) was dissolved in dichloromethane (4 ml), and under ice-cooling, 4 N hydrochloric acid ethyl acetate solution (4 ml) was added thereto, and then the mixture was gradually returned to room temperature and stirred for 90 minutes. Precipitation of white precipitate was observed just after the commencement of the reaction. After confirming disappearance of Boc-aminopropanol-fenbufen by TLC, diethyl ether was added to the reaction solution, and the resulting white precipitate was centrifuged. The precipitate was washed three times with diethyl ether and then dried under reduced pressure to give the titled compound (621.4 mg, yield 98%). The structure was identified by $^1$H-NMR (CDCl$_3$:CD$_3$OD=1:1).

$^1$H-NMR (500 MHz, CDCl$_3$:CD$_3$OD=1:1) δ (ppm)=2.01-2.07 (2H, m, H$_2$NCH$_2$CH$_2$CH$_2$O—), 2.79 (2H, t, —COC$_2$H$_4$CO—), 3.05 (2H, t, H$_2$NCH$_2$CH$_2$CH$_2$O—), 3.44 (2H, t, —COC$_2$H$_4$CO—), 4.26 (2H, t, H$_2$NCH$_2$CH$_2$CH$_2$O—), 7.41-7.50 (3H, m, Aromatic), 7.66 (dd, 2H, Aromatic), 7.75 (d, 2H, Aromatic), 8.08 (d, 2H, Aromatic)

Example 15

Synthesis of Aminopropanol-fenbufen-Introduced Hyaluronic Acid

Hyaluronic acid (200 mg) 0.5 mmol/disaccharide unit having a weight average molecular weight of 900,000 was dissolved in water-dioxane (1:1, 45 ml), and then 2 mol/L HOSu (0.25 ml), 1 mol/L WSCI.HCl (0.25 ml) and a water-dioxane (25:8) solution (0.66 ml) of the aminopropanol-fenbufen hydrochloride obtained in Example 14 were added thereto, followed by stirring overnight. To the reaction solution, 5% aqueous sodium hydrogen carbonate solution (3 ml) was added, followed by stirring for 3 hours. After neutralizing by adding 50% aqueous acetic acid solution (86 μl), sodium chloride (0.8 g) was added thereto, followed by stirring. Ethanol (200 ml) was added thereto, followed by stirring. The thus formed precipitate was centrifuged, and the thus obtained precipitate was washed with 80% aqueous ethanol solution, ethanol and diethyl ether, twice for each. The precipitate was dried under reduced pressure to give the titled compound (214.1 mg). The degree of substitution of fenbufen was 23.8% by HPLC analysis. The thus obtained substance was dissolved in PBS to a concentration of 1.0% by weight to prepare a solution. The solution was a colorless and transparent liquid, and the result of its filter pass through test was "A".

Example 16

Synthesis of Aminopropanol-mefenamic Acid Hydrochloride

1) Synthesis of Boc-aminopropanol-mefenamic Acid

Boc-aminopropanol (0.616 mmol), mefenamic acid (0.620 mmol) (manufactured by Wako Pure Chemical Industries) and DMAP (0.126 mmol) were dissolved in dichloromethane (3 ml), and a dichloromethane solution (1.5 ml) of WSCI.HCl (0.758 mmol) was added thereto, under ice-cooling. After gradually returning the reaction temperature to room temperature, the mixture was stirred overnight. The reaction solution was again ice-cooled, and a dichloromethane solution (1 ml) of WSCI.HCl (0.207 mmol) was added thereto, followed by stirring for 5 hours while gradually returning to room temperature. Ethyl acetate was added to the reaction solution, and the mixture was washed with 5% aqueous citric acid solution, 5% aqueous sodium hydrogen carbonate solution and saturated brine consecutively. After dehydration drying with sodium sulfate, the solvent was evaporated under reduced pressure. The thus obtained residue was purified by silica gel column chromatography (hexane:ethyl acetate=6:1, 0.5% triethylamine) to give the titled compound (190.4 mg, yield 78%). The structure was identified by $^1$H-NMR (CDCl$_3$).

$^1$H-NMR (500 MHz, CDCl$_3$) δ (ppm)=1.45 (9H, s, Boc), 1.96-2.01 (2H, m, BocHNCH$_2$CH$_2$CH$_2$O—), 2.18 (3H, s, Ph CH$_3$), 2.33 (3H, s, PhCH$_3$), 3.31-3.32 (2H, m, BocHN CH$_2$CH$_2$CH$_2$O—), 4.38 (2H, t, BocHNCH$_2$CH$_2$CH$_2$O—), 4.78 (1H, s, NH), 6.64-6.67 (1H, m, Aromatic), 6.74 (1H, dd, Aromatic), 7.02-7.26 (4H, m, Aromatic), 7.94 (1H, dd, Aromatic), 9.24 (1H, s, -PhNHPh-)

2) Synthesis of Aminopropanol-mefenamic Acid Hydrochloride

The Boc-aminopropanol-mefenamic acid obtained above (0.462 mmol) was dissolved in dichloromethane (0.5 ml), and 4 N hydrochloric acid/ethyl acetate (1.5 ml) was added thereto under ice-cooling, followed by stirring for 3 hours. After confirming disappearance of Boc-aminopropanol-mefenamic acid by TLC, diethyl ether was added to the reaction solution, and the thus formed precipitate was centrifuged. The thus obtained precipitate was washed with diethyl ether and then dried under reduced pressure to give the titled compound (154.4 mg, qu.). The structure was identified by H-NMR (CDCl$_3$).

$^1$H-NMR (500 MHz, CDCl$_3$) δ (ppm)=2.16 (3H, s, Ph CH$_3$), 2.25-2.30 (2H, m, H$_2$NCH$_2$CH$_2$CH$_2$O—), 2.31 (3H, s, PhCH$_3$), 3.20 (2H, t, H$_2$NCH$_2$CH$_2$CH$_2$O—), 4.44 (2H, t, H$_2$NCH$_2$CH$_2$CH$_2$O—), 6.63-6.66 (1H, m, Aromatic), 6.70-

6.72 (1H, dd, Aromatic), 7.02 (1H, d, Aromatic), 7.09 (1H, t, Aromatic), 7.14 (1H, d, Aromatic), 7.22-7.25 (1H, m, Aromatic), 7.92 (1H, dd, Aromatic), 9.17 (1H, s, -PhNHPh-)

Example 17

Synthesis of Aminopropanol-mefenamic Acid-Introduced Hyaluronic Acid

Hyaluronic acid (100 mg) 0.25 mmol/disaccharide unit having a weight average molecular weight of 900,000 was dissolved in water-dioxane (1:1, 22.5 ml), and 2 mol/L HOSu (0.1 ml), 1 mol/L WSCI.HCl (0.1 ml) and a water-dioxane (1:1) solution (2 ml) of the aminopropanol-mefenamic acid hydrochloride (0.10 mmol) obtained in Example 16 were added thereto in this order, followed by stirring overnight. To the reaction solution, 5% aqueous sodium hydrogen carbonate solution (1.5 ml) was added, followed by stirring for 4 hours. After neutralizing by adding 50% aqueous acetic acid solution (43 μl), sodium chloride (0.4 g) was added thereto, followed by stirring. Ethanol (100 ml) was added thereto, followed by stirring, and the thus formed precipitate was centrifuged. The thus obtained precipitate was washed with 80% aqueous ethanol solution, ethanol and diethyl ether, twice for each, consecutively. The precipitate was dried under reduced pressure to give the titled compound (101.7 mg). The degree of substitution of mefenamic acid was 17.5% when measured by an absorptiometric method. The thus obtained substance was dissolved in PBS to a concentration of 1.0% by weight to prepare a solution. The solution was a colorless and transparent liquid, and the result of its filter pass through test was "A".

Example 18

Synthesis of Aminopropanol-diclofenac Hydrochloride

1) Synthesis of Boc-aminopropanol-diclofenac

In 1 ml of dichloromethane, 135.8 mg (0.775 mmol) of Boc-aminopropanol was dissolved, 4 ml dichloromethane solution of 229.6 mg (0.775 mmol) of diclofenac (manufactured by Wako Pure Chemical Industries), 1 ml dichloromethane solution of 18.9 mg (0.155 mmol) DMAP and 0.5 ml of DMF were added thereto in this order, and 2 ml dichloromethane solution of 191.4 mg (0.998 mmol) of WSCI.HCl was added thereto under ice-cooling, followed by stirring for 7 hours while gradually returning to room temperature. The reaction solution was again ice-cooled, and, as an additional operation, 1 ml dichloromethane solution of 91.9 mg (0.310 mmol) of diclofenac, 7.5 mg (0.061 mmol) of DMAP and 1 ml dichloromethane solution of 70.9 mg (0.370 mmol) of WSCI.HCl were added thereto in this order, followed by stirring while gradually returning to room temperature. This additional operation was carried out 5 times. Ethyl acetate was added thereto, followed by separation by washing twice with 5% aqueous citric acid solution, twice with 5% aqueous sodium hydrogen carbonate solution and with saturated brine consecutively. After dehydration with sodium sulfate, ethyl acetate was evaporated under reduced pressure. The resulting residue was purified by silica gel column chromatography to give 280.2 mg (80%) of the titled compound. The structure was identified by $^1$H-NMR.

$^1$H-NMR (500 MHz, CDCl$_3$) δ (ppm)=1.44 (9H, s, Boc), 1.85 (2H, quant, —NHCH$_2$CH$_2$CH$_2$O—), 3.16 (2H, q, —NH CH$_2$CH$_2$CH$_2$O—), 3.82 (2H, s, Ph-CH$_2$—CO), 4.22 (2H, t, —NHCH$_2$CH$_2$CH$_2$O—), 4.68 (1H, s, NH), 6.54-7.35 (8H, m, Aromatic H, NH)

2) Synthesis of Aminopropanol-diclofenac Hydrochloride

In 2 ml of dichloromethane, 1019 mg of the Boc-aminopropanol-diclofenac obtained above was dissolved, and 8 ml of 4 M hydrochloric acid/ethyl acetate was added thereto under ice-cooling, followed by stirring for 3 hours. After 150 ml of diethyl ether was added thereto for precipitation, the precipitate was dried under reduced pressure. The titled compound was obtained at a yield of 791 mg (90%). The structure was identified by $^1$H-NMR.

$^1$H-NMR (500 MHz, CDCl$_3$) δ (ppm)=2.13 (2H, quant, —NHCH$_2$CH$_2$CH$_2$O—), 3.08 (2H, t, —NH CH$_2$CH$_2$CH$_2$O—), 3.84 (2H, s, Ph-CH$_2$—CO), 4.25 (2H, t, —NHCH$_2$CH$_2$CH$_2$O—), 6.52-7.33 (8H, m, Aromatic H, NH)

Example 19

Synthesis of Aminopropanol-diclofenac-Introduced Sodium Hyaluronate

In 56.3 ml water/56.3 ml dioxane, 500 mg (1.25 mmol/disaccharide unit) of hyaluronic acid having a weight average molecular weight of 800,000 was dissolved, and then HOSu (1 mmol)/0.5 ml water, WSCI.HCl (0.5 mmol)/0.5 ml water and 0.5 mmol/(water:dioxane=1:1, 5 ml) of the aminopropanol-diclofenac hydrochloride obtained above in Example 18 were added thereto in this order, followed by stirring overnight. To the reaction solution, 7.5 ml of 5% aqueous sodium hydrogen carbonate solution was added, followed by stirring for 3 hours and 40 minutes. After neutralizing the reaction solution by adding 215 μl of 50% acetic acid, 2.5 g of sodium chloride was added thereto, followed by stirring. The mixture was precipitated by adding 400 ml of ethanol, and the precipitate was washed twice with 85% aqueous ethanol solution, twice with ethanol and twice with diethyl ether and dried at room temperature overnight under reduced pressure to give 541 mg of a white solid. The degree of substitution of diclofenac was 18.2% when measured with a spectrophotometer.

Example 20

Synthesis of Aminopropanol-etodolac Hydrochloride

1) Synthesis of Boc-aminopropanol-etodolac

In 4 ml of dichloromethane, 178.8 mg (1.02 mmol) of Boc-aminopropanol, 293.8 mg (1.02 mmol) of etodolac (manufactured by Wako Pure Chemical Industries) and 23.8 mg (0.20 mmol) of DMAP were dissolved, and 2 ml dichloromethane solution of 233.8 mg (1.22 mmol) WSCI.HCl was added thereto under ice-cooling, followed by stirring overnight while gradually returning to room temperature. Further under ice-cooling, 2 ml dichloromethane solution of 68.8 mg (0.36 mmol) WSCI.HCl was added thereto, followed by stirring for 80 minutes while gradually returning to room temperature. Ethyl acetate was added thereto, followed by separation by washing twice with 5% aqueous citric acid solution, twice with 5% aqueous sodium hydrogen carbonate solution and with saturated brine consecutively. After dehydration drying with sodium sulfate, ethyl acetate was evaporated under reduced pressure. The thus obtained residue was purified by silica gel column chromatography to give 436.3 mg (96%) of the titled compound. The structure was identified by $^1$H-NMR.

$^1$H-NMR (500 MHz, CDCl$_3$) δ (ppm)=0.83 (3H, t, —CH$_2$CH$_3$), 1.37 (3H, t, —CH$_2$CH$_3$), 1.43 (9H, s, Boc), 1.79 (2H, quant, —NHCH$_2$CH$_2$CH$_2$O—), 3.14 (2H, q, —NHCH$_2$CH$_2$CH$_2$O—), 4.10-4.22 (2H, m, —NHCH$_2$CH$_2$CH$_2$O—), 4.63 (1H, s, NH), 7.00-7.37 (3H, m, Aromatic H), 8.97 (1H, s, NH)

2) Synthesis of Aminopropanol-etodolac Hydrochloride

In 1 ml of dichloromethane, 421.5 mg (0.948 mmol) of the Boc-aminopropanol-etodolac obtained above was dissolved, and 3 ml of 4 M hydrochloric acid/ethyl acetate was added thereto under ice-cooling, followed by stirring for 3 hours. Diethyl ether and hexane were added thereto for precipitation, and the precipitate was dried under reduced pressure. The precipitate was purified by silica gel column chromatography to give 197.6 mg (55%) of the titled compound. The structure was identified by $^1$H-NMR.

$^1$H-NMR (500 MHz, CDCl$_3$) δ (ppm)=0.81 (3H, t, —CH$_2$CH$_3$), 1.35 (3H, t, —CH$_2$CH$_3$), 1.92-2.17 (4H, m, —CH$_2$CH$_3$, —NHCH$_2$CH$_2$CH$_2$O—), 4.12 (1H, quant, —NHCH$_2$CH$_2$CH$_2$O—), 4.20 (1H, quant, —NHCH$_2$CH$_2$CH$_2$O—), 6.99-7.35 (3H, m, Aromatic H), 8.99 (1H, s, NH)

Example 21

Synthesis of Aminopropanol-etodolac-Introduced Sodium Hyaluronate

In 12.8 ml water/12.8 ml dioxane, 114 mg (0.285 mmol/disaccharide unit) of hyaluronic acid having a weight average molecular weight of 800,000 was dissolved, and then 0.228 mmol HOSu/0.1 ml water, 0.114 mmol WSCI.HCl/0.1 ml water and 0.114 mmol/(2 ml water:dioxane=1:1) of the aminopropanol-etodolac hydrochloride obtained in Example 20 were added thereto in this order, followed by stirring overnight. To the reaction solution, 1.71 ml of 5% aqueous sodium hydrogen carbonate solution was added, followed by stirring for 4.5 hours. After neutralizing the reaction solution by adding 49 μl of 50% acetic acid, 456 mg of sodium chloride was added thereto, followed by stirring. The mixture was precipitated by adding 110 ml of ethanol, and the precipitate was washed twice with 80% ethanol, twice with ethanol and twice with diethyl ether and dried at room temperature overnight under reduced pressure to give 111 mg of a white solid. The degree of substitution of etodolac was 14.4% by HPLC analysis.

Example 22

Synthesis of Aminopropanol-actarit Hydrochloride

1) Synthesis of Boc-aminopropanol-actarit

In 2 ml of dichloromethane, 123.1 mg (0.703 mmol) of the Boc-aminopropanol obtained in Reference Example 1 was dissolved, and then a DMF solution (1 ml) of 136.0 mg (0.704 mmol) of actarit was added thereto, and 17.1 mg (0.140 mmol) of DMAP and 175.4 mg (0.915 mmol) of WSCI.HCl were added thereto in this order under ice-cooling, followed by stirring overnight while gradually returning to room temperature. Ethyl acetate was added thereto, followed by separation by washing with 5% aqueous citric acid solution, 5% aqueous sodium hydrogen carbonate solution and saturated brine consecutively. After dehydration drying with sodium sulfate, ethyl acetate was evaporated under reduced pressure. The precipitate was purified by silica gel column chromatography to give 203.1 mg (83%) of the titled compound. The structure was identified by $^1$H-NMR.

$^1$H-NMR (500 MHz, CDCl$_3$) δ (ppm)=1.44 (9H, s, Boc), 1.80 (2H, quant, —NHCH$_2$CH$_2$CH$_2$O—), 2.18 (3H, s, NAc), 3.14 (2H, q, —NHCH$_2$CH$_2$CH$_2$O—), 3.59 (2H, s, Ph-CH$_2$—CO), 4.15 (2H, t, —NHCH$_2$CH$_2$CH$_2$O—), 4.66 (1H, s, NH), 7.13 (1H, s, NH), 7.23 (2H, d, Aromatic H), 7.46 (2H, d, Aromatic H)

In this connection, actarit was prepared by the following synthesis method.

p-Aminophenylacetic acid (1.02 mmol) (manufactured by Wako Pure Chemical Industries) was dissolved in dichloromethane-methanol-water (1:3:1, 50 ml), and acetic anhydride (2.12 mmol) was added thereto under ice-cooling, followed by stirring overnight while gradually returning to room temperature. The solvent was evaporated under reduced pressure to give the titled compound (196.4 mg, yield 99%). The structure was identified by $^1$H-NMR.

$^1$H-NMR (500 MHz, CD$_3$OD) d (ppm)=2.11 (3H, s, Ac), 3.55 (2H, s, Ph-CH$_2$—), 7.21-7.49 (4H, m, Aromatic H)

2) Synthesis of Aminopropanol-actarit Hydrochloride

In 2 ml of dichloromethane, 201.3 mg (0.574 mmol) of the Boc-aminopropanol-actarit obtained above was dissolved, and 3 ml of 4 M hydrochloric acid/ethyl acetate was added thereto under ice-cooling, followed by stirring for 3 hours. Diethyl ether was added thereto for precipitation, and the precipitate was washed twice with diethyl ether and then dried under reduced pressure to give 161.3 mg (98%) of the titled compound. The structure was identified by $^1$H-NMR.

$^1$H-NMR (500 MHz, CD$_3$OD) δ (ppm)=1.94-1.99 (2H, m, —NHCH$_2$CH$_2$CH$_2$O—), 2.11 (3H, s, NAc), 2.94 (2H, t, —NHCH$_2$CH$_2$CH$_2$O—), 3.63 (2H, s, Ph-CH$_2$—CO), 4.19 (2H, t, —NHCH$_2$CH$_2$CH$_2$O—), 7.22-7.51 (4H, m, Aromatic H)

Example 23

Synthesis of Aminopropanol-actarit-Introduced Sodium Hyaluronate

In 11.25 mL water/11.25 mL dioxane, 100 mg (0.25 mmol/disaccharide unit) of hyaluronic acid having a weight average molecular weight of 800,000 was dissolved, and then HOSu (0.2 mmol)/0.11 mL water, WSCI.HCl (0.1 mmol)/0.1 mL water and the aminopropanol-actarit hydrochloride obtained in Example 22 (0.1 mmol)/(water:dioxane=1:1, 2 mL) were added thereto in this order, followed by stirring overnight. To the reaction solution, 1.5 ml of 5% aqueous sodium hydrogen carbonate solution was added, followed by stirring for 3 hours. After neutralizing the reaction solution by adding 43 μl of 50% aqueous acetic acid solution, 400 mg of sodium chloride was added thereto, followed by stirring. The mixture was precipitated by adding 100 ml of ethanol, and the precipitate was washed twice with 80% ethanol, twice with ethanol and with diethyl ether and dried at room temperature overnight under reduced pressure to give 97 mg of a white solid. The degree of substitution of actarit was 13.2% by HPLC analysis.

Example 24

Synthesis of Aminopropanol-ketoprofen-Introduced Sodium Hyaluronate

In 23 ml water/23 ml dioxane, 200 mg (0.5 mmol/disaccharide unit) of hyaluronic acid having a weight average molecular weight of 900,000 was dissolved, and 0.3 mmol/2 ml aqueous solution of HOSu, 0.15 mmol/2 ml aqueous solution of WSCI.HCl and 1.5 mmol/2 ml aqueous solution of the aminopropanol-ketoprofen hydrochloride obtained in Example 1 were added thereto in this order, followed by stirring overnight. After 11.5 ml of the reaction solution was collected, 100 mg of sodium chloride was added thereto, followed by stirring. The mixture was precipitated by adding 50 ml of ethanol, and the precipitate was washed twice with 80% ethanol, twice with ethanol and twice with diethyl ether and dried at room temperature overnight under reduced pressure to give 35 mg of a white powder. The degree of substitution of ketoprofen was 7.2% by HPLC analysis.

The thus obtained substance was dissolved in PBS to a concentration of 1.0% by weight to prepare a solution. The solution was a colorless and transparent liquid, and the result of its filter pass through test was "C".

Reference Example 2

Synthesis of Boc-serinol

Serinol (10.1 mmol) (manufactured by Aldrich Chem. Co.) was dissolved in water-dioxane (1:1, 20 ml), and then a dioxane solution (15 ml) of $Boc_2O$ (10.8 mmol) was added thereto under ice-cooling, followed by stirring overnight while returning to room temperature. The solvent was evaporated under reduced pressure. The residue was washed with hexane and then dried under reduced pressure to give the titled compound (1847 mg, yield 95%). The structure was identified by $^1$H-NMR.

$^1$H-NMR (500 MHz, $CD_3OD$) δ (ppm)=1.44 (9H, s, Boc), 3.57-3.58 (5H, m, Serinol)

Example 25

Synthesis of Serinol-ketoprofen Hydrochloride

1) Synthesis of Boc-serinol-ketoprofen

Ketoprofen (1.11 mmol) (manufactured by Tokyo Kasei Kogyo) was dissolved in dichloromethane (3 ml), and triethylamine (1.11 mmol) and dichloromethane solution (2 ml) of dimethylphosphinothioyl chloride (Mpt-Cl) (1.11 mmol) were added thereto in this order, followed by stirring for 25 minutes. Triethylamine (0.36 mmol) was further added thereto, followed by stirring for 20 minutes. The reaction solution was ice-cooled, and triethylamine (1.11 mmol), DMAP (0.19 mmol) and the Boc-serinol obtained in Reference Example 2 (0.50 mmol) were added thereto in this order, followed by stirring overnight by returning to room temperature. The reaction solution was again ice-cooled, and 25% aqueous ammonia (2 ml) and dioxane (10 ml) were added thereto in this order, followed by stirring for 20 minutes. The reaction solution was concentrated to 5 ml, and ethyl acetate was added thereto. Separation by washing with water, 5% aqueous citric acid solution, 5% aqueous sodium hydrogen carbonate solution and saturated brine consecutively was carried out, and after dehydration drying with sodium sulfate the solvent was evaporated under reduced pressure. The precipitate was purified by silica gel column chromatography (hexane:ethyl acetate=2:1, 0.5% triethylamine) to give the titled compound (287.3 mg, yield 87%). The structure was identified by $^1$H-NMR ($CDCl_3$).

$^1$H-NMR (500 MHz, $CDCl_3$) δ (ppm)=1.38-1.40 (9H, m, Boc), 1.51-1.53 (6H, m, —OCOCH($CH_3$)—), 3.76-3.81 (2H, m, —OCO$CH$($CH_3$)—), 3.96-4.11 (4H, m, —$CH_2$CH(NHBoc)$CH_2$—), 4.61 (1H, btd, —$CH_2$$CH$(NHBoc)$CH_2$—), 7.40-7.80 (18H, m, Aromatic)

2) Synthesis of Serinol-ketoprofen Hydrochloride

Boc-serinol-ketoprofen (0.428 mmol) was dissolved in dichloromethane (1 ml), and 4 N hydrochloric acid/ethyl acetate (4 ml) was added thereto under ice-cooling, followed by stirring for 2 hours while gradually returning to room temperature. After confirming disappearance of Boc-serinol-ketoprofen by TLC, diethyl ether and hexane were added thereto, and the resulting precipitate was centrifuged. The thus obtained precipitate was dried under reduced pressure to give the titled compound (243.6 mg, qu.). The structure was identified by $^1$H-NMR ($CDCl_3$).

$^1$H-NMR (500 MHz, $CDCl_3$) δ (ppm)=1.49 (6H, t, —OCOCH($CH_3$)—), 3.79 (1H, m, —$CH_2$$CH$(NHBoc)$CH_2$—), 4.00-4.53 (6H, m, Serinol, Ketoprofen), 7.31-7.80 (18H, m, Aromatic)

Example 26

Synthesis of Serinol-ketoprofen-Introduced Hyaluronic Acid

In water-dioxane (1:1, 22.5 ml), 0.25 mmol/disaccharide unit of hyaluronic acid (100 mg) having a weight average molecular weight of 900,000 was dissolved, and 2 mol/L HOSu (0.1 ml), 1 mol/L WSCI.HCl (0.1 ml) and a dioxane solution (2 ml) of the serinol-ketoprofen hydrochloride obtained in Example 25 (0.10 mmol) were added thereto, followed by stirring overnight. To the reaction solution, 5% aqueous sodium hydrogen carbonate solution (1.5 ml) was added, followed by stirring for 4 hours. The mixture was neutralized by adding 50% aqueous acetic acid solution (43 μl), and sodium chloride (0.4 g) was added thereto, followed by stirring. Ethanol (100 ml) was added thereto, followed by stirring, and the thus formed precipitate was centrifuged. The thus obtained precipitate was washed with 80% aqueous ethanol solution, ethanol and diethyl ether consecutively, twice for each. The precipitate was dried under reduced pressure to give the titled compound (92.3 mg). The degree of substitution of ketoprofen was 11.2% by HPLC analysis. The thus obtained substance was dissolved in PBS to a concentration of 1.0% by weight to prepare a solution. The solution was a colorless and transparent liquid, and the result of its filter pass through test was "A".

Example 27

Synthesis of 2-amino-1,5-pentanediol-ketoprofen Hydrochloride

1) Synthesis of Boc-amino-1,5-pentanediol-ketoprofen

Boc-amino-1,5-pentanediol (Boc-NHCH($CH_2OH$)$CH_2CH_2CH_2OH$, manufactured by Aldrich Chem. Co.) (1.98 mmol) was dissolved in dichloromethane (2 ml), and a dichloromethane solution (4 ml) of ketoprofen (3.96 mmol) (manufactured by Tokyo Kasei Kogyo) and a dichloromethane solution (1 ml) of DMAP (0.791 mmol) were added thereto in this order, followed by stirring. The reaction solution was ice-cooled, and a dichloromethane solution (5 ml) of WSCI.HCl (4.93 mmol) was added thereto, followed by stirring overnight while gradually returning to room temperature. The reaction solution was diluted with ethyl acetate, washed with 5% aqueous citric acid solution, 5% aqueous sodium hydrogen carbonate solution and saturated brine consecutively, followed by dehydration drying with sodium sulfate, and then the solvent was evaporated under reduced pressure. The thus obtained residue was purified by silica gel column chromatography (hexane:ethyl acetate=5:2, 0.5% triethylamine) to give the titled compound (1.361 g, yield 99%). The structure was identified by $^1$H-NMR (CDCl$_3$).

$^1$H-NMR (500 MHz, CDCl$_3$) δ (ppm)=1.39-1.40 (9H, m, Boc), 1.51-1.55 (6H, m, —OCOCH(C$\underline{H_3}$)—), 3.75-4.55 (8H, m, Ketoprofen, 2-amino-1,5-pentanediol), 7.40-7.80 (18H, m, Aromatic)

2) Synthesis of 2-amino-1,5-pentanediol-ketoprofen Hydrochloride

The Boc-amino-1,5-pentanediol-ketoprofen (1.95 mmol) obtained above was dissolved in dichloromethane (1 ml), and 4 N hydrochloric acid/ethyl acetate (4 ml) was added thereto under ice-cooling, followed by stirring for 3 hours while gradually returning to room temperature. Hexane was added to the reaction solution, and the thus formed white precipitate was centrifuged. The thus obtained precipitate was dried under reduced pressure to give the titled compound (1.20 g, yield 98%). The structure was identified by $^1$H-NMR (CDCl$_3$).

$^1$H-NMR (500 MHz, CDCl$_3$) δ (ppm)=1.50 (3H, d, —OCOCH(C$\underline{H_3}$)—), 1.51 (3H, d, —OCOCH(C$\underline{H_3}$)—), 3.47 (1H, bd, 2-amino-1,5-pentanediol), 3.44-4.48 (6H, m, Ketoprofen, 2-amino-1,5-pentanediol), 7.33-7.84 (18H, m, Aromatic)

Example 28

Synthesis of 2-amino-1,5-pentanediol-ketoprofen-Introduced Hyaluronic Acid

In water-dioxane (1:1, 30.8 ml), 0.34 mmol/disaccharide unit of hyaluronic acid (137 mg) having a weight average molecular weight of 900,000 was dissolved, and 2 mol/L HOSu (0.137 ml), 1 mol/L WSCI.HCl (0.137 ml) and a water-dioxane (1:1) solution (4 ml) of the 2-amino-1,5-pentanediol-ketoprofen hydrochloride (0.137 mmol) obtained in Example 27 were added thereto in this order, followed by stirring overnight. To the reaction solution, 5% aqueous sodium hydrogen carbonate solution (2.1 ml) was added, followed by stirring for 5 hours. After carrying out neutralization by adding 50% aqueous acetic acid solution (59 µl), sodium chloride (0.548 g) was added thereto, followed by stirring. Ethanol (140 ml) was added thereto, followed by stirring, and the thus formed precipitate was centrifuged.

The thus obtained precipitate was washed with 80% aqueous ethanol solution, ethanol and diethyl ether. The precipitate was dried under reduced pressure to give the titled compound (135.1 mg). The degree of substitution of ketoprofen was 18.5% by HPLC analysis. The thus obtained substance was dissolved in PBS to a concentration of 1.0% by weight to prepare a solution. The solution was a colorless and transparent liquid, and the result of its filter pass through test was "A".

Example 29

Synthesis of 3-amino-1,2-propanediol-ketoprofen hydrochloride

1) Synthesis of Boc-amino-1,2-propanediol-ketoprofen

Boc-amino-1,2-propanediol (Boc-NHCH$_2$CH(OH)CH$_2$OH, manufactured by Aldrich Chem. Co.) (2.05 mmol) was dissolved in dichloromethane (2 ml), and a dichloromethane solution (4 ml) of ketoprofen (4.11 mmol) (manufactured by Tokyo Kasei Kogyo) and a dichloromethane solution (1 ml) of DMAP (0.803 mmol) were added thereto in this order, followed by stirring. The reaction solution was ice-cooled, and a dichloromethane solution (5 ml) of WSCI.HCl (4.94 mmol) was added thereto, followed by stirring overnight while gradually returning to room temperature. The reaction solution was ice-cooled, and a dichloromethane solution (1 ml) of WSCI.HCl (1.24 mmol) was added thereto, followed by stirring at room temperature for 1 hour and then at 35° C. for 2 hours. Ethyl acetate was added thereto, followed by washing with 5% aqueous citric acid solution, 5% aqueous sodium hydrogen carbonate solution and saturated brine consecutively. Dehydration drying with sodium sulfate was carried out, and then the solvent was evaporated under reduced pressure. The thus obtained residue was purified by silica gel column chromatography (hexane:ethyl acetate=2:1, 0.5% triethylamine) to give the titled compound (1.175 g, yield 87%). The structure was identified by $^1$H-NMR (CDCl$_3$).

$^1$H-NMR (500 MHz, CDCl$_3$) δ (ppm)=1.36-1.40 (9H, m, Boc), 1.42-1.53 (6H, m, —OCOCH(C$\underline{H_2}$)—), 3.10-3.30 (2H, m, BocNHC$\underline{H_2}$—), 3.65-3.82 (2H, m, —OCOC$\underline{H}$(CH$_3$)—), 3.99-4.36 ($\overline{2H}$,m, BocNHCH$_2$(CHO—) C$\underline{H_2}$O—), 4.49-4.76 (1H, m, BocN$\underline{H}$—), 5.04-5.09 (1$\overline{H}$, m, BocNHCH$_2$ (C$\underline{H}$O—)CH$_2$O—), 7.38-7.80 (18H, m, Aromatic)

2) Synthesis of 3-amino-1,2-propanediol-ketoprofen Hydrochloride

The Boc-amino-1,2-propanediol-ketoprofen (1.76 mmol) obtained above was dissolved in dichloromethane (1 ml), and under ice-cooling, 4 N hydrochloric acid/ethyl acetate (4 ml) was added thereto, followed by stirring for 3 hours. Hexane was added to the reaction solution, and the thus formed white precipitate was dried under reduced pressure to give the titled compound (1.029 g, yield 97%). The structure was identified by $^1$H-NMR (CDCl$_3$).

$^1$H-NMR (500 MHz, CDCl$_3$) δ (ppm)=1.33-1.49 (6H, m, —OCOCH(C$\underline{H_3}$)—), 3.02-3.20 (m, 2H, H$_2$N CH$_2$(CHO—)CH$_2$O—), 3.56-3.82 (1H, m, —OCO C$\underline{H}$(CH$_3$)—), 3.90-4.15 (2H, m, H$_2$NCH$_2$(CHO—) CH$_2$O—, —OCOC$\underline{H}$(CH$_3$)—), 4.18-4.50 (1H, m, H$_2$NCH$_2$C$\overline{H}$(O—) CH$_2$O—), 5.35-5.37 (1H, m, H$_2$NCH$_2$—C$\underline{H}$(O—)CH$_2$O—), 7.30-7.80 (18H, m, Aromatic)

Example 30

Synthesis of 3-amino-1,2-propanediol-ketoprofen-introduced Hyaluronic Acid

In water-dioxane (1:1, 45 ml), hyaluronic acid (200 mg) 0.5 mmol/disaccharide unit having a weight average molecular weight of 900,000 was dissolved, and 2 mol/L HOSu (0.25 ml), 1 mol/L WSCI (0.25 ml) and a water-dioxane (1:1) solution (4 ml) of the 3-amino-1,2-propanediol-ketoprofen hydrochloride (0.20 mmol) obtained in Example 29 were added thereto in this order, followed by stirring overnight. To the reaction solution, 5% aqueous sodium hydrogen carbonate solution (3 ml) was added, followed by stirring for 4 hours. The mixture was neutralized by adding 50% aqueous acetic acid solution (86 µl), and sodium chloride (0.8 g) was added thereto, followed by stirring. Ethanol (200 ml) was added thereto, followed by stirring, and the thus formed precipitate was centrifuged. The thus obtained precipitate was washed with 80% aqueous ethanol solution, ethanol and diethyl ether. The precipitate was dried under reduced pressure to give the titled compound (217.4 mg). The degree of substitution of ketoprofen was 40.3% by HPLC analysis. The thus obtained substance was dissolved in PBS to a concentration of 1.0% by weight to prepare a solution. The solution was a colorless and transparent liquid, and the result of its filter pass through test was "A".

Reference Example 3

Synthesis of Boc-tris(hydroxymethyl)aminomethane

Tris(hydroxymethyl)aminomethane (10.1 mmol) was dissolved in water-dioxane (1:2, 30 ml), and water-dioxane solution (1:9, 10 ml) of $Boc_2O$ (10.8 mmol) was added thereto, followed by stirring at room temperature for 45 minutes and then at 40° C. for 70 minutes. A dioxane solution (3 ml) of $Boc_2O$ (5.41 mmol) was added thereto, followed by stirring overnight while gradually returning to room temperature. The solvent was evaporated under reduced pressure. The precipitate was washed with hexane and then dried under reduced pressure to give the titled compound (2.21 g, yield 99%). The structure was identified by $^1$H-NMR.

$^1$H-NMR (500 MHz, $CD_3OD$) d (ppm)=1.44 (9H, s, Boc), 3.68 (6H, s, —C($\underline{CH_2}OH)_3$)

Example 31

Synthesis of Tris(hydroxymethyl)aminomethane-ketoprofen Hydrochloride

1) Synthesis of Boc-tris(hydroxymethyl)aminomethane-ketoprofen

In 3 ml of dichloromethane, 419 mg (1.65 mmol) of ketoprofen (manufactured by Tokyo Kasei Kogyo) was dissolved, and 230 µl (1.65 mmol) of triethylamine and Mpt-Cl 213 mg (1.65 mmol)/2 ml dichloromethane were added thereto in this order under ice-cooling, followed by stirring for 10 minutes. Next, 230 µl (1.65 mmol) of triethylamine, 33 mg (0.27 mmol) of DMAP and 110 mg (0.5 mmol) of the Boc-tris (hydroxymethyl)aminomethane (Boc-NHC($CH_2OH)_3$) obtained in Reference Example 3 were added thereto in this order, followed by stirring overnight after returning to room temperature. After adding 2 ml of aqueous ammonia, dioxane was added thereto until dichloromethane and aqueous ammonia became uniform, and the mixture was stirred for 40 minutes. Dichloromethane was evaporated under reduced pressure, and ethyl acetate was added to the residue, followed by separation by washing twice with 5% citric acid, with water, twice with 5% sodium hydrogen carbonate, with water and with saturated brine consecutively. After dehydration drying with sodium sulfate, ethyl acetate was evaporated under reduced pressure and the residue was purified by silica gel column chromatography (dichloromethane:methanol=100:1→175:1). The titled compound was quantitatively obtained at a yield of 467 mg. The structure was identified by $^1$H-NMR ($CDCl_3$) to confirm that 3 molecules of ketoprofen were introduced into 1 molecule of Boc-tris(hydroxymethyl) amino methane.

$^1$H-NMR (500 MHz, $CDCl_3$) δ (ppm)=1.29 (9H, s, Boc), 1.44-1.54 (3H×3, m, —OCOCH($\underline{CH_3}$)—), 3.76 (1H×3, q, —OCO$\underline{CH}(CH_3)$—), 4.04-4.27 (6H, m, —NHC($\underline{CH_2}$O—KP)$_3$), 4.81 (1H, br, —$\underline{NH}$—), 7.37-7.85 (9H×3, m, Aromatic H)

2) Synthesis of Tris(hydroxymethyl)aminomethane-ketoprofen Hydrochloride

In 1 ml of dichloromethane, 453 mg (0.49 mmol) of the Boc-tris(hydroxymethyl)aminomethane-ketoprofen obtained above was dissolved, and under ice-cooling, 3 ml of 4 M hydrochloric acid/ethyl acetate was added thereto, followed by stirring for 30 minutes under ice-cooling and then at room temperature for 1 hour and 30 minutes. After confirming disappearance of Boc-tris(hydroxymethyl)aminomethane-ketoprofen by TLC, diethyl ether and hexane were added thereto for decantation. Thereafter, the precipitate was dried under reduced pressure to give the titled compound with the yield of 411 mg (97%). The structure was identified by $^1$H-NMR ($CDCl_3$).

$^1$H-NMR (500 MHz, $CDCl_3$) δ (ppm)=1.39-1.50 (3H×3, m, —OCOCH($\underline{CH_3}$)—), 3.96 (1H×3, q, —OCO$\underline{CH}(CH_3)$—), 4.09-4.46 (6H, m, —NHC($\underline{CH_2}$O—KP)$_3$), 7.25-7.80 (9H×3, m, Aromatic H), 9.31 (br, $\underline{H_3N^+CH_2}$—)

Example 32

Synthesis of glycine-tris(hydroxymethyl)aminomethane-ketoprofen Hydrochloride

1) Synthesis of Boc-glycine-tris(hydroxymethyl)aminomethane-ketoprofen

In 1 ml of chloroform, 133 mg (0.76 mmol) of Boc-glycine was dissolved, and 106 µl (0.76 mmol) of triethylamine and Mpt-Cl 98 mg (0.76 mmol)/1 ml chloroform were added thereto under ice-cooling, followed by stirring for 10 minutes. Thereafter, 433 mg (0.5 mmol) of the tris(hydroxymethyl) aminomethane-ketoprofen hydrochloride obtained in Example 31/70 µl (0.5 mmol) of triethylamine/2 ml of chloroform, and 106 µl (0.76 mmol) of triethylamine were gradually added thereto by dividing into 4 portions. After stirring at room temperature for 1 hour, 106 µl (0.76 mmol) of triethylamine was further added thereto under ice-cooling, and a mixed acid anhydride of Boc-glycine activated by dissolving 131 mg (0.75 mmol) of Boc-glycine in 1 ml chloroform and by adding, under ice-cooling, 105 µl (0.75 mmol) of triethylamine and 95 mg (0.75 mmol) Mpt-Cl/1 ml chloroform was added thereto, and the mixture was stirred at room temperature overnight. Ethyl acetate was added thereto, followed by separation by washing twice with 5% citric acid, water, twice with 5% sodium hydrogen carbonate, water and saturated brine consecutively. After dehydration drying with sodium sulfate, ethyl acetate was evaporated under reduced pressure and the residue was purified by silica gel column chromatography (hexane:ethyl acetate=3:2) to give 411 mg of the titled compound (yield 55%). The structure was identified by $^1$H-NMR ($CDCl_3$).

$^1$H-NMR (500 MHz, $CDCl_3$) δ (ppm)=1.43 (9H, s, Boc), 1.45-1.52 (3H×3, m, —OCOCH($\underline{CH_3}$)—), 3.56 (2H, br, —NHCH$_2$CO—), 3.76 (1H×3, q, —OCOCH(CH$_3$)—), 3.98-4.28 (6H, m, —NHC(CH$_2$O—KP)$_3$), 5.51 (1H, br, —NHCH$_2$CO—), 6.63 (1H, br, —NHC(CH$_2$O—KP)$_3$), 7.34-7.83 (9H×3, m, Aromatic H)

2) Synthesis of Glycine-tris(hydroxymethyl)aminomethane-ketoprofen Hydrochloride To 361 mg (0.37 mmol) of the Boc-glycine-tris(hydroxymethyl)aminomethane-ketoprofen obtained above, 2 ml of 4 M hydrochloric acid/ethyl acetate was added under ice-cooling and stirred at room temperature for 2 hours. After confirming disappearance of Boc-glycine-tris(hydroxymethyl)aminomethane-ketoprofen by TLC, diethyl ether and hexane were added thereto for decantation. Thereafter, the precipitate was dried under reduced pressure to give the titled compound quantitatively with the yield of 336 mg. The structure was identified by $^1$H-NMR (CDCl$_3$).

$^1$H-NMR (500 MHz, CDCl$_3$) δ (ppm)=1.40 (3H×3, m, —OCOCH(CH$_3$)—), 3.68-4.24 (11H, m, 2H; —NHCH$_2$CO—, 1H×3; —OCOCH(CH$_3$)—, 6H; —NHC(CH$_2$O—KP)$_3$), 7.27-7.82 (9H×3, m, Aromatic H), 8.31 (br, H$_3$N$^+$CH$_2$—)

Example 33

Synthesis of Glycine-tris(hydroxymethyl)aminomethane-ketoprofen-Introduced Hyaluronic Acid In 11.5 ml water/11.5 ml dioxane, 100 mg (0.25 mmol/disaccharide unit) of hyaluronic acid having a weight average molecular weight of 900,000 was dissolved, and 2 mol/l HOSu/0.1 ml water, 1 mol/l WSCI.HCl/0.1 ml water and 93 mg (0.1 mmol)/3 ml dioxane of the glycine-tris(hydroxymethyl)aminomethane-ketoprofen hydrochloride obtained in Example 32 were added thereto in this order, followed by stirring overnight. To the reaction solution, 5% aqueous sodium hydrogen carbonate solution was added, followed by stirring for 4 hours and 45 minutes. After neutralization of the reaction solution by adding 43μl of 50% acetic acid, 400 mg of sodium chloride was added thereto, followed by stirring. The mixture was precipitated by adding 100 ml of ethanol, and the precipitate was washed twice with 80% ethanol, twice with ethanol and with diethyl ether and dried at room temperature overnight under reduced pressure to give 95 mg of white solid. The degree of substitution of ketoprofen was 39% by HPLC analysis. The thus obtained substance was dissolved in PBS to a concentration of 1.0% by weight to prepare a solution. The solution was a colorless and transparent liquid, and the result of its filter pass through test was "A".

Reference Example 4

Synthesis of Boc-aminopropyl Bromide

In 20 ml of dichloromethane, 1.222 g (5.58 mmol) of 3-bromopropylamine hydrobromide was dissolved, 0.778 ml (5.58 mmol) of triethylamine was added thereto under ice-cooling, and 50 ml dichloromethane solution of 1.214 g (5.56 mmol) of Boc$_2$O was further added dropwise thereto in 10 minutes, followed by stirring. After stirring at room temperature for 50 minutes, ethyl acetate was added thereto, followed by separation by washing with 5% aqueous citric acid solution, water and saturated brine consecutively. After dehydration with sodium sulfate, the solvent was evaporated under reduced pressure to give 1.304 of the titled compound (98%). The structure was identified by $^1$H-NMR.

$^1$H-NMR (500 MHz, CDCl$_3$) δ (ppm)=1.44 (9H, s, Boc), 2.05 (2H, quant, —NHCH$_2$CH$_2$CH$_2$Br), 3.28 (2H, q, —NHCH$_2$CH$_2$CH$_2$Br), 3.44 (2H, t, —NHCH$_2$CH$_2$CH$_2$Br), 4.64 (1H, s, NH)

Example 34

Synthesis of aminopropanol-diclofenac Hydrochloride (1) Boc-aminopropanol-diclofenac In 3 ml of DMF, 1.476 g (4.64 mmol) of diclofenac sodium was dissolved, and 7 ml DMF solution of 1.105 g (4.64 mmol) of the Boc-aminopropyl bromide obtained in Reference Example 6 was added dropwise thereto under ice-cooling, followed by stirring overnight at room temperature and then stirring at 60° C. for 10 hours. The mixture was stirred overnight at room temperature and then stirred at 60° C. for 9 hours and further stirred at room temperature for 3 days. Ethyl acetate was added thereto, followed by separation by washing twice with 5% aqueous sodium hydrogen carbonate solution, water and saturated brine consecutively. After dehydration with sodium sulfate, ethyl acetate was evaporated under reduced pressure. The thus obtained residue was purified by silica gel column chromatography (hexane:ethyl acetate=7:1, 0.5% triethylamine) to give 1.702 g (81%) of the titled compound.

(2) Aminopropanol-diclofenac Hydrochloride

In 2 ml of dichloromethane, 1019 mg (2.25 mmol) of the Boc-aminopropanol-diclofenac obtained above was dissolved, and 8 ml of 4 M hydrochloric acid/ethyl acetate was added thereto under ice-cooling, followed by stirring for 3 hours. 150 ml of diethyl ether was added thereto for precipitation, and the precipitate was dried under reduced pressure to give 791 mg (90%) of the titled compound. The structure was identified by $^1$H-NMR.

$^1$H-NMR (500 MHz, CDCl$_3$) δ (ppm)=2.13 (2H, quant, —NHCH$_2$CH$_2$CH$_2$O—), 3.08 (2H, t, —NHCH$_2$CH$_2$CH$_2$O—), 3.84 (2H, s, Ph-CH$_2$—CO), 4.25 (2H, t, —NHCH$_2$CH$_2$CH$_2$O—), 6.52-7.33 (8H, m, Aromatic H, NH)

Example 35

Synthesis of Aminopropanol-diclofenac-Introduced Sodium Hyaluronate (DS 4.3%)

In 57.5 mL water/57.5 mL dioxane, 500 mg (1.25 mmol/disaccharide unit) of hyaluronic acid having a weight average molecular weight of 800,000 was dissolved, and then 0.33 M HOSu/0.75 mL water, 0.16 M WSCI.HCl/0.75 mL water and 0.16 M the aminopropanol-diclofenac hydrochloride obtained above in Example 34/0.75 mL water were added thereto in this order, followed by stirring overnight. Next, 375 mg of sodium hydrogen carbonate/3 ml water was added to the reaction solution, followed by stirring for 4 hours. After neutralization of the reaction solution by adding 108 μl of acetic acid, 3.0 g of sodium chloride was added thereto, followed by stirring. The mixture was precipitated by adding 200 ml of ethanol, and the precipitate was washed twice with 80% ethanol, twice with ethanol and twice with diethyl ether and dried at room temperature overnight under reduced pressure to give 505 mg of a white solid. The degree of substitution of diclofenac was 4.3% when measured with a spectrophotometer.

Example 36

Synthesis of Aminopropanol-diclofenac-Introduced Sodium Hyaluronate (DS 9.7%)

In 57.5 ml water/57.5 ml dioxane, 500 mg (1.25 mmol/disaccharide unit) of hyaluronic acid having a weight average molecular weight of 800,000 was dissolved, and then 0.5 M HOSu/(water:dioxane=1:1) 1.0 ml, 0.25 M WSCI.HCl/(water:dioxane=1:1) 1.0 ml and the 0.25 M aminopropanol-diclofenac hydrochloride obtained above in Example 34/(water:dioxane=1:1) 1.0 ml were added thereto in this order, followed by stirring overnight. Next, 380 mg of sodium hydrogen carbonate/5 ml water was added to the reaction solution, followed by stirring for 4 hours. After neutralization of the reaction solution by adding 108 µl of acetic acid, 3.0 g of sodium chloride was added thereto, followed by stirring. The mixture was precipitated by adding 200 ml of ethanol, and the precipitate was washed three times with 80% ethanol, twice with ethanol and twice with diethyl ether and dried at room temperature overnight under reduced pressure to give 503 mg of a white solid. The degree of substitution of diclofenac was 9.7% when measured with a spectrophotometer.

Example 37

Synthesis of Aminopropanol-diclofenac-Introduced Sodium Hyaluronate (65 kDa) Sodium (DS 17.1%) Using Hyaluronic Acid Having an Average Molecular Weight of 65 kDa In 22.5 mL water/22.5 mL dioxane, 200.8 mg (0.50 mmol/disaccharide unit) of hyaluronic acid having an average molecular weight of 65 kDa was dissolved, and then 0.4 mL of 1 M HOSu, 0.4 mL of 0.5 M WSCI.HCl and 0.1 M/(water:dioxane=1:1) 2.0 mL of the aminopropanol-diclofenac hydrochloride obtained above in Example 34 were added thereto in this order, followed by stirring overnight. Next, 3 ml of 5% aqueous sodium hydrogen carbonate solution was added to the reaction solution, followed by stirring for 3 hours. After neutralization of the reaction solution by adding 86 µl of 50% acetic acid, 1.0 g of sodium chloride was added thereto, followed by stirring. The mixture was precipitated by adding 200 ml of ethanol, and the precipitate was washed twice with 85% ethanol, twice with ethanol and with diethyl ether and dried at room temperature overnight under reduced pressure to give 190.5 mg of a white solid. The degree of substitution of diclofenac was 17.1% when measured with a spectrophotometer.

Reference Example 5

Boc-aminoethyl Bromide

In 20 ml of dichloromethane, 2.155 g (10.5 mmol) of 3-bromoethylamine hydrobromide was dissolved, 1.463 ml (10.5 mmol) of triethylamine was added thereto under ice-cooling, and 5 ml dichloromethane solution of 2.299 g (10.5 mmol) $Boc_2O$ was further added thereto, followed by stirring. After stirring at room temperature for 90 minutes, ethyl acetate was added thereto, followed by separation by washing with 5% aqueous citric acid solution, water and saturated brine consecutively. After dehydration with sodium sulfate, the solvent was evaporated under reduced pressure to give 2.287 g of the titled compound (97%). The structure was identified by $^1$H-NMR.

$^1$H-NMR (500 MHz, $CDCl_3$) δ (ppm)=1.45 (9H, s, Boc), 3.45-3.55 (4H, m, —NH$\underline{CH_2CH_2}$Br), 4.93 (1H, s, NH)

Example 38

Synthesis of Aminoethanol-diclofenac hydrochloride (1) Boc-aminoethanol-diclofenac After ice-cooling 5 ml of DMF solution containing 2.287 g (10.2 mmol) of the Boc-aminoethyl bromide obtained in Reference Example 5, 6 ml of DMF solution containing 3.255 g (10.2 mmol) of diclofenac sodium was added thereto, followed by stirring at room temperature overnight. The mixture was stirred at 60° C. for 11 hours and then stirred at room temperature overnight. Ethyl acetate was added thereto, and separation by washing with 5% aqueous sodium hydrogen carbonate solution, water and saturated brine consecutively was carried. After dehydration with sodium sulfate, ethyl acetate was evaporated under reduced pressure. The resulting residue was purified by silica gel column chromatography (toluene:ethyl acetate=20:1, 0.5% triethylamine) to give 2.675 g (60%) of the titled compound. The structure was identified by $^1$H-NMR.

$^1$H-NMR (500 MHz, $CDCl_3$) δ (ppm)=1.42 (9H, s, Boc), 3.41 (2H, d, —NH$\underline{CH_2}$CH$_2$O—), 3.83 (2H, s, Ph-$\underline{CH_2}$—CO), 4.21 (2H, t, —NH$\overline{CH_2CH_2}$O—), 4.72 (1H, s, N$\overline{H}$), 6.54-7.47 (8H, m, Aromatic H, N$\overline{H}$)

(2) Aminoethanol-diclofenac Hydrochloride

In 5 ml of dichloromethane, 2.108 g (4.80 mmol) of the Boc-aminoethanol-diclofenac obtained above was dissolved, and 20 ml of 4 M hydrochloric acid/ethyl acetate was added thereto under ice-cooling, followed by stirring for 2.5 hours. Diethyl ether and hexane were added thereto for precipitation, and the precipitate was dried under reduced pressure to give 1.775 g (98%) of the titled compound. The structure was identified by $^1$H-NMR.

$^1$H-NMR (500 MHz, $CDCl_3$) δ (ppm)=3.18 (2H, t, $NH_2$ $\underline{CH_2}$CH$_2$O—), 3.94 (2H, s, Ph-$\underline{CH_2}$—CO), 4.37 (2H, t, NH$_2$CH$_2$$\underline{CH_2}$O—), 6.47-7.31 (8H, m, Aromatic H, NH)

Example 39

Synthesis of Aminoethanol-diclofenac-Introduced Sodium Hyaluronate (DS 14.7%)

In 57.5 mL water/57.5 mL dioxane, 500 mg (1.25 mmol/disaccharide unit) of hyaluronic acid having a weight average molecular weight of 800,000 was dissolved, and then 0.5 mL of 2 M HOSu, 0.5 mL of 1 M WSCI.HCl and 3 mL of a solution (water:dioxane=1:1) of 188.6 mg (0.5 mmol) of the aminoethanol-diclofenac hydrochloride obtained in Example 38 were added thereto in this order, followed by stirring overnight. Next, 7.5 ml of 5% aqueous sodium hydrogen carbonate solution was added thereto, followed by stirring for 4 hours. After neutralization of the reaction solution by adding 215 µl of 50% acetic acid, 2.5 g of sodium chloride was added thereto, followed by stirring. The mixture was precipitated by adding 500 ml of ethanol, and the precipitate was washed twice with 85% ethanol, twice with ethanol and twice with diethyl ether and dried at room temperature overnight under reduced pressure to give 473.7 mg of a white solid. The degree of substitution of diclofenac was 14.7% when measured with a spectrophotometer.

Example 40

Synthesis of Diaminopropane-diclofenac Hydrochloride (1) Boc-propylamide-diclofenac In 3 ml of dichloromethane, 338.4 mg (1.94 mmol) of tert-butyl N-(2-aminopropyl)carbamic acid (manufactured by Tokyo Kasei Kogyo) and 694.4 mg (2.34 mmol) of diclofenac were dissolved, and under ice-cooling, 59.0 mg (0.483 mmol) of DMAP and 505.3 mg (2.64 mmol) of WSCI·HCl were added thereto, followed by stirring for 70 minutes and then stirred at room temperature for 90 minutes. Ethyl acetate was added thereto, followed by separation by washing with 5% aqueous citric acid solution, 5% aqueous sodium hydrogen carbonate solution and saturated brine consecutively. After dehydration with sodium sulfate, ethyl acetate was evaporated under reduced pressure. The resulting residue was purified by silica gel column chromatography (hexane:ethyl acetate=2:1) to give 835.5 g (95%) of the titled compound. The structure was identified by $^1$H-NMR.

$^1$H-NMR (500 MHz, CDCl$_3$) δ (ppm)=1.45 (9H, s, Boc), 1.60 (2H, quant, —NHCH$_2$CH$_2$CH$_2$NHBoc), 3.14 (2H, q, —NHCH$_2$CH$_2$CH$_2$NHBoc), 3.31 (2H, q, —NHCH$_2$CH$_2$CH$_2$NHBoc), 3.69 (2H, s, Ph-CH$_2$—CO), 4.93 (1H, s, NH), 6.50-7.60 (9H, m, Aromatic H, NH)

(2) Diaminopropane-diclofenac Hydrochloride

Under ice-cooling, 20 mL of 4 M hydrochloric acid/ethyl acetate was added to 1 mL dichloromethane solution of 825.0 mg (1.82 mmol) of the Boc-propylamide-diclofenac obtained above, followed by stirring for 2 hours. Diethyl ether was added thereto for precipitation, and the precipitate was dried under reduced pressure to give 714.5 mg (101%) of the titled compound. The structure was identified by $^1$H-NMR.

$^1$H-NMR (500 MHz, CDCl$_3$) δ (ppm)=1.90 (2H, t, —NHCH$_2$CH$_2$CH$_2$NH$_2$), 2.99 (2H, t, —NHCH$_2$CH$_2$CH$_2$NH$_2$), 3.26 (2H, d, —NHCH$_2$CH$_2$CH$_2$NH$_2$), 3.71 (2H, s, Ph-CH$_2$—CO), 6.40-7.49 (8H, m, Aromatic H, NH)

Example 41

Synthesis of Diaminopropane-diclofenac-Introduced Sodium Hyaluronate (DS 18.1%)

In 22.5 mL water/22.5 mL dioxane, 200 mg (0.5 mmol/disaccharide unit) of hyaluronic acid having a weight average molecular weight of 800,000 was dissolved, and then 0.2 mL of 2 M HOSu, 0.2 mL of 1 M WSCI·HCl and 1 mL of a solution (water:dioxane=1:1) of 78.4 mg (0.2 mmol) of the diaminopropane-diclofenac hydrochloride obtained in Example 40 were added thereto in this order, followed by stirring overnight. Next, 3 ml of 5% aqueous sodium hydrogen carbonate solution was added thereto, followed by stirring for 4 hours. After neutralization of the reaction solution by adding 86 µl of 50% acetic acid, 1 g of sodium chloride was added thereto, followed by stirring. The mixture was precipitated by adding 200 ml of ethanol, and the precipitate was washed twice with 85% ethanol, twice with ethanol and with diethyl ether and dried at room temperature overnight under reduced pressure to give 206.2 mg of a white solid. The degree of substitution of diclofenac was 18.1% when measured with a spectrophotometer.

Example 42

Preparation of 1% Aminopropanol-ketoprofen-Introduced Sodium Hyaluronate Solution for Performance Test Use To 22 mg of the aminopropanol-ketoprofen-introduced sodium hyaluronate (degree of substitution 26.3%) obtained in Example 3, 5 mM phosphate buffered saline was added to give a total amount of 2.19 g, followed by stirring overnight to prepare a 1% solution. The solution was passed through a 0.45 µm filter and used as the titled solution. When the endotoxin content of this solution was measured by the endotoxin test method (colorimetric method) which is a general test method described in the Pharmacopoeia of Japan, the endotoxin value was 0.0073 EU/M1.

Administration Test

Example 43

Effect of Aminopropanol-ketoprofen-Introduced Sodium Hyaluronate on the Bradykinin-Induced Pain Model in Rats 1) Administration of Test Substances As General anesthesia, inhalation of isoflurane (Forane (registered trade mark), Dainippon Pharmaceutical Co., Ltd., concentration 3.0%, flow rate 2.0 liters/min) filled in a small animal anesthetizer (TK-4, manufactured by BioMachinery Co., Ltd.) was employed.

PBS, 1% sodium hyaluronate solution (HA), a 3.7 mg/ml ketoprofen sodium solution (KP) prepared by dissolving ketoprofen in PBS, and a 1% PBS solution of the aminopropanol-ketoprofen-introduced sodium hyaluronate (KP-HA) prepared in Example 42 were used as the test substances.

Rats (Crj:SD(SPF), male, 7-weeks-old) were fixed in the supine position under ether anesthesia, and a wide area around the knee joint of the left hind paw was shaved with an electric clipper. After disinfecting the area around the joint by spraying 70% alcohol, the above-described test substances were administered into the knee joint cavity of the left hind paw at a dose of 20 µl/joint using a 29 G needle-tipped syringe for insulin use (manufactured by Terumo Corp.). This procedure was performed using 5 cases (n=5) for each test substance group.

2) Administration of Algesic Substance (BK+PGE$_2$ Solution)

After 1 day of the administration of each test substance, rats were fixed in the supine position under no anesthesia. After disinfecting the area around the joint by spraying 70% alcohol, a mixed solution of bradykinin (BK) and prostaglandin E$_2$ (PGE$_2$) as algesic substances was administered into the knee joint cavity of the left hind paw at a dose of 50 µjoint using a 29 G needle-tipped syringe for insulin use (manufactured by Terumo Corp., thickness of the needle is 0.33 mm). Additionally, this algesic substance solution was produced in such a manner that the final concentrations of BK and PGE$_2$ became 4 µg/ml and 2 µg/ml, respectively. Pain reactions were visually observed right after the administration of the algesic agent.

3) Pain Observation

For about 2 minutes after administration of the algesic substances, the behavioral manifestations in gait such as "lifting the foot", "walking on three legs" and "claudication" were visually observed and scored. The pain scores were assigned as lifting the foot: 1 point addition and claudication or walking on three legs: 1 point addition, and evaluated by a stage of from 0 to 2 points. In addition, the evaluation was performed under blinded conditions. A graph in which pain reactions of respective individuals were scored is shown in FIG. 1.

In FIG. 1, the results are shown by average pain score±standard deviation.

Consequently, the pain suppressing effects were observed in order of KP-HA>KP>HA, in comparison with the PBS administration group.

Example 44

Effects of Intra-Articular Injection of Aminopropanol-Ketoprofen-Introduced Sodium Hyaluronate on the 1% Silver Nitrate-Induced Pain Model in Rats 1) Administration of Pain Inducing Substances As General anesthesia, inhalation of isoflurane (Forane (registered trade mark), Dainippon Pharmaceutical Co., Ltd., concentration 3.0%, flow rate 2.0 liters/min) filled in a small animal anesthetizer (TK-4, manufactured by BioMachinery Co., Ltd.) was employed.

Rats (Crj:SD (SPF), male, 6-weeks-old) were fixed in the supine position under ether anesthesia, and a wide area around the knee joint of the left hind paw was shaved with an electric clipper. After disinfecting the area around the joint by spraying 70% alcohol, 1% silver nitrate solution was administered into the knee joint cavity of the left hind paw at a dose of 50 μl/joint using a 29 G needle-tipped syringe for insulin use (manufactured by Terumo Corp.).

2) Administration of Test Substances

As the test substances, 1% sodium hyaluronate solution (HA) and 1% solution of the aminopropanol-ketoprofen-introduced sodium hyaluronate (KP-HA) prepared in Example 42, each using PBS as the solvent, were prepared. Rats were divided into 2 groups, each including 5 animals, and each test substance was administered to respective groups on 24 hours after the administration of 1% silver nitrate solution. Regarding the administration method, as in the case of algesic substances, the area around the joint was disinfected by spraying 70% alcohol under inhalation anesthesia by isoflurane, and each test substance was administered into the knee joint cavity of the left hind paw at a dose of 40 μjoint using a 29 G needle-tipped syringe for insulin use (n=5).

3) Evaluation method

The walking of each group was visually observed and scored by using the following pain score table which was figured walking in score under blinded conditions. The results are shown in FIG. 2.

Figure 2:
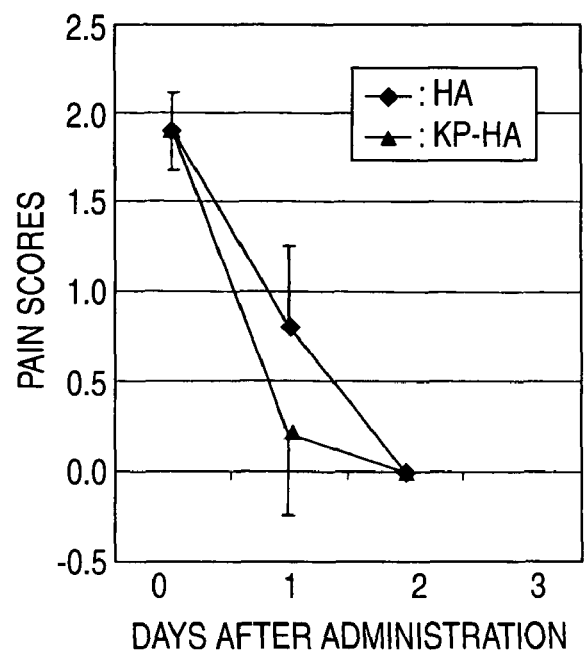
FIG. 2 is a graph showing pain scores on the 1% silver nitrate solution-induced pain model in rat.

In FIG. 2, the results are shown by average pain score standard deviation.

Figure 3:
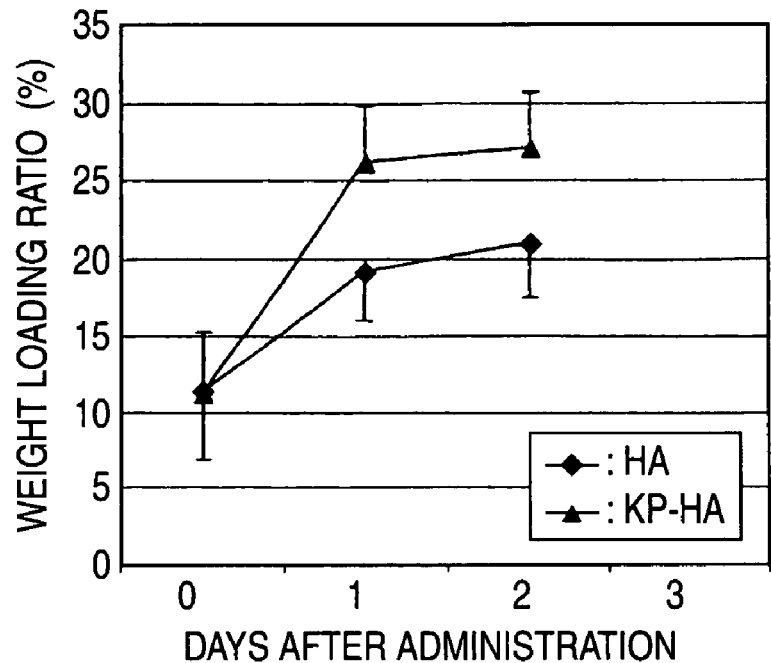
FIG. 3 is a graph showing a weight loading ratio (%) on the 1% silver nitrate solution-induced pain model in rat.

Score
0: Normal (includes nearly normal)
1: Mild claudication
2: Severe claudication
3: Walking on three legs In addition, the weight loading on the silver nitrate-injected paw (left hind paw) was measured by using a weighting activity analgesia meter (manufactured by Tokken Inc.), and the weight loading rate was calculated by dividing the measured value by the body weight. (Incidentally, weight loading rate was about 32% at the normal animals.) The measurement was performed once a day until 2 days after the administration of each test substance. The results are shown in FIG. 3.

As shown in FIG. 2, the pain score was gradually reduced in both of the HA administration group and KP-HA administration group, but the degree of pain relief (degree of recovery from pain) was quicker in the KP-HA administration group than the HA administration group. In addition, the weight loading rate generally becomes high as the recovery from pain progresses on the measurement of the rate, but as shown in FIG. 3, the weight loading rate became significantly higher within a short period of time in animals given KP-HA compared to those given HA. Relationship between the KP-HA group and the HA group in the results of FIG. 2 and FIG. 3 was the same.

Example 45

Examination on the Sustained Release Property of NSAIDs-Introduced Hyaluronic Acid in the Rabbit Knee Joint 1) Administration Method of Test Substances The 1% aminopropanol-ketoprofen-introduced sodium hyaluronate solution (KP-HA) obtained in Example 42, a ketoprofen solution (KP) in which 1.42 mg of ketoprofen was dissolved in 1 ml of PBS, and a mixed solution of ketoprofen and HA (KP+HA) in which 1.41 mg of ketoprofen was dissolved in 1 ml of 1% HA solution were used as the test substances.

Using five rabbits for each test substance, rabbits were fixed in the supine position under ketamine general anesthesia (1 ml/head, i.v.), and a wide area around the knee joint of the left hind paw was shaved with an electric clipper. Each of the above-described test substances was administered into the joint cavity from outside of the rabbit knee at a dose of 300 μl using a 1 ml syringe equipped with a 25 G needle (manufactured by Terumo Corp., thickness of the needle is 0.5 mm).

Autopsy was performed on 6, 12, 24 hours and 2, 4 days after administration of test substances.

2) Measuring Method of the Amounts of Free Type KP and Binding Type KP in Synovial Fluid The rabbits were sacrificed by exsanguination under ketamine general anesthesia. After all synovial fluid was collected, the joint cavity was washed 2 times with 2 mL saline into the joint cavity of the dissected knee using a 25 G needle. The wash fluids were also collected. Amounts of KP and HA-KP in the synovial fluid combined with the recovered wash fluids were measured by the following procedure.

By adding 1 N HCl (0.2 ml) to the synovial fluid (4 ml vol.), hydrochloric acid acidity was confirmed, and then ethyl acetate having the same volume of the solution was added and vigorously stirred and the upper organic layer was recovered. This extraction operation was performed 3 times in total. An acetonitrile solution was added to the recovered organic layer to make it into an acetonitrile solution, and the amount of free KP was measured by using HPLC (Amount of free type KP in synovial fluid).

Next, the water layer obtained by the above-described extraction operation was adjusted to strongly basic state by adding 1 N NaOH and stirred at room temperature for 1 hour. Subsequently, the water layer was ice-cooled, adjusted to hydrochloric acid acidic state by slowly adding 4 N HCl while stirring, and then vigorously stirred by adding ethyl acetate having the same volume of the solution to recover the upper organic layer. This extraction operation was performed 3 times in total. An acetonitrile solution was added to the recovered organic layer to make it into an acetonitrile solution, and the amount of HA-KP (amount of binding type KP) was measured by using HPLC (Amount of bound HA-KP in synovial fluid).

3) Measuring Method of the Amount of KP in the Digestive Fluid of Synovium

Synovium was separated and collected from the knee joint after recovery of the synovial fluid of the above-described (2). The collected synovium was thoroughly washed with 100 ml of saline to completely remove the adherent synovial fluid. After removing the patella, the synovium was put into a tube, 5 ml of proteinase K (Lot No. 102K8633, manufactured by SIGMA) prepared to be a concentration of 2 mg/ml with 10 mM sodium acetate solution (pH 7.5) was added thereto, and enzyme digestion was performed at 55° C. for 41 hours while optionally stirring using Vortex. After the digestion, the enzyme was deactivated by incubating at 100° C. for 5 minutes, and the amount of KP in the thus obtained digestive fluid was measured by the following procedure.

A ¼ volume of 4 N NaOH was added to the thus obtained digestive fluid and stirred at room temperature for 1 hour. Subsequently, the solution was ice-cooled, adjusted to hydrochloric acid acidic state by slowly adding 4 N HCl, and then vigorously stirred by adding diethyl ether having the same volume of the solution to remove the upper organic layer. This degreasing operation was performed 3 times in total. Under ice-cooling, 4 N HCl was added to the solution after the degreasing operation and stirred to confirm hydrochloric acid acidic state and then vigorously stirred by adding ethyl acetate having the same volume of the solution to recover the upper organic layer. This extraction operation was performed 3 times in total. An acetonitrile solution was added to the thus recovered organic layer to make it into an acetonitrile solution, and the amount of free KP was measured by using HPLC.

Figure 4:
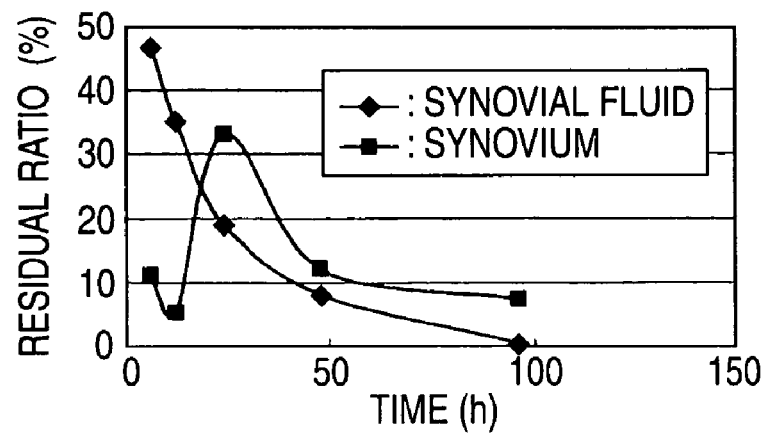
FIG. 4 is a graph showing a residual ratio in rabbit knee joint with time by the administration of aminopropanol-ketoprofen-introduced sodium hyaluronate (KP-HA), a mixture of ketoprofen and HA, and ketoprofen to rabbit knee joint.

Amount of Free Type KP in Synovium Digestive Fluid:

Residual ratios of KP and HA-KP in the synovial fluid and synovium digestive fluid were calculated with time. (Table 1, FIG. 4)

ovium rapidly and exert the effect by transferring to the synovium. Thus, it is considered that keeping of NSAIDs concentration in the synovium is greatly concerned in the long-lasting analgesic effect and sustained release effect. As shown in the above table, when KP (single drug) was administered, it disappeared from the synovium within 6 hours by its passing through the synovium and metabolism. However, when KP-HA (conjugate) was administered, KP was persistently maintained also in the synovium, thus indicating that this is more effective as sustained release preparations of NSAIDs.

Example 46

Effects of Intra-Articular Injection of Aminopropanol-diclofenac-Introduced Sodium Hyaluronate Having Different Degree of Substitution (DS) on the 1% Silver Nitrate Induced Pain Model in Rats Evaluation of the intra-articular injection of the following test substances was performed in accordance with the procedure in the above Example 44.

Test Substances:

(i) PBS solution of 1% aminopropanol-diclofenac-introduced sodium hyaluronate (DS 18.2%) obtained in Example 19

(ii) PBS solution of 1% aminopropanol-diclofenac-introduced sodium hyaluronate (DS 9.7%) obtained in Example 36

(iii) PBS solution of 1% aminopropanol-diclofenac-introduced sodium hyaluronate (DS 4.3%) obtained in Example 35

(iv) PBS

In the same manner as in the above Example 44, the walking of each group was visually observed and scored by using the pain score table which was figures walking in score under

TABLE 1

| Test substance | Sample | Existing form | 6 hours (%) | 12 hours (%) | 24 hours (%) | 2 days (%) | 4 days (%) |
|---|---|---|---|---|---|---|---|
| KP (single drug) | synovial fluid | Free type KP | 0 | | | | |
| | synovium | | 0 | | | | |
| KP + HA (mixture) | synovial fluid | Free type KP | 0.07 | 0 | | | |
| | synovium | | 0 | 0 | | | |
| KP – HA (conjugate) | synovial fluid | Free type KP | 0.13 | 0.14 | 0.22 | 0.16 | 0 |
| | | Binding type KP | 46.56 | 34.94 | 18.95 | 8.11 | 0.63 |
| | synovium | | 11.3 | 5.20 | 32.90 | 12.10 | 7.40 |

When KP (single drug) or KP+HA (mixture) was administered as the test substance, KP disappeared from the synovial fluid and synovium within 6 hours and 12 hours. However, when the KP-HA (conjugate) as a substance of the present invention was administered, the presence of KP was confirmed in both of the synovial fluid and synovium even after 4 days, so that it was considered that KP shows its long-lasting effect by persistently presenting in the administered site.

Figure 5:
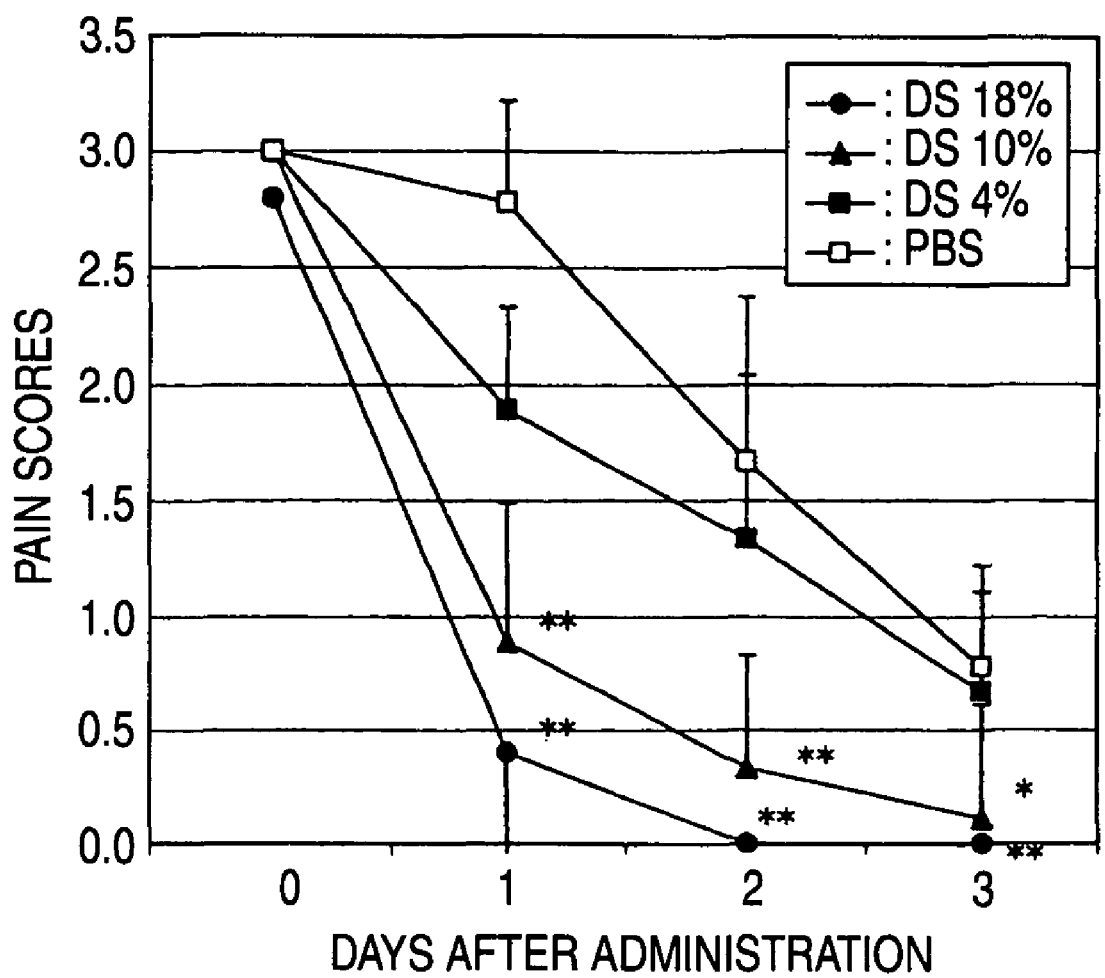
FIG. 5 is a graph showing effect of aminopropanol-diclofenac-introduced sodium hyaluronate having different degree of substitution (DS) on the 1% silver nitrate solution induced pain model in rat.

It is presumed that the joint pain is generated not via a cartilage which is an aneurogenic tissue but via a synovium, and in addition, it is considered that when NSAIDs are administered into a joint cavity, NSAIDs are penetrated into a synblinded conditions. The results are shown in FIG. 5. The results are shown by average pain score±standard deviation, and the DS 18%, DS 10% and DS 4% respectively correspond to DS 18.2%, DS 9.7% and DS 4.3%. In addition, in FIG. 5, * indicates that there is a significant difference against PBS with a level of significance of $0.01 \leq p \leq 0.05$, and ** indicates that there is a significant difference against PBS with a level of significance of $p < 0.01$.

Consequently, all of the diclofenac-introduced sodium hyaluronate derivatives of DS 18.2%, DS 9.7% and DS 4.3% as the test substances showed analgesic effect. Particularly, the test substances of DS 18.2% and DS 9.7% showed a remarkable analgesic effect in comparison with PBS.

In addition, the analgesic effect was improved dependently on the increase of the degree of substitution (DS) of diclofenac.

Reference Example 6

Effects of Oral Administration of Diclofenac Sodium on the 1% Silver Nitrate Induced Pain Model in Rats The test was performed in accordance with the procedure in the above Example 44, and the following test substances was orally administered and evaluated. Test substances were orally administered by using a sonde for oral administration to rat (manufactured by Fuchigami Kikai) at a dose of 1 ml/head.

Test Substances:

(i) 1% diclofenac sodium suspension (10% gum arabic)

(ii) 0.02% diclofenac sodium suspension (10% gum arabic)

Additionally, the (i) (high dose group) corresponds to the administration of 50 mg/kg as diclofenac sodium, and the (ii) (low dose group) corresponds to the administration of 1 mg/kg as diclofenac sodium which is almost the same amount of the clinical dose.

Figure 6:
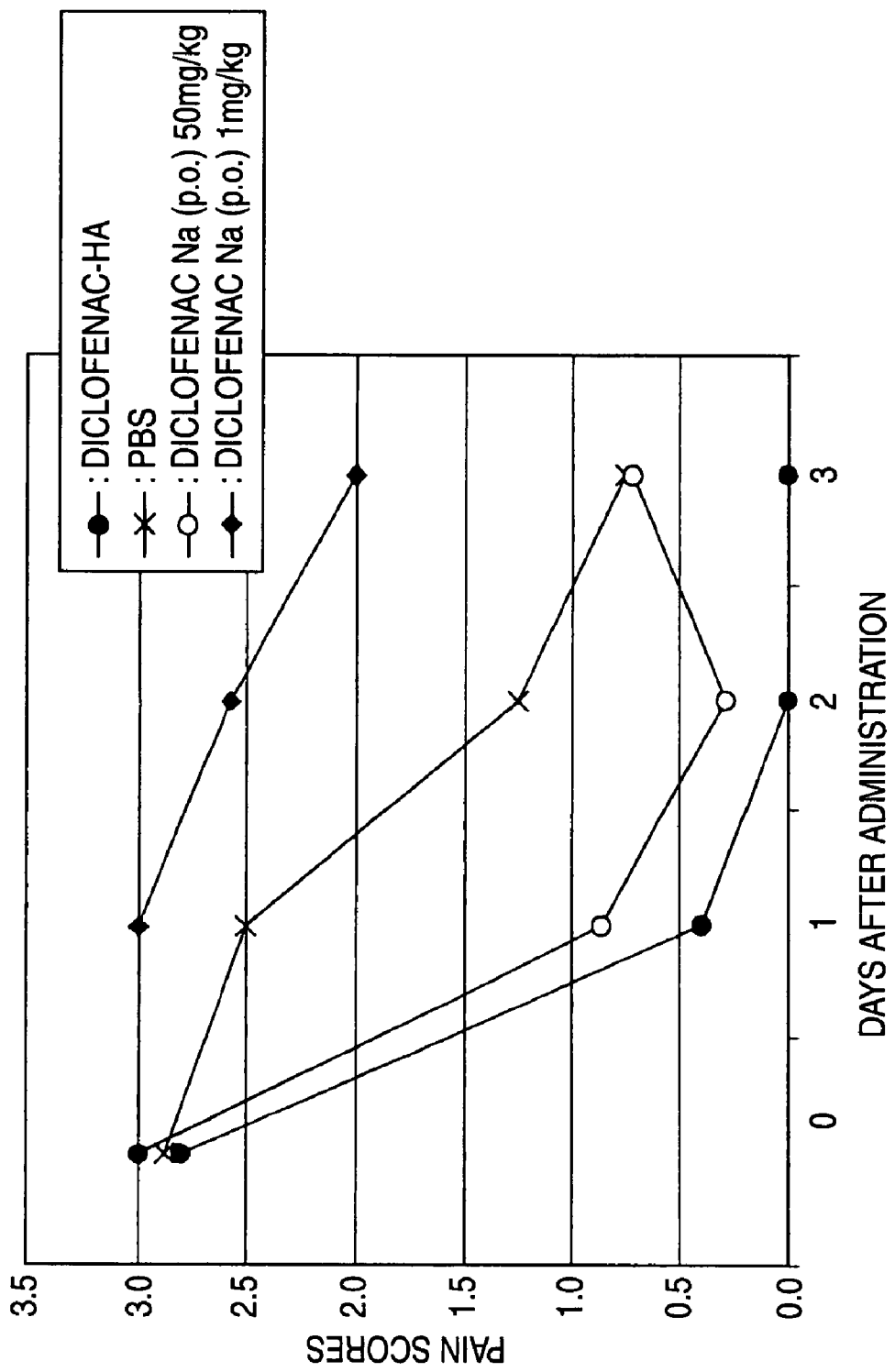
FIG. 6 is a graph showing effect of oral administration of diclofenac sodium on the 1% silver nitrate solution induced pain model in rat.

In the same manner as in the above Example 46, the walking of each group was visually observed and scored by using the pain score table which was figured walking in score under blinded conditions. The results are shown in FIG. 6. In FIG. 6, the "Diclofenac Na (p.o.) 50 mg/kg" corresponds to the above-described (i) (high dose group), and the "Diclofenac Na (p.o.) 1 mg/kg" corresponds to the above-described (ii) (low dose group). Additionally, the results of pain scores by intra-articular injection of the diclofenac-introduced hyaluronic acid derivative (DS 18.2%) and PBS, measured in the above Example 46, were also described as references in FIG. 6 as "Diclofenac-HA" and "PBS", respectively.

Consequently, oral administration of the high dose (50 mg/kg) of diclofenac sodium showed analgesic effect, however positive fecal occult blood reaction, jaundice-like symptom and body weight loss were observed from the next day. The dose of the high dose group is scores of times larger than the clinical dose, and is not a practical dose in terms of adverse effects and toxicity.

In the low dose group (1 mg/kg) with oral administration, which is almost the clinical dose, the effect was not found in comparison with the PBS intra-articular injection group.

On the other hand, intra-articular injection of the diclofenac-introduced hyaluronic acid derivative showed the analgesic effect after the administration. Additionally, the adverse effect caused by oral administration of the high dose (50 mg/kg) of diclofenac sodium was not observed, so that its high availability was confirmed.

Reference Example 7

Effects of Intra-Articular Injection of Diclofenac Single Drug and Hyaluronic Acid on the 1% Silver Nitrate Induced Pain Model in Rats The test was performed in accordance with the procedure in the above Example 44, and the following test substances were intra-articulately administered and evaluated.

Figure 7:
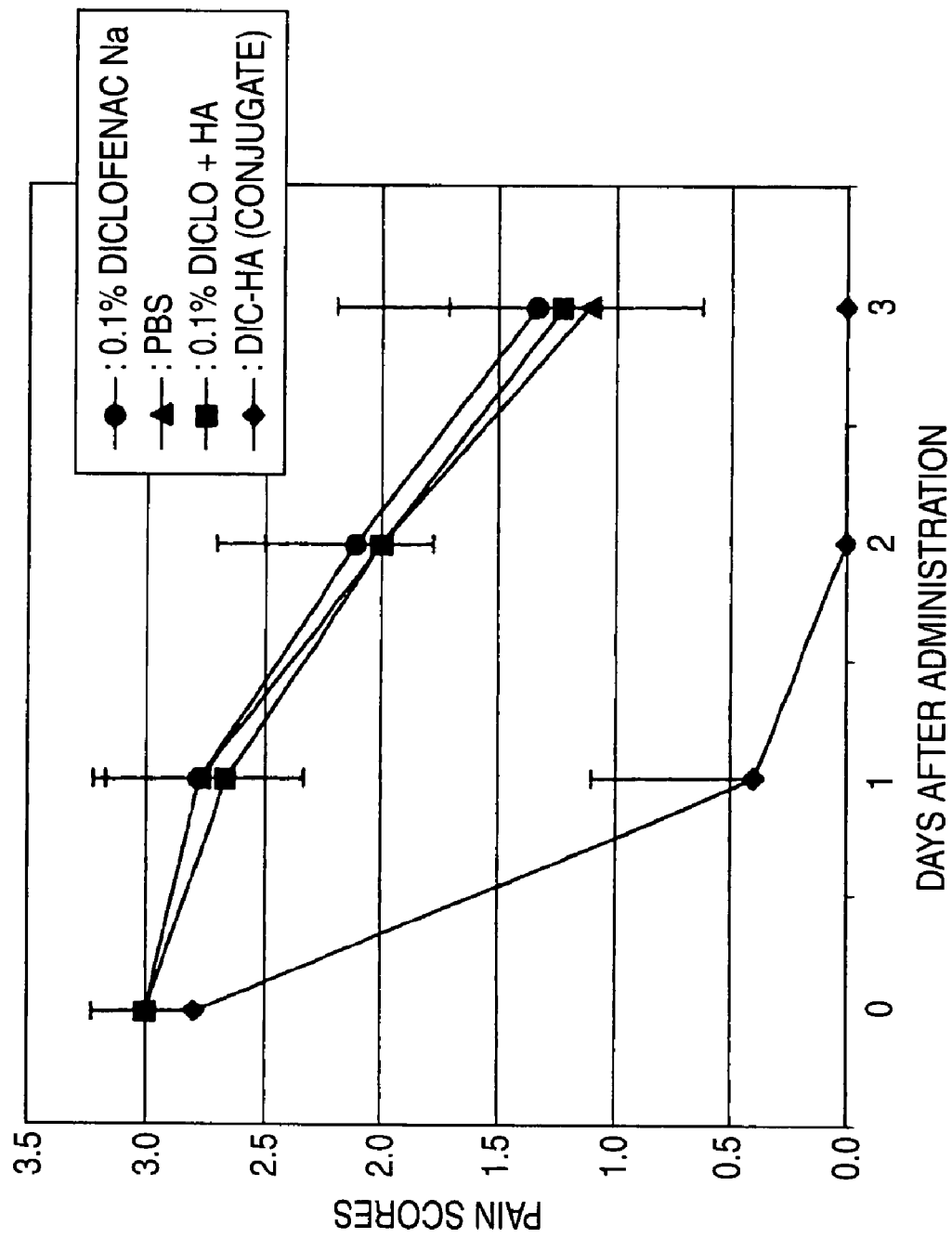
FIG. 7 is a graph showing effects of diclofenac single drug and hyaluronic acid on the 1% silver nitrate solution induced pain model in rat.

Test Substances:

(i) 0.1% diclofenac solution (ii) 0.1% diclofenac/1% hyaluronic acid mixed solution (iii) PBS In the same manner as in the above Example 46, the walking of each group (n=9) was visually observed and scored using the pain score table which was figured walking in score under blinded conditions. The results are shown in FIG. 7. In FIG. 7, the results are shown by average pain score±standard deviation, and the "0.1% Diclofenac Na" corresponds to the above-described (i) 0.1% Diclofenac solution, and the "0.1% Diclo+HA" to the above-described 0.1% diclofenac/1% hyaluronic acid mixed solution. Additionally, the results of the diclofenac-introduced hyaluronic acid derivative (DS 18.2%) measured in the above Example 46 were also described as references in FIG. 7 as "Dic-HA (conjugate)".

Consequently, the diclofenac single drug and the mixture of diclofenac and hyaluronic acid did not show significant effect in comparison with PBS as the control group.

Example 47

Effects of Intra-Articular Injection of Aminopropanol-Diclofenac-Introduced Sodium (65 kDa) Hyaluronate, Diaminopropane-Diclofenac-Introduced Sodium Hyaluronate and Aminoethanol-Diclofenac-Introduced Sodium Hyaluronate on the 1% Silver Nitrate Induced Pain Model in Rats The test was performed in accordance with the procedure in the above Example 44, and the following test substances were intra-articularly administered and evaluated.

Test Substances:

(i) PBS solution of the 1% aminopropanol-diclofenac-introduced sodium (65 kDa) hyaluronate obtained in Example 37

(ii) PBS solution of the 1% diaminopropane-diclofenac-introduced sodium hyaluronate obtained in Example 41

(iii) PBS solution of the 1% aminoethanol-diclofenac-introduced sodium hyaluronate obtained in Example 39

(iv) PBS

Figure 8:
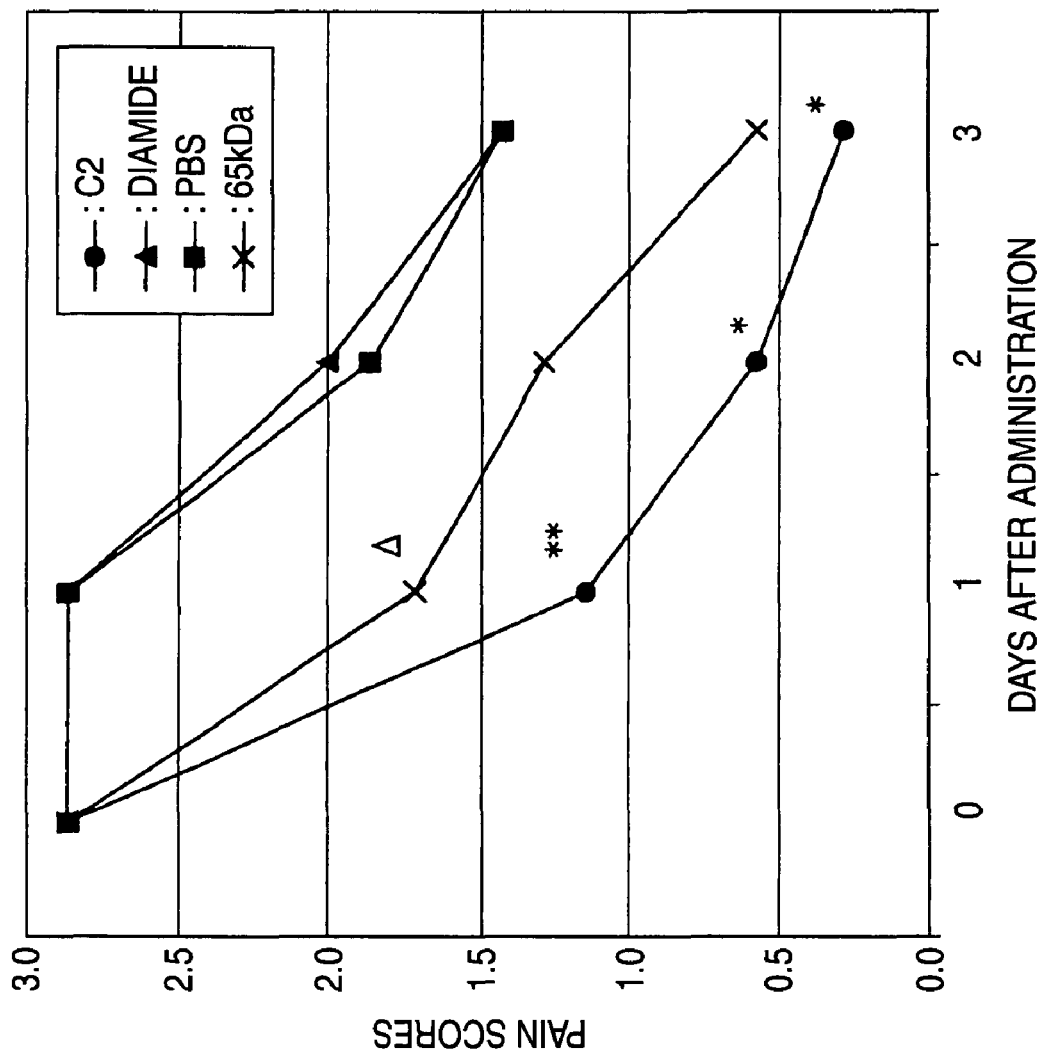
FIG. 8 is a graph showing comparison of the effects of aminopropanol-diclofenac-introduced sodium hyaluronate (65 kDa), diaminopropane-diclofenac-introduced sodium hyaluronate, and aminoethanol-diclofenac-introduced sodium hyaluronate on the 1% silver nitrate solution induced pain model in rat.

In the same manner as in the above Example 44, the walking of each group (n=7) was visually observed and scores by using the pain score table which was figured walking in score under blinded conditions. The results are shown in FIG. 8. In FIG. 8, the results are shown by average pain score, and the "65 kDa" corresponds to the above-described (i) PBS solution of the 1% aminopropanol-diclofenac-introduced sodium (65 kDa) hyaluronate, and the "diamide" to the above-described (ii) PBS solution of the 1% diaminopropane-diclofenac-introduced sodium hyaluronate and the "C2" to the above-described (iii) PBS solution of the 1% aminoethanol-diclofenac-introduced sodium hyaluronate. In addition, in FIG. 8, Δ indicates that there is a significant difference against PBS with a level of significance of $0.05 < p < 0.1$, * indicates that there is a significant difference against PBS with a level of significance of $0.01 < p < 0.05$, and ** indicates that there is a significant difference against PBS with a level of significance of $p < 0.01$.

Consequently, the aminoethanol-diclofenac-introduced sodium hyaluronate solution which used aminoethanol, wherein the number of spacer carbons is smaller than aminopropanol by a factor of 1, also showed remarkable analgesic effect. However, the diaminopropane-diclofenac-introduced sodium hyaluronate solution, in which diclofenac was introduced through an amide bond, had no effect on the test system of this example. In addition, the diclofenac-introduced hyaluronic acid derivative, which used a hyaluronic acid having a molecular weight of 65 kDa, showed diminished analgesic effect in comparison with the case of the molecular weight of 800,000.

These results showed that the analgesic effect depends on the binding form with diclofenac or the molecular weight of hyaluronic acid.

Example 48

Effects of Diclofenac Sodium Single Drug and Diclofenac-Introduced Hyaluronic Acid Derivative on COX-2 (In Vitro)

The COX-2 inhibitory activity of the following test substances was evaluated using Chemiluminescent COX Inhibitor Screening Assay Kit (Cayman) (a kit for screening inhibitors using the peroxidase activity of sheep-derived COX-2 as the index).

Test Substances:

(i) aminopropanol-diclofenac-introduced sodium hyaluronate aqueous solution obtained in Example 19 (Dic-C3-HA) (corresponds to 200 µg/ml HA, corresponds to 80 µM Diclofenac)

(ii) aminoethanol-diclofenac-introduced sodium hyaluronate aqueous solution obtained by the same procedure of Example 39 (Dic-C2-HA, DS 18.5%) (corresponds to 200 µg/ml HA, corresponds to 80 µM Diclofenac)

Figure 9A:
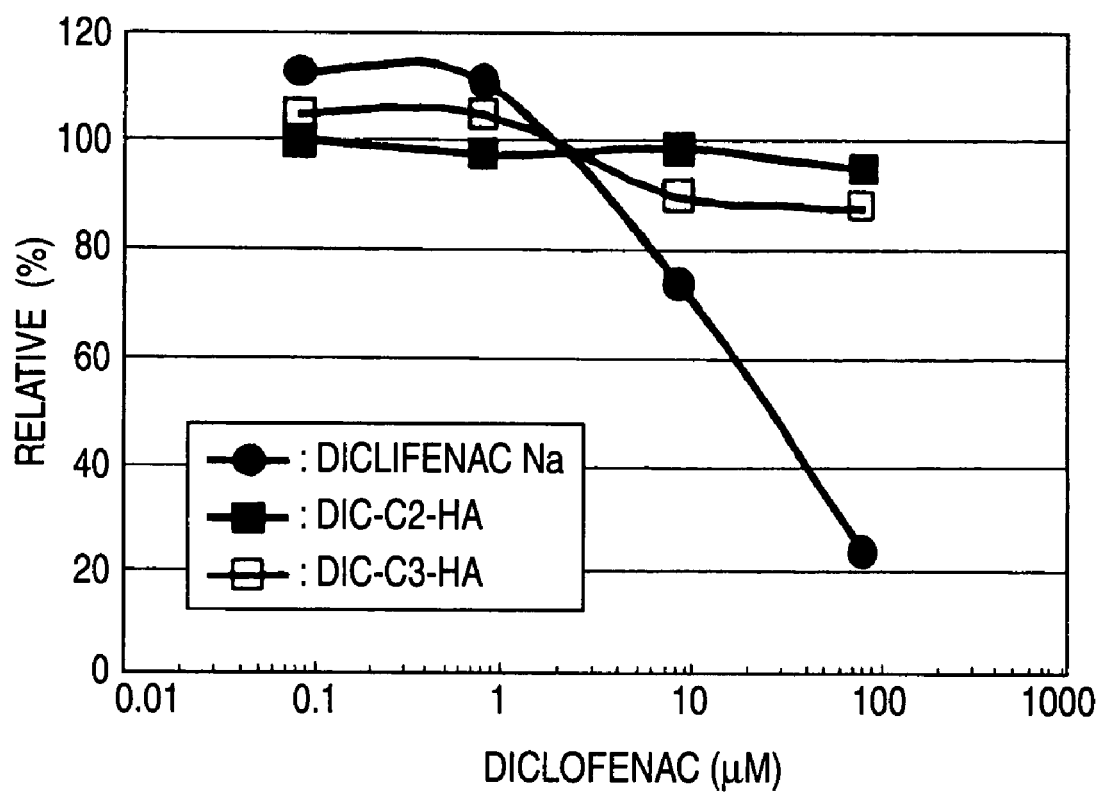
FIG. 9(a) is a graph showing effects (in vitro) of diclofenac sodium single drug and diclofenac-introduced hyaluronic acid derivatives on COX-2.
Figure 9B:
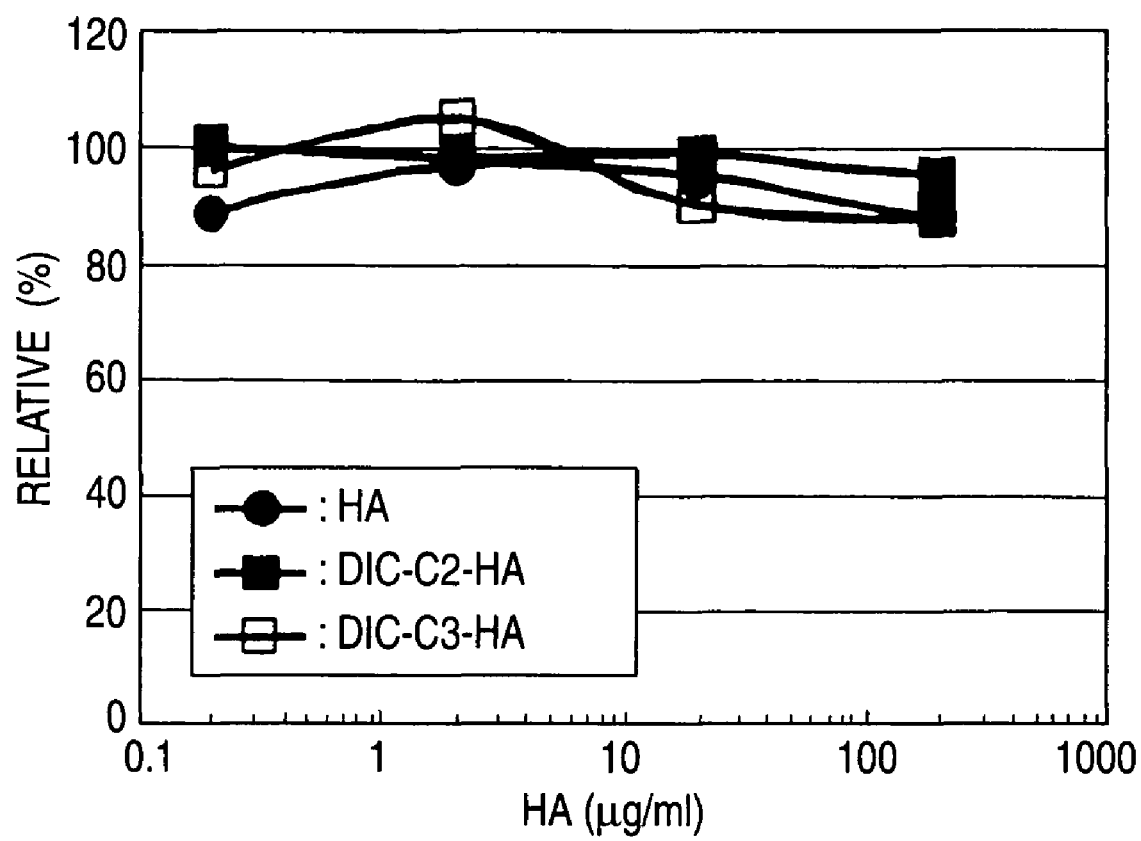
FIG. 9(b) is a graph showing effects (in vitro) of sodium hyaluronate single drug and diclofenac-introduced hyaluronic acid derivatives on COX-2.

(iii) 80 µM diclofenac sodium aqueous solution (iv) 200 µg/ml sodium hyaluronate (HA) aqueous solution By preparing stock solutions of the above-described various test substances and these test substances further diluted 10 times, 100 times and 1000 times with distilled water, their COX-2 inhibitory activities were measured by using the COX Inhibitor Screening Assay Kit (nontreated group n=6, test substance group n=3). The enzyme activity value of each treated group was expressed as a relative % by the following formula based on the COX-2 enzyme activity of the nontreated group which was defined as 100%. The results are shown in FIG. 9(a) and FIG. 9(b). In FIG. 9(a), the "Diclofenac Na" corresponds to the above-described diclofenac sodium aqueous solution, and the "Dic-C3-HA" to the above-described aminopropanol-diclofenac-introduced sodium hyaluronate aqueous solution, and the "Dic-C2-HA" to the above-described aminoethanol-diclofenac-introduced sodium hyaluronate aqueous solution. In FIG. 9(b), the "HA" corresponds to the above-described 200 µg/ml sodium hyaluronate aqueous solution.

Enzyme activity value (%)=(test substance-treated group)/nontreated group×100

Consequently, the diclofenac-introduced hyaluronic acid derivatives (Dic-C3-HA and Dic-C2-HA) containing diclofenac, at a concentration corresponding to the concentration at which the diclofenac sodium single drug showed obvious COX-2 inhibitory activity, did not show the COX-2 inhibitory activity. The HA single drug also did not show the COX-2 inhibitory activity. These results suggested that the effect of the diclofenac-introduced hyaluronic acid derivatives in vivo is not the action of itself but may be referred from the diclofenac released from HA.

As one of the reasons why the effect of the diclofenac-introduced hyaluronic acid derivatives in vivo (Examples 46 and 47) is superior to that of the diclofenac single drug, it is considered that HA carries a further larger amount of diclofenac to the COX-2 in the target cell due to its affinity for the cell.

Example 49

Effects of Diclofenac-Introduced Hyaluronic Acid Derivative on the Adjuvant-Induced Arthritis (AIA) Model in Rats 1) Adjuvant Induction After heating 6 mg/ml *Mycobacterium butyricum* (Lot No. 2115687, Difco) at 121° C. for 20 minutes in an autoclave, it was injected into the footpad of the right hind paw at a dose of 50 µl/joint, with a 29 G needle-tipped syringe for insulin use (Terumo).

2) Administration of Test Substances
Test Substances:

(i) PBS solution of the 1% aminopropanol-diclofenac-introduced sodium (DS 18%) hyaluronate obtained in Example 19 (Diclofenac-HA)

(ii) PBS

As in the case of the adjuvant injection, the above-described test substances were administered under no anesthesia into the tibio-tarsal joint cavities of both paws at a dose of 50 µl/joint with a 29 G needle-tipped syringe for insulin use (Terumo), immediately after the adjuvant injection and on weeks 1, 2 and 3 after the injection (4 times in total) (n=14).

4) Evaluation

Evaluation was performed prior to injection of the adjuvant and on days 3, 5, 7, 10, 12, 14, 21 and 28 after the injection.
Body weight
Volumes of both hind paws (an equipment for measuring the volume of hind-paw edema in rats and mice (TK-101CMP) manufactured by Unicom)

5) Results

Figure 10A:
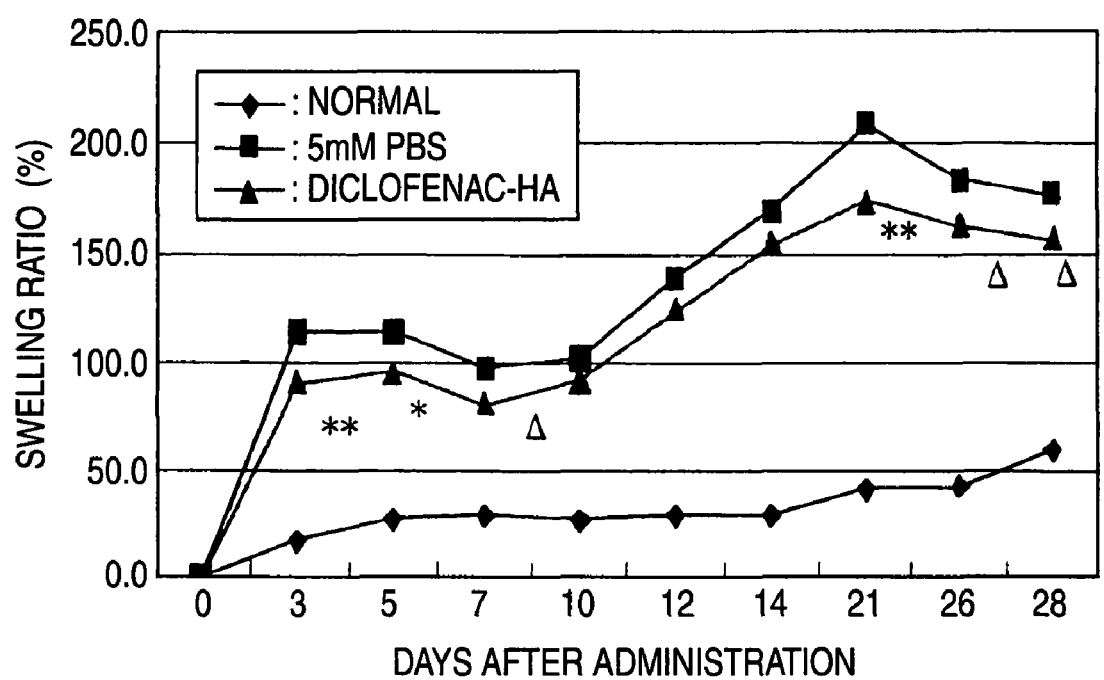
FIG. 10 (a) is a graph showing effect of the administration of diclofenac-introduced hyaluronic acid derivative on adjuvant-injected paw on the adjuvant-induced arthritis (AIA) model in rat.
Figure 10B:
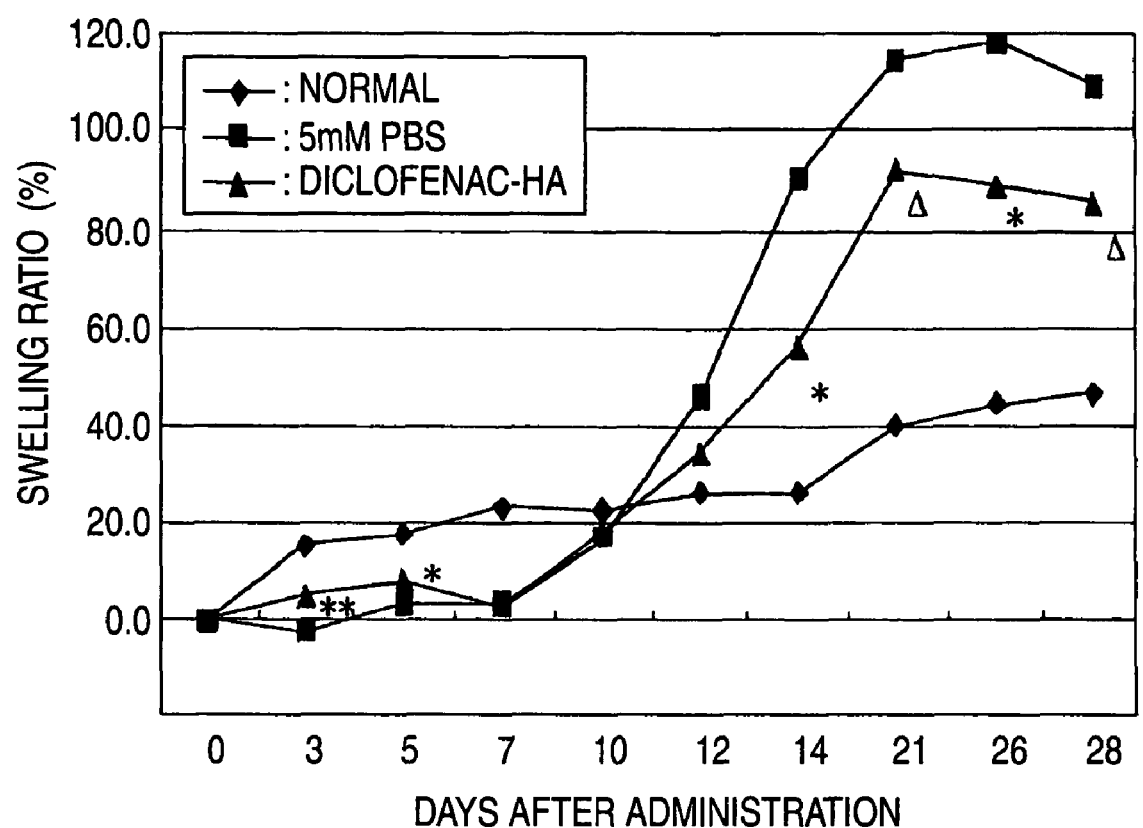

Swelling ratio of the adjuvant-injected paws and non-injected paws was measured by the following formula. Results of the swelling ratio of the adjuvant-injected paws are shown in FIG. 10(a), and results of the swelling ratio of the adjuvant-non-injected paws in FIG. 10(b). In FIG. 10, the "Diclofenac-HA" means the above-described (i) PBS solution of 1% aminopropanol-diclofenac-introduced sodium (DS 18%) hyaluronate, and the "normal" means adjuvant- and test substance-non-administered groups. In FIG. 10, Δ indicates that there is a significant difference against PBS with a level of significance of $0.05 < p < 0.1$, and * indicates that there is a significant difference against PBS with a level of significance of $0.01 < p < 0.05$, and ** indicates that there is a significant difference against PBS with a level of significance of $p < 0.01$.

Swelling ratio (%)=(paw volume on the measured day−paw volume prior to the adjuvant induction)/volume prior to the adjuvant induction×100

Edema was observed on the injected paw (R) from Day 3 after the adjuvant induction, and the Diclofenac-HA showed the effect to suppress the edema volume on Day 3, Day 5 and Day 21 postinduction, statistically significantly in comparison with the PBS group, and also on Day 7, Day 26 and Day 28 although not significant. Also at other time points, the Diclofenac-HA group showed low values at each time point although not significant.

An obvious swelling (secondary inflammation) was observed on the non-injected paw (L) from Day 14 postinduction. Diclofenac-HA statistically significantly suppressed this edema on Day 14 and Day 26 postinduction. Furthermore, it showed tendency to suppress the edema on Day 21 and Day 28 although not significant.

In addition, since the rat adjuvant-induced arthritis (AIA) model is generally used as a model of rheumatoid arthritis which is arthritis caused by an autoimmune disease, it is speculated that the substance of the present invention exert the effect on rheumatoid arthritis.

While the invention has been described in detail and with reference to specific embodiments thereof, it will be apparent to one skilled in the art that various changes and modifications can be made therein without departing from the spirit and scope thereof.

This application is based on Japanese patent application No. 2004-2478 filed on Jan. 7, 2004 the entire contents of which are incorporated hereinto by reference. All references cited herein are incorporated in their entirety.

INDUSTRIAL APPLICABILITY

According to the present invention, there are provided NSAIDs-introduced hyaluronic acid derivatives in which NSAIDs are bound to hyaluronic acid through a covalent bond via a spacer having a biodegradable region, DMARD-introduced hyaluronic acid derivatives in which DMARD is bound thereto through a covalent bond in the same manner, and pharmaceutical agents which comprise these derivatives as an active ingredient. Since the NSAIDs-introduced hyaluronic acid derivatives and DMARD-introduced hyaluronic acid derivatives are sufficiently dissolved in buffers which are used as the solvents of injection products and the like, they can be used as injection products which can be administered directly to the affected site. Furthermore, the pharmaceutical agent of the present invention can be used for the treatment of arthritis, suppression of inflammation and suppression of pain, and its parenteral administration or topical administration (e.g., intra-articular administration) as fillers is also possible.

The invention claimed is:

1. A hyaluronic acid compound in which a non-steroidal anti-inflammatory drug is bound to hyaluronic acid through a covalent bond, wherein a partial structure of a hyaluronic acid disaccharide unit into which the anti-inflammatory drug is introduced is represented by the following formula (1):

$$Y\text{—}CO\text{—}NH\text{—}R^1\text{—}(O\text{—}R^2)_n \quad (1)$$

wherein Y—CO— represents the glucuronic acid residue of the hyaluronic acid disaccharide unit;
$R^2$ represents a hydrogen atom or a non-steroidal anti-inflammatory drug residue, and at least one $R^2$ is a non-steroidal anti-inflammatory drug residue;
—NH—$R^1$—(O—)$_n$ represents a spacer residue in a spacer compound represented by $H_2N$—$R^1$—(OH)$_n$ having n numbers of a hydroxyl group;
$R^1$ represents a linear or branched hydrocarbon group having from 2 to 12 carbon atoms which may have a substituent;
—CO—NH— represents an amide bond of a carboxyl group in the glucuronic acid as a constituting saccharide of the hyaluronic acid with an amino group in the spacer compound;
wherein a hydroxyl group in the spacer compound forms an ester bond with a carboxyl group in the non-steroidal anti-inflammatory drug residue; and
n is an integer of from 1 to 3, wherein the hyaluronic acid compound has a degree of substitution of the non-steroidal anti-inflammatory drug of from 5 to 50 mol % per repeating disaccharide unit of hyaluronic acid, and the carbonyl group in a hyaluronic acid residue constituting the hyaluronic acid compound is present as an amide bond participating in the binding with the spacer-binding anti-inflammatory drug residue or as a free carboxyl group not participating therein, according to the degree of substitution of the non-steroidal anti-inflammatory drug residue.

2. The hyaluronic acid compound according to claim 1, wherein the non-steroidal anti-inflammatory drug is selected from the group consisting of ketoprofen, naproxen, ibuprofen, flurbiprofen, acetylsalicylic acid, felbinac, fenbufen, mefenamic acid, diclofenac and etodolac.

3. The hyaluronic acid compound according to claim 1, wherein the non-steroidal anti-inflammatory drug is a compound represented by the following formula (2):

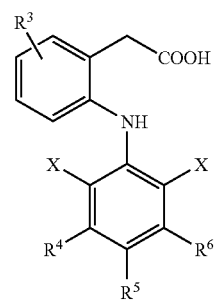

(2)

wherein,
$R^3$ represents a substituent selected from the group consisting of a lower alkyl group, a lower alkoxyl group, and a hydrogen atom;
$R^4$, $R^5$ and $R^6$ each independently represents a substituent selected from the group consisting of a lower alkyl group, a lower alkoxyl group, a hydroxyl group, a halogen atom, and a hydrogen atom; and
each X is the same or different and each represents a substituent selected from the group consisting of a lower alkyl group, a trifluoromethyl group, and a halogen atom, wherein at least one of X is a halogen atom.

4. The hyaluronic acid compound according to claim 3, wherein the non-steroidal anti-inflammatory drug is a compound represented by the following formula (7):

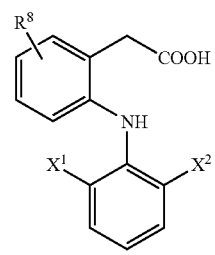

(7)

wherein $R^8$ represents a substituent selected from the group consisting of a lower alkyl group, a lower alkoxyl group, and a hydrogen atom; and
$X^1$ and $X^2$ each independently represents a substituent selected from the group consisting of a lower alkyl group, a trifluoromethyl group, and a halogen atom, wherein at least one of $X^1$ and $X^2$ is a halogen atom.

5. The hyaluronic acid compound according to claim 1, wherein the non-steroidal anti-inflammatory drug is represented by the following formula:

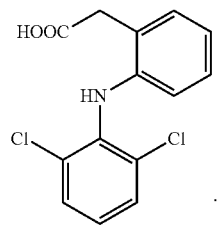

6. The hyaluronic acid compound according to claim 1, wherein the hyaluronic acid has a weight average molecular weight of from 500,000 to 3,000,000.

7. The hyaluronic acid compound according to claim 1, wherein $R^1$ in formula (1) is selected from the group consisting of an ethylene group, a trimethylene group, and a propylene group, which may have one or more substituents.

8. The hyaluronic acid compound according to claim 1, which is obtainable by a method comprising reacting hyaluronic acid with a spacer-bound non-steroidal anti-inflammatory drug, or reacting a spacer-bound hyaluronic acid with a non-steroidal anti-inflammatory drug, and adjusting the reaction solution to alkaline conditions.

9. The hyaluronic acid compound according to claim 1, wherein a solution obtained by dissolving the hyaluronic acid compound in an aqueous medium to a concentration of 1.0% by weight is capable of passing through a porous filter having a pore size of 0.45 μm and a diameter of 25 mm, at a ratio of 2 mL per minute or more at a temperature of 24° C. under a pressure of 5.0 kg/cm².

10. The hyaluronic acid compound according to claim 1, wherein a solution obtained by dissolving the hyaluronic acid compound in an aqueous medium to a concentration of 1.0% by weight is capable of passing through a porous filter having a pore size of 0.22 μm and a diameter of 25 mm, at a ratio of 2 mL per minute or more at a temperature of 24° C. under a pressure of 5.0 kg/cm².

11. A hyaluronic acid compound solution which is capable of being pushed out from an injector and which comprises the hyaluronic acid compound according to any one of claims 1 to 10 dissolved in an aqueous medium.

12. The hyaluronic acid compound solution according to claim 11, wherein the aqueous medium is an aqueous medium selected from the group consisting of phosphate buffered saline, saline and water for injection.

13. The hyaluronic acid compound solution according to claim 12, which is sterilized through a filter.

14. A pharmaceutical composition which comprises the hyaluronic acid compound according to claim 1 as an active ingredient and a pharmaceutically acceptable carrier.

15. The pharmaceutical composition according to claim 14, which is an arthritis treating agent, an anti-inflammatory medicament or an analgesic.

16. The pharmaceutical composition according to claim 14, which is useful for parenteral administration.

17. The pharmaceutical composition according to claim 16, which is an injection useful for topical administration.

18. The pharmaceutical composition according to claim 16, which is an injection useful for intra-articular administration.

19. A pharmaceutical composition which is capable of being pushed out from an injector and which comprises a solution in which the hyaluronic acid compound according to claim 1, as an active ingredient, is dissolved in an aqueous medium.

20. A kit for injection of a hyaluronic acid compound, which comprises the hyaluronic acid compound solution according to claim 11, which is filled in an injector capable of pushing out the solution.

21. The kit according to claim 20, wherein the filled solution is a pharmaceutical composition which comprises a hyaluronic acid compound as an active ingredient and a pharmaceutically acceptable carrier,
wherein the hyaluronic acid compound is a hyaluronic acid compound in which a non-steroidal anti-inflammatory drug is bound to hyaluronic acid through a covalent bond, wherein a partial structure of a hyaluronic acid disaccharide unit into which the anti-inflammatory drug is introduced is represented by the following formula (1):

$$Y-CO-NH-R^1-(O-R^2)_n \quad (1)$$

wherein Y—CO— represents the glucuronic acid residue of the hyaluronic acid disaccharide unit;
$R^2$ represents a hydrogen atom or a non-steroidal anti-inflammatory drug residue, and at least one $R^2$ is a non-steroidal anti-inflammatory drug residue;
—NH—$R^1$—O—)$_n$ represents a spacer residue in a spacer compound represented by $H_2N-R^1-(OH)_n$ having n numbers of a hydroxyl group.
$R^1$ represents a linear or branched hydrocarbon group having from 2 to 12 carbon atoms which may have a substituent;
—CO—NH— represents an amide bond of a carboxyl group in glucuronic acid as a constituting saccharide of the hyaluronic acid with an amino group in the spacer compound;
wherein a hydroxyl group in the spacer compound forms an ester bond with a carboxyl group in the non-steroidal anti-inflammatory drug residue; and
n is an integer of from 1 to 3,
wherein the hyaluronic acid compound has a degree of substitution of the non-steroidal anti-inflammatory drug of from 5 to 50 mol % per repeating disaccharide unit of hyaluronic acid, and the carbonyl group in a hyaluronic acid residue constituting the hyaluronic acid compound is present as an amide bond participating in the binding with the spacer-binding anti-inflammatory drug residue or as a free carboxyl group not participating therein, according to the degree of substitution of the non-steroidal anti-inflammatory drug residue.

22. A medical injection kit which is sealed with a plunger for medicament extrusion in such a manner that it can be slid and which comprises a syringe filled with a solution in which the hyaluronic acid compound according to claim 1 is dissolved in pharmaceutically acceptable phosphate buffered saline, saline or water for injection.

* * * * *